US010391098B2

(12) United States Patent
Geller et al.

(10) Patent No.: US 10,391,098 B2
(45) Date of Patent: *Aug. 27, 2019

(54) ANTISENSE ANTIBACTERIAL COMPOUNDS AND METHODS

(71) Applicants: Oregon State University, Corvallis, OR (US); Board of Regents, The University of Texas System, Austin, TX (US)

(72) Inventors: Bruce L. Geller, Corvallis, OR (US); David Greenberg, Coppell, TX (US)

(73) Assignees: Board of Regents, The University of Texas System, Austin, TX (US); Oregon State University, Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,104

(22) Filed: May 15, 2015

(65) Prior Publication Data

US 2016/0106857 A1   Apr. 21, 2016

Related U.S. Application Data

(60) Provisional application No. 62/129,746, filed on Mar. 6, 2015, provisional application No. 62/000,431, filed on May 19, 2014.

(51) Int. Cl.
| | | |
|---|---|---|
| A61K 45/06 | (2006.01) | |
| C12N 15/113 | (2010.01) | |
| A61K 31/5377 | (2006.01) | |
| A61K 31/712 | (2006.01) | |
| A61K 31/7036 | (2006.01) | |
| A61K 47/64 | (2017.01) | |

(52) U.S. Cl.
CPC ...... *A61K 31/5377* (2013.01); *A61K 31/7036* (2013.01); *A61K 31/712* (2013.01); *A61K 45/06* (2013.01); *A61K 47/645* (2017.08); *C12N 15/113* (2013.01); *C12N 2310/3233* (2013.01); *C12N 2310/3513* (2013.01); *Y02A 50/473* (2018.01)

(58) Field of Classification Search
CPC ............... A61K 31/712; C12N 15/113; C12N 2310/3233
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,698,685 A | 12/1997 | Summerton et al. |
| 6,245,747 B1 | 6/2001 | Porter et al. |
| 6,965,025 B2 | 11/2005 | Gaarde et al. |
| 6,969,400 B2 | 11/2005 | Rhee et al. |
| 7,625,873 B2 * | 12/2009 | Geller ............... C07F 9/65583 435/471 |
| 7,790,694 B2 | 9/2010 | Geller et al. |
| 8,067,571 B2 | 11/2011 | Weller et al. |
| 8,076,476 B2 | 12/2011 | Reeves et al. |
| 8,299,206 B2 | 10/2012 | Fox et al. |
| 8,314,072 B2 | 11/2012 | Geller et al. |
| 8,536,147 B2 * | 9/2013 | Weller ............... A61K 48/00 514/44 A |
| 9,249,243 B2 * | 2/2016 | Weller ............... A61K 48/00 |
| 9,790,495 B2 | 10/2017 | Geller et al. |
| 2004/0029129 A1 | 2/2004 | Wang et al. |
| 2005/0288246 A1 | 12/2005 | Iversen et al. |
| 2006/0241075 A1 | 10/2006 | McSwiggen |
| 2006/0270621 A1 | 11/2006 | Christiano |
| 2007/0049542 A1 | 3/2007 | Geller et al. |
| 2008/0194463 A1 | 8/2008 | Weller et al. |
| 2010/0016215 A1 | 1/2010 | Moulton et al. |
| 2010/0234281 A1 | 9/2010 | Weller et al. |
| 2010/0261777 A1 | 10/2010 | Shaw et al. |
| 2012/0040460 A1 | 2/2012 | Rigoutsos et al. |
| 2012/0122769 A1 | 5/2012 | Iversen |
| 2012/0213663 A1 | 8/2012 | Atieh et al. |
| 2012/0289457 A1 | 11/2012 | Hanson |
| 2012/0296087 A1 | 11/2012 | Sinha et al. |
| 2013/0197220 A1 | 8/2013 | Ueda |
| 2013/0288369 A1 | 10/2013 | Iverson |
| 2015/0141321 A1 | 5/2015 | Kole et al. |
| 2015/0361425 A1 | 12/2015 | Geller et al. |

FOREIGN PATENT DOCUMENTS

| | | |
|---|---|---|
| KR | 2013/0005208 A | 1/2013 |
| WO | WO 1993/001286 A2 | 1/1993 |
| WO | WO 2004/097017 A2 | 11/2004 |
| WO | WO 2006/085973 A2 | 8/2006 |
| WO | WO 2007/009094 A2 | 1/2007 |
| WO | WO 2008/008113 A1 | 1/2008 |
| WO | WO 2009/005793 A2 | 1/2009 |
| WO | WO 2009/064471 A1 | 5/2009 |

(Continued)

OTHER PUBLICATIONS

GenBank 01251363 [KR 1020130005208-A/39: Method and kit for detecting carbapenem resistant enterobacteriaceae using real-time PCR] (retrieved on Oct. 13, 2015 from http://www.ncbi.nlm.nih.gov/nucleotide/662699238?report=genbank&log$=nuclalign&blast_rank=1&RID=1V403DGD016] Jul. 8, 2014 (Jul. 8, 2014) whole doc.

(Continued)

*Primary Examiner* — Brian Whiteman
(74) *Attorney, Agent, or Firm* — Parker Highlander PLLC

(57) ABSTRACT

Provided are antisense oligomers targeted against or genes associated with a biochemical pathway and/or cellular process, and related compositions and methods of using the oligomers and compositions to treat an infected mammalian subject, for example, as primary antimicrobials or as adjunctive therapies with classic antimicrobials.

16 Claims, 26 Drawing Sheets

Specification includes a Sequence Listing.

(56) References Cited

FOREIGN PATENT DOCUMENTS

| WO | WO 2012/043730 A1 | 4/2012 |
|---|---|---|
| WO | WO 2012/064991 A1 | 5/2012 |
| WO | WO 2012/150960 A1 | 11/2012 |
| WO | WO 2013/011072 A1 | 1/2013 |
| WO | WO 2015/175977 A2 | 11/2015 |
| WO | WO 2015/179249 A1 | 11/2015 |
| WO | WO 2016/108930 A2 | 7/2016 |
| WO | WO 2017/112885 A1 | 6/2017 |
| WO | WO 2017/112888 A1 | 6/2017 |

OTHER PUBLICATIONS

PCT/US2015/031150, International Search Report and Written Opinion dated Jan. 14, 2016.
PCT/US2015/031213, International Search Report and Written Opinion dated Sep. 2, 2015.
PCT/US2015/000280, International Search Report and Written Opinion dated May 2, 2016.
Summerton et al. 1997, "Morpholino antisense oligomers: design, preparation, and properties." Antisense and Nucleic Acid Drug Development (1997); 7.3: 187-195.
EP 15795398.5, Partial Supplementary European Search Report dated Nov. 29, 2017, 7 pages.
Greenberg, et al., "Antisense Phosphorodiamidate Morpholino Oligomers Targeted to an Essential Gene Inhibit Burkholderia cepacia Complex." The Journal of Infectious Diseases (2010); 12: 1822-1830.
EP 15792493.7, Partial Supplementary European Search Report dated Nov. 29, 2017, 10 pages.
Youngblood, Derek S., et al. "Stability of cell-penetrating peptide-morpholino oligomer conjugates in human serum and in cells." Bioconjugate Chemistry (2007); 18.1: 50-60.
PCT/US2015/031150, International Preliminary Report on Patentability dated Nov. 22, 2016, 11 pages.
PCT/US2015/031213, International Preliminary Report on Patentability dated Nov. 22, 2016, 7 pages.
Nikaido et al., "Broad-specificity efflux pumps and their role in multidrug resistance of Gram-negative bacteria," *FEMS Microbial Rev.*, 36:340-363, 2012.

* cited by examiner

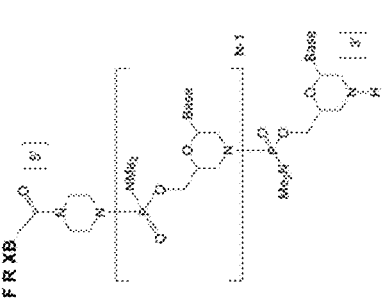
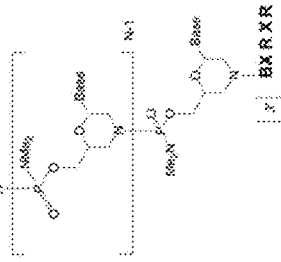
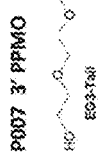
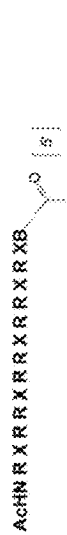
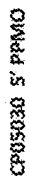
Fig. 1F, Fig. 1G, Fig. 1H

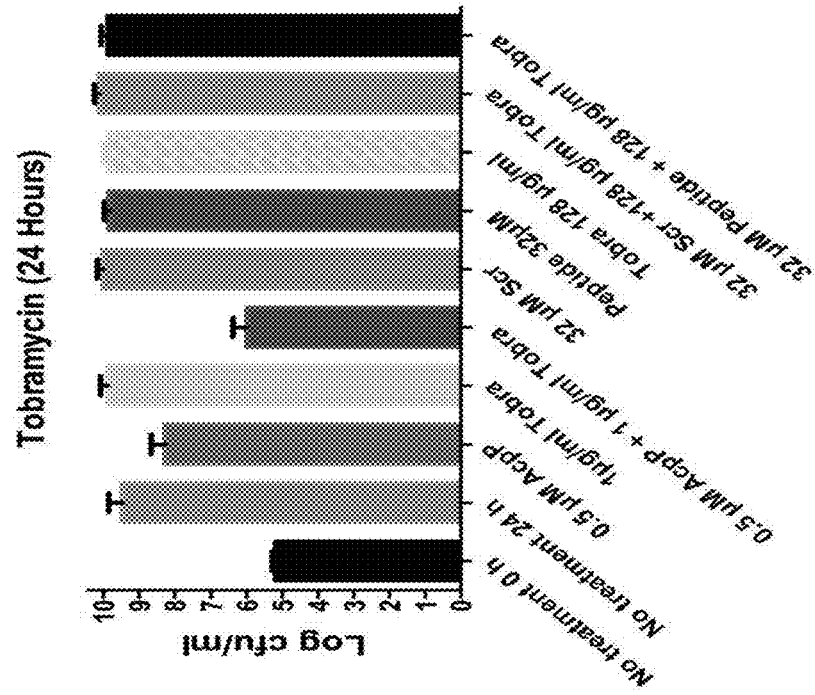
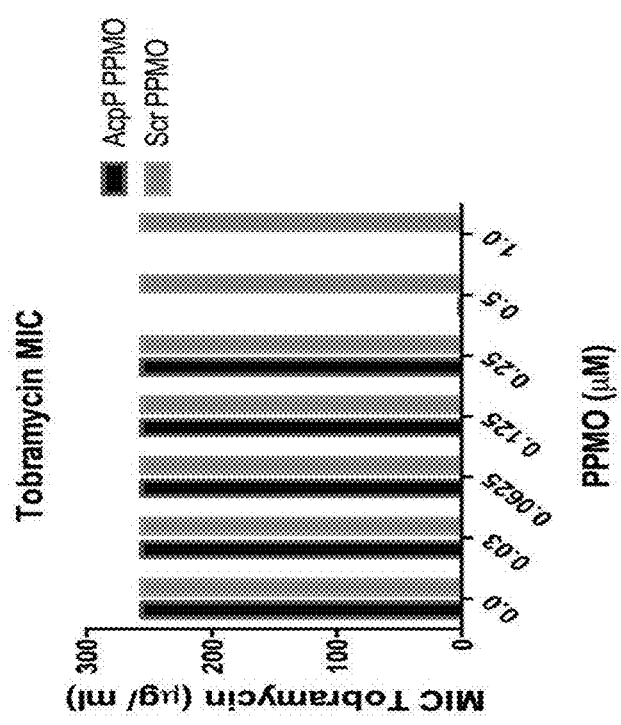
Fig. 12E
Fig. 12F

FIG. 13B

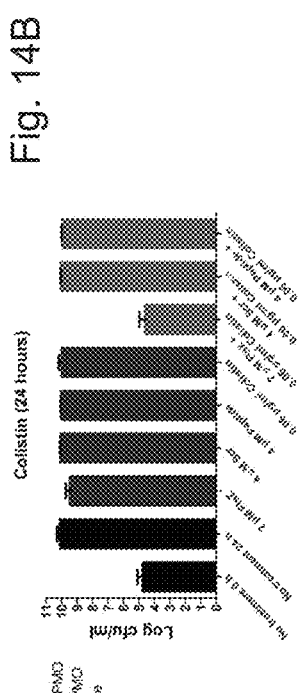
Fig. 14A
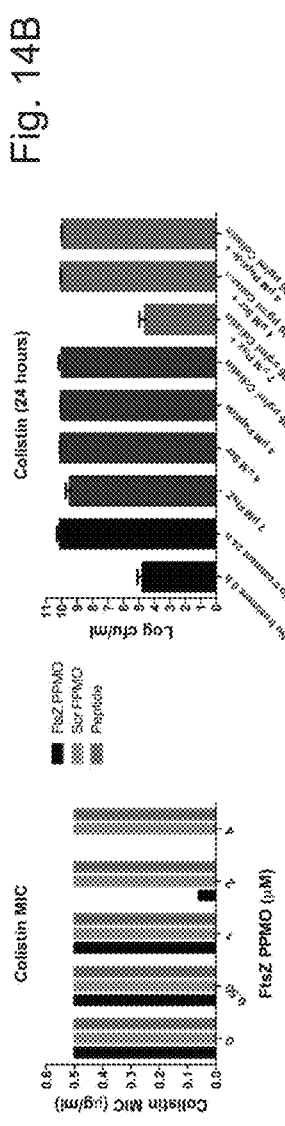
Fig. 14B
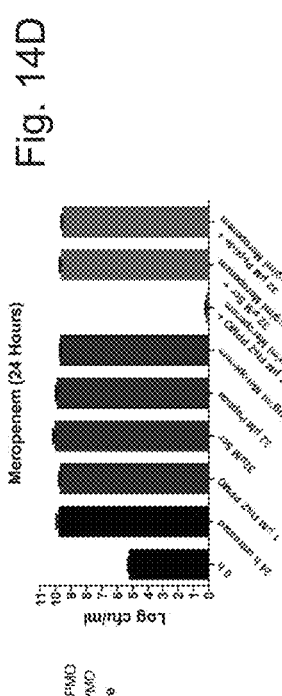
Fig. 14C
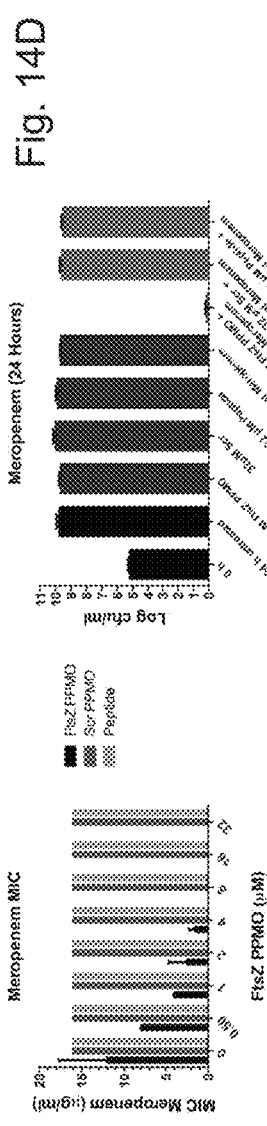
Fig. 14D
Fig. 14E
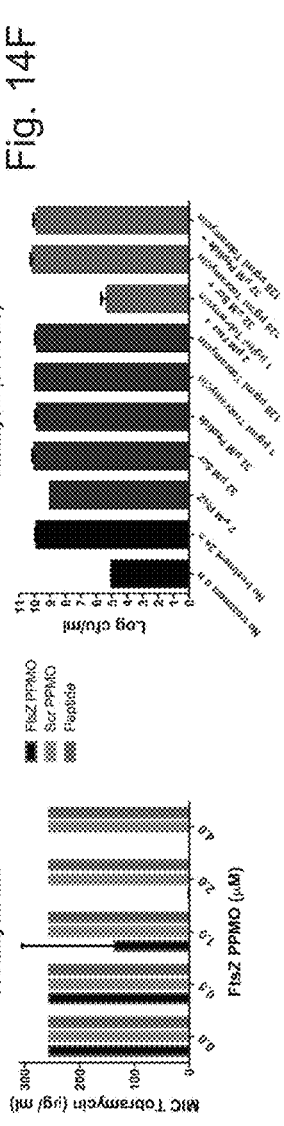
Fig. 14F

ANTISENSE ANTIBACTERIAL COMPOUNDS AND METHODS

CROSS-REFERENCE TO RELATED APPLICATIONS

This application claims priority under 35 U.S.C. § 119(e) to U.S. Application No. 62/000,431, filed May 19, 2014; and U.S. Application No. 62/129,746, filed Mar. 6, 2015; each of which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is SATH-004_01 US_ST25.txt. The text file is about 15 KB, was created on May 15, 2015, and is being submitted electronically via EFS-Web.

BACKGROUND

Technical Field

The present disclosure includes antisense oligomers targeted against bacterial genes involved in a biochemical pathway and/or cellular process, and related compositions and methods of using the oligomers and compositions to treat an infected mammalian subject, for example, as primary antimicrobials or as adjunctive therapies with classic antimicrobials.

Description of the Related Art

Currently, there are several types of antibiotic compounds in use against bacterial pathogens and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and trans-peptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamicin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive by cleaving the lactam ring. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

*Escherichia coli* normally inhabits the large intestine of humans as a commensal organism. However, it can also cause a variety of clinical infections, and is a leading cause of bacteremia. There has been an alarming increase in the number of antibiotic-resistant strains of *E. coli* isolated from patients with nosocomial and community-acquired bacteremia. It is not uncommon for strains to be resistant to multiple antibiotics.

*Acinetobacter baumannii* is a ubiquitous organism that has emerged over the years to be a significant cause of hospital-acquired infections. This change in epidemiology is especially concerning given that *A. baumannii* has become one of the most antibiotic-resistant Gram-negative pathogens that the medical community faces world-wide. The rapid increase in multi-drug resistance in *A. baumannii* has left few therapeutic choices for the treating physician. Drugs such as colistin are now frequently used, although colistin-resistant strains have appeared. *Acinetobacter baumannii* can cause a variety of clinical infections, with pneumonia being one of the most frequent.

The appearance of antibiotic resistance in many pathogenic bacteria, including cases involving multi-drug resistance (MDR), raises the fear of a post-antibiotic era in which many bacterial pathogens were simply untreatable by medical intervention. Thus, there is a need for antimicrobial agents that (i) are not subject to the principal types of antibiotic resistance currently hampering antibiotic treatment of bacterial infection, (ii) can be developed rapidly and with some reasonable degree of predictability as to target-bacteria specificity, (iii) are effective at low doses, and (iv) show few side effects.

BRIEF SUMMARY

Embodiments of the present disclosure relate, in part, to the discovery that the antisense targeting of bacterial genes associated with biochemical pathways, cellular processes, and/or antibiotic resistance can increase the antibiotic susceptibility of otherwise antibiotic-resistant pathogenic bacteria, and reduce the ability of certain pathogenic bacteria to grow. For example, the antisense targeting of genes associated with RNA biosynthesis, protein biosynthesis, fatty acid biosynthesis, peptidoglycan biosynthesis, cellular energy homeostasis, cell division, aromatic compound biosynthesis, and antibiotic resistance was shown to increase the cell-killing and/or antibiotic susceptibility of antibiotic resistant (e.g., multi-drug resistant) bacteria to many commonly used antibiotics. In many instances, the antisense oligomers described herein were shown to be bactericidal at clinically-relevant concentrations and to display synergy with multiple classic antibiotics in *Acinetobacter* and *Escherichia*, including multiple drug-resistant (MDR) strains. The antisense oligomers described herein could thus find utility in the treatment of such bacteria, for instance, in combination with antibiotics or as standalone therapies.

Embodiments of the present disclosure therefore include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a protein associated with a biochemical pathway and/or cellular process, or a protein associated with antibiotic resistance, as described herein. In some instances, the oligomer is conjugated to a cell-penetrating peptide (CPP).

In certain embodiments, the targeting sequence is selected from Tables 2A-B. In some embodiments, the oligomer is about 10-15 or about 11-12 nucleotide bases in length and has a targeting sequence selected from Tables 2A-B.

In certain embodiments, an antisense oligomer of the disclosure is of formula (I):

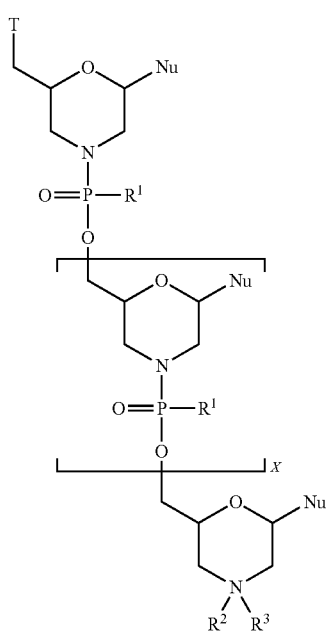

(I)

or a pharmaceutically acceptable salt thereof,
where each Nu is a nucleobase which taken together forms a targeting sequence;
X is an integer from 9 to 38;
T is selected from OH and a moiety of the formula:

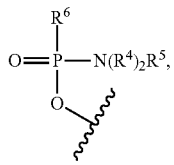

where each $R^4$ is independently $C_1$-$C_6$ alkyl, and $R^5$ is selected from an electron pair and H, and $R^6$ is selected from OH, —N($R^7$)CH$_2$C(O)NH$_2$, and a moiety of the formula:

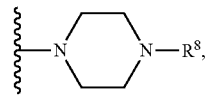

where:
$R^7$ is selected from H and $C_1$-$C_6$ alkyl, and
$R^8$ is selected from G, —C(O)—$R^9$OH, acyl, trityl, and 4-methoxytrityl, where:
  $R^9$ is of the formula —(O-alkyl)$_y$- wherein y is an integer from 3 to 10 and each of
  the y alkyl groups is independently selected from $C_2$-$C_6$ alkyl;
each instance of $R^1$ is —N($R^{10}$)$_2$$R^{11}$ wherein each $R^{10}$ is independently $C_1$-$C_6$ alkyl, and $R^{11}$ is
selected from an electron pair and H;
$R^2$ is selected from H, G, acyl, trityl, 4-methoxytrityl, benzoyl, stearoyl, and a moiety of the formula:

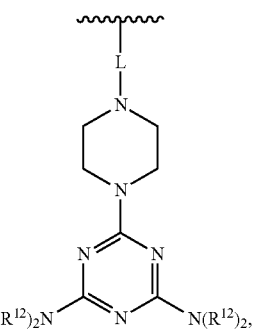

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{14}$)$_2$ wherein each $R^{14}$ is of the formula —(CH$_2$)$_6$NHC(=NH)NH$_2$; and
$R^3$ is selected from an electron pair, H, and $C_1$-$C_6$ alkyl, wherein G is a cell penetrating peptide ("CPP") and linker moiety selected from
—C(O)(CH$_2$)$_6$NH-CPP, —C(O)(CH$_2$)$_2$NH-CPP, —C(O)(CH$_2$)$_2$NHC(O)(CH$_2$)$_5$NH-CPP,
and —C(O)CH$_2$NH-CPP, or G is of the formula:

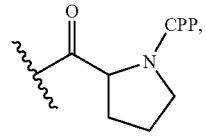

wherein the CPP is attached to the linker moiety by an amide bond at the CPP carboxy terminus, with the proviso that only one instance of G is present,
wherein the targeting sequence specifically hybridizes to a bacterial mRNA target sequence that encodes a protein associated with a biochemical pathway and/or cellular process or a protein associated with antibiotic resistance, as described herein.

In some embodiments, the target sequence comprises a translational start codon of the bacterial mRNA and/or a sequence within about 30 bases upstream or downstream of the translational start codon of the bacterial mRNA.

In some embodiments, the protein associated with a biochemical pathway and/or cellular process is a fatty acid biosynthesis protein. In certain embodiments, the fatty acid biosynthesis protein is an acyl carrier protein. In certain embodiments, the acyl carrier protein is AcpP. In some embodiments, the target sequence is SEQ ID NO: 69 or 70, and where thymine bases (T) are optionally uracil bases (U). In certain embodiments, the fatty acid biosynthesis protein is a carboxyltransferase alpha subunit of an acetyl Coenzyme A carboxylase. In certain embodiments, the carboxyltransferase alpha subunit of an acetyl Coenzyme A carboxylase is AccA. In certain embodiments, the targeting sequence is set forth in SEQ ID NOS: 1-11, comprises a fragment of at least 10 contiguous nucleotides of SEQ ID NOS: 1-11, or comprises a variant having at least 80% sequence identity to SEQ ID NOS: 1-11, where thymine bases (T) are optionally uracil bases (U).

In some embodiments, the protein associated with a biochemical pathway and/or cellular process is a peptidoglycan biosynthesis protein. In certain embodiments, the peptidoglycan biosynthesis protein is a UDP-N-acetylglucosamine 1-carboxyvinyltransferase. In particular embodiments, the UDP-N-acetylglucosamine 1-carboxyvinyltransferase is MurA.

In certain embodiments, the protein associated with a biochemical pathway and/or cellular process is a ribosomal protein. In some embodiments, the ribosomal protein is a 50S ribosomal protein L28.

In certain embodiments, the 50S ribosomal protein L28 is RpmB. In particular embodiments, the protein associated with a biochemical pathway and/or cellular process is a cellular energy homeostasis protein.

In certain embodiments, the cellular energy homeostasis protein is an adenylate kinase. In specific embodiments, the adenylate kinase is Adk.

In certain embodiments, the protein associated with a biochemical pathway and/or cellular process is a protein biosynthesis protein. In some embodiments, the protein biosynthesis protein is a translation initiation factor. In various embodiments, the translation initiation factor is InfA.

In certain embodiments, the protein associated with a biochemical pathway and/or cellular process is a cell division protein. In particular embodiments, the cell division protein is a protein that assembles into a ring at the future site of the septum of bacterial cell division.

In some embodiments, the protein that assembles into a ring at the future site of the septum of bacterial cell division is FtsZ. In certain embodiments, the protein associated with a biochemical pathway and/or cellular process is an RNA synthesis protein.

In certain embodiments, the RNA synthesis protein is a sigma D factor of RNA polymerase. In particular embodiments, the sigma D factor of RNA polymerase is RpoD.

In some embodiments, the protein associated with a biochemical pathway and/or cellular process is an aromatic compound biosynthesis protein. In some embodiments, the aromatic compound biosynthesis protein is a chorismate synthase (5-enolpyruvylshikimate-3-phosphate phospholyase). In particular embodiments, the chorismate synthase (5-enolpyruvylshikimate-3-phosphate phospholyase) is AroC.

In specific embodiments, the targeting sequence is set forth in SEQ ID NOS: 12-53, comprises a fragment of at least 10 contiguous nucleotides of SEQ ID NOS: 12-53, or comprises a variant having at least 80% sequence identity to SEQ ID NOS: 12-53, where thymine bases (T) are optionally uracil bases (U).

In certain embodiments, the protein associated with antibiotic resistance is selected from at least one of TEM beta-lactamase (BlaT), chloramphenicol resistance gene Cml, and resistance-nodulation-cell division (RND)-type multidrug efflux pump subunit AdeA (adeA). In particular embodiments, the targeting sequence is set forth in SEQ ID NOS: 54-56, comprises a fragment of at least 10 contiguous nucleotides of SEQ ID NOS: 54-56, or comprises a variant having at least 80% sequence identity to SEQ ID NOS: 54-56, and where thymine bases (T) are optionally uracil bases (U).

Also included are pharmaceutical compositions, comprising a pharmaceutically acceptable carrier and an antisense oligomer described herein. Some pharmaceutical compositions further comprising an antimicrobial agent as described herein, such as one or more of tobramycin, meropenem, and/or colistin.

Some embodiments include methods of reducing expression and activity of a protein selected from at least at least one of a protein associated with a biochemical pathway and/or cellular process and antibiotic resistance in a bacterium, comprising contacting the bacterium with an antisense oligomer and/or a pharmaceutical composition described herein.

In certain embodiments, the bacterium is in a subject, and the method comprises administering the antisense oligomer to the subject. In some embodiments, the bacterium is selected from the genera *Escherichia* and *Acinetobacter*. In particular embodiments, the bacterium is an antibiotic-resistant strain of *Escherichia* or *Acinetobacter*. In some embodiments, the bacterium is a multi-drug resistant (MDR) strain of *Escherichia* or *Acinetobacter*. In specific embodiments, the bacterium is *Escherichia coli* or *Acinetobacter baumannii*.

In certain embodiments, the protein associated with a biochemical pathway and/or cellular process is an acyl carrier protein. In some embodiments, the bacterium is *Escherichia coli* and the acyl carrier protein is an AcpP protein encoded by acpP. In certain embodiments, the bacterium is *Acinetobacter baumannii* and where the acyl carrier protein is an AcpP protein encoded by acpP.

In some embodiments, the bacterium is *Acinetobacter* spp. and the protein associated with a biochemical pathway and/or cellular process is a carboxyltransferase alpha subunit of an acetyl Coenzyme A carboxylase encoded by accA.

In certain embodiments, the bacterium is *Escherichia coli* and the protein associated with a biochemical pathway and/or cellular process is a UDP-N-acetylglucosamine 1-carboxyvinyltransferase encoded by murA.

In some embodiments, the bacterium is *Escherichia coli* and the protein associated with a biochemical pathway and/or cellular process is a ribosomal protein encoded by rpmB.

In particular embodiments, the bacterium is *Escherichia coli* and the protein associated with a biochemical pathway and/or cellular process is an adenylate kinase encoded by adk.

In some embodiments, the bacterium is *Escherichia coli* and the protein associated with a biochemical pathway and/or cellular process is a translation initiation factor encoded by infA.

In certain embodiments, the bacterium is *Acinetobacter* spp. and the protein associated with a biochemical pathway and/or cellular process is a protein that assembles into a ring at the future site of the septum of bacterial cell division encoded by ftsZ.

In some embodiments, the bacterium is *Acinetobacter* spp. and the protein associated with a biochemical pathway and/or cellular process is a sigma D factor of RNA polymerase encoded by rpoD.

In some embodiments, the bacterium is *Acinetobacter* spp. and the protein associated with a biochemical pathway and/or cellular process is a chorismate synthase (5-enolpyruvylshikimate-3-phosphate phospholyase) encoded by aroC.

In particular embodiments, the bacterium is *Escherichia coli* or *Acinetobacter baumannii* and the protein associated with antibiotic resistance is selected from at least one of BlaT, Cml, and AdeA.

Some methods comprise administering the oligomer separately or concurrently with an antimicrobial agent, optionally where administration of the oligomer increases susceptibility of the bacterium to the antimicrobial agent.

In certain embodiments, the antimicrobial agent is selected from one or more of a β-lactam antibiotic, an aminoglycoside antibiotic, and a polymyxin.

In some embodiments, the β-lactam antibiotic is selected from at least one of carbapenems, penicillin derivatives (penams), cephalosporins (cephems), and monobactams.

In particular embodiments, the carbapenem is selected from one or more of meropenem, imipenem, ertapenem, doripenem, panipenem, biapenem, razupenem, tebipenem, lenapenem, and tomopenem. In specific embodiments, the carbapenem is meropenem.

In certain embodiments, the aminoglycoside antibiotic is selected from one or more of tobramycin, gentamicin, kanamycin a, amikacin, dibekacin, sisomicin, netilmicin, neomycin B, neomycin C, neomycin E (paromomycin), and streptomycin. In specific embodiments, the aminoglycoside antibiotic is tobramycin.

In certain embodiments, the polymyxin is selected from one or more of colistin (polymyxin E), polysporin, neosporin, or polymyxin B. In specific embodiments, the polymyxin is colistin.

In certain embodiments, the bacterium is *Escherichia coli* or *Acinetobacter* spp. that expresses BlaT, and the antimicrobial agent is a β-lactam antibiotic. In some embodiments, the (β-lactam antibiotic is selected from at least one of meropenem, imipenem, ertapenem, doripenem, panipenem, biapenem, razupenem, tebipenem, lenapenem, tomopenem, cephalosporins (cephems), penicillin, penicillin derivatives (penams) and ampicillin.

In particular embodiments, the bacterium is *Escherichia coli* or *Acinetobacter* spp. that expresses cml, and the antimicrobial agent is chloramphenicol. In certain embodiments, the bacterium is *Escherichia coli* or *Acinetobacter* spp. that expresses adeA, and where the antimicrobial agent is selected from at least one of aminoglycoside antibiotics, tetracycline antibiotics, and (β-lactam antibiotics.

In certain embodiments, the aminoglycoside antibiotic is selected from at least one of tobramycin, gentamicin, kanamycin a, amikacin, dibekacin, sisomicin, netilmicin, neomycin B, neomycin C, neomycin E (paromomycin), and streptomycin.

In some embodiments, the tetracycline antibiotic is selected from at least one of tetracycline, chlortetracycline, oxytetracycline, demeclocycline, lymecycline, meclocycline, methacycline, minocycline, rolitetracycline, and doxycyline.

In particular embodiments, the β-lactam antibiotic is selected from at least one of carbapenems, penicillin derivatives (penams), cephalosporins (cephems), and monobactams.

In some embodiments, the bacterium is *Acinetobacter* spp., the protein associated with a biochemical pathway and/or cellular process is a carboxyltransferase alpha subunit of an acetyl Coenzyme A carboxylase encoded by accA, and the antimicrobial agent is selected from at least one of aminoglycoside antibiotics, tetracycline antibiotics, and β-lactam antibiotics.

In some embodiments, the bacterium is *Escherichia coli*, the protein associated with a biochemical pathway and/or cellular process is a UDP-N-acetylglucosamine 1-carboxyvinyltransferase encoded by murA, and the antimicrobial agent is selected from at least one of aminoglycoside antibiotics, tetracycline antibiotics, and β-lactam antibiotics.

In particular embodiments, the bacterium is *Escherichia coli* or *Acinetobacter* spp., the protein associated with a biochemical pathway and/or cellular process is a ribosomal protein encoded by rpmB, and the antimicrobial agent is selected from at least one of aminoglycoside antibiotics, tetracycline antibiotics, and β-lactam antibiotics.

In certain embodiments, the bacterium is *Escherichia coli*, the protein associated with a biochemical pathway and/or cellular process is an adenylate kinase encoded by adk, and the antimicrobial agent is selected from at least one of aminoglycoside antibiotics, tetracycline antibiotics, and β-lactam antibiotics.

In some embodiments, the bacterium is *Escherichia coli*, the protein associated with a biochemical pathway and/or cellular process is a translation initiation factor encoded by infA, and the antimicrobial agent is selected from at least one of aminoglycoside antibiotics, tetracycline antibiotics, and β-lactam antibiotics.

In some embodiments, the bacterium is *Acinetobacter* spp., the protein associated with a biochemical pathway and/or cellular process is a protein that assembles into a ring at the future site of the septum of bacterial cell division encoded by ftsZ, and the antimicrobial agent is selected from at least one of aminoglycoside antibiotics, tetracycline antibiotics, and β-lactam antibiotics.

In certain embodiments, the bacterium is *Acinetobacter* spp., the protein associated with a biochemical pathway and/or cellular process is a sigma D factor of RNA polymerase encoded by rpoD, and the antimicrobial agent is selected from at least one of aminoglycoside antibiotics, tetracycline antibiotics, and β-lactam antibiotics.

In particular embodiments, the bacterium is *Acinetobacter* spp., the protein associated with a biochemical pathway and/or cellular process is a chorismate synthase (5-enolpyruvylshikimate-3-phosphate phospholyase) encoded by aroC, and the antimicrobial agent is selected from at least one of aminoglycoside antibiotics, tetracycline antibiotics, and β-lactam antibiotics.

In some embodiments, the oligomer reduces the minimum inhibitory concentration (MIC) of the antimicrobial agent against the bacterium by at least about 10% relative to the antimicrobial agent alone.

In some embodiments, the oligomer increases the susceptibility of the bacterium to the antimicrobial agent by at least about 10% relative to the antimicrobial agent alone.

In certain embodiments, the combination of oligomer and the antimicrobial agent synergistically increases the susceptibility of the bacterium to the antibiotic relative to the oligomer and/or the microbial agent alone. In particular embodiments, the antimicrobial agent is selected from colistin, meropenem, and tobramycin.

In certain embodiments, the antimicrobial agent and the antisense oligomer are administered separately. In various embodiments, the antimicrobial agent and the antisense oligomer are administered sequentially. In some embodiments, the antimicrobial agent and the antisense oligomer are administered concurrently.

Also included are methods of treating a multi-drug-resistant (MDR) *Acinetobacter baumannii* or *Escherichia coli* bacterial infection in a subject, comprising administering to the subject an antibiotic selected from one or more of tobramycin, meropenem, and colistin, in combination with an antisense oligomer described herein. Certain antisense oligomers comprise a targeting sequence of sufficient length and complementarity to specifically hybridize to an mRNA target sequence of a bacterial acpP gene that encodes an acyl carrier protein (AcpP), where the combination of the antisense oligomer and the antibiotic synergistically increases the susceptibility of the MDR *Acinetobacter* or the MDR *Escherichia coli* to the antibiotic relative to the antibiotic alone.

BRIEF DESCRIPTION OF THE FIGURES

FIGS. 1F-H show exemplary peptide PMO conjugates structures used in the exemplary PPMOs.

FIG. 9A shows the results for *E. coli* W3110 challenged with acpP (PPMO#1), acpP (PPMO#2), acpP (PPMO#3), acpP (PPMO#4), acpP (PPMO#5), murA (PPMO#24), and Scramble (Scr) controls. FIGS. 9B-9C shows the results for *A. baumannii* AYE (9B) and *A. baumannii* 0057 (9C) challenged with acpP (PPMO#7), acpP (PPMO#8), acpP (PPMO#13), acpP (PPMO#14), ftsZ (PPMO#33), ftsZ (PPMO#34), rpmB (PPMO#29), and Scramble (Scr) controls. The bacteria were challenged in either MHII (black bar) or AB Minimal Media (grey bar).

FIG. 10A shows the results for *E. coli* 1101851 challenged with PPMOs acpP(PPMO#3) and (RFR)4-Scramble (Scr) control. FIGS. 10B-10C respectively show the results for *A. baumannii* AYE and AB0057 challenged with PPMOs acpP (PPMO#7) and (RXR)4-Scramble (Scr) control.

FIGS. 11A-11B show *A. baumannii* AYE before treatment with PPMOs and FIGS. 11G-11H shows after a 6 hour incubation alone. FIGS. 11C-11D show the results for 40 μM scramble control at 0 hour and FIGS. 11I-11J show the results for 40 μM scramble control at 6 hours treatment. FIGS. 11E-11F show the results for 40 μM acpP at 0 hour and FIGS. 11K-11L show the results for 40 μM at 6 hours treatment. CW, cell wall section; arrows point out cell wall disruption.

FIGS. 12A-12F show the synergy between acpP-targeted PPMOs and three different antibiotics against the multidrug-resistant *E. coli* strain AIS070834. The MIC of colistin, meropenem, and tobramycin was measured with various concentrations of acpP-targeted PPMO (PPMO#1) or scrambled (Scr) control PPMO. Viable cells were counted in 24-hour cultures with antibiotic alone, PPMO alone, or in combination thereof. FIGS. 12A-12B show the results for colistin, FIGS. 12C-12D show the results for meropenem, and FIGS. 12E-12F show the results for tobramycin. In all instances, the acpP-targeted PPMO significantly reduced the MIC of the tested antibiotics. The free peptide (RXR)4XB was also tested and by itself had an unmeasurable MIC (data not shown). Error bars indicate standard deviation (N=2 for all experiments).

FIGS. 13A-13D show the MICs of PPMOs targeted against various genes in selected bacterial strains. FIG. 13A shows the results for *E. coli* strains grown in MHII. FIG. 13B shows the results for *E. coli* strains grown in MOPS minimal media. FIG. 13C shows the results for *Acinetobacter* species grown in MHII. FIG. 13D shows the results for *Acinetobacter* species grown in AB minimal media.

FIGS. 14A-14F show synergy of ftsZ PPMO with 3 antibiotics. The MIC of classic antibiotics (FIG. 14A, FIG. 14C, FIG. 14E) was measured with various concentrations of ftsZ PPMO (PPMO#46) or scrambled (Scr) PPMO (Scr-1), using as indicator the multidrug resistant *E. coli* AIS070834. Viable cells were counted in 24-h cultures with antibiotic or PPMO alone, and in combinations where synergy was apparent (FIG. 14B, FIG. 14D, FIG. 14F). The free peptide (RXR)$_4$XB was also tested for synergy with the antibiotics, although by itself had an unmeasurable MIC (data not shown). Error bars indicate standard deviation. N=2 for all experiments.

(FIG. 15A) MIC of ampicillin with blaT-(RXR)$_4$XB (PPMO#66). (FIG. 15B) MIC of chloramphemicol with cmlA-(RXR)$_4$XB (PPMO#67). N=3.

DETAILED DESCRIPTION

I. Definitions

Figure 1C:
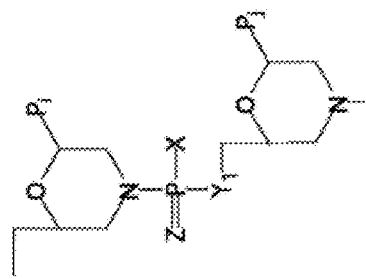
FIGS. 1B-E show the repeating subunit segment of exemplary morpholino oligomers, designated B through E.
Figure 1E:
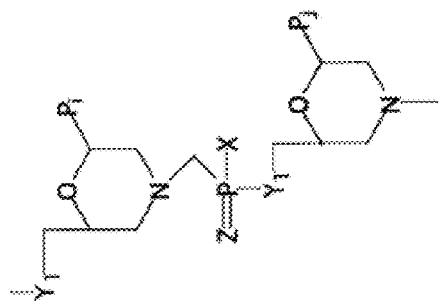
Figure 1B:
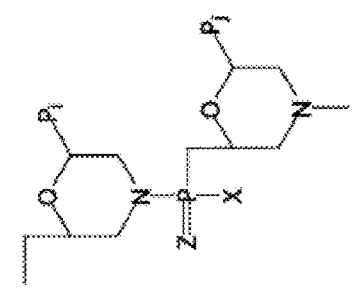
Figure 1D:
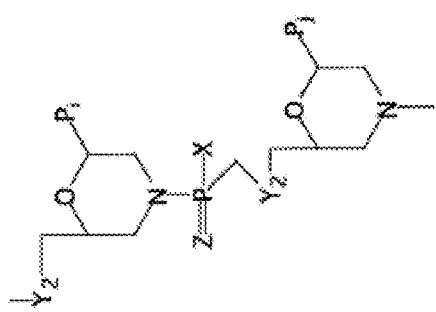

Unless defined otherwise, all technical and scientific terms used herein have the same meaning as commonly understood by those of ordinary skill in the art. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligomers described herein into a cell by methods routine in the art, e.g., transfection (e.g., liposome, calcium-phosphate, polyethyleneimine), electroporation (e.g., nucleofection), microinjection), transformation, and administration.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". In some aspects, the peptides have the capability of inducing cell penetration within about or at least about 30%, 40%, 50%, 60%, 70%, 80%, 90%, or 100% of cells of a given population and/or allow macromolecular translocation to or within multiple tissues in vivo upon systemic administration. Particular examples of CPPs include "arginine-rich peptides." CPPs are well-known in the art and are disclosed, for example, in U.S. Application No. 2010/0016215 and International Patent Application Publication Nos. WO 2004/097017, WO 2009/005793, and WO 2012/150960, all of which are incorporated by reference in their entirety.

"An electron pair" refers to a valence pair of electrons that are not bonded or shared with other atoms.

"Homology" refers to the percentage number of amino acids that are identical or constitute conservative substitutions. Homology may be determined using sequence comparison programs such as GAP (Deveraux et al., 1984, Nucleic Acids Research 12, 387-395) or BLAST. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide" or "isolated oligomer," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and ranges between and above 1), e.g., 1.5, 1.6, 1.7. 1.8) the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in bacterial cell growth, reductions in the minimum inhibitory concentration (MIC) of an antimicrobial agent, and others. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers and ranges in between.

As used herein, an "antisense oligomer," "oligomer," or "oligomer" refers to a linear sequence of nucleotides, or nucleotide analogs, which allows the nucleobase to hybridize to a target sequence in an RNA by Watson-Crick base pairing, to form an oligomer:RNA heteroduplex within the target sequence. The terms "antisense oligomer," "antisense oligomer," "oligomer," and "compound" may be used interchangeably to refer to an oligomer. The cyclic subunits may be based on ribose or another pentose sugar or, in certain embodiments, a morpholino group (see description of morpholino oligomers below).

The term "oligomer," "oligomer," or "antisense oligomer" also encompasses an oligomer having one or more additional moieties conjugated to the oligomer, e.g., at its 3'- or 5'-end, such as a polyethylene glycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

A "nuclease-resistant" oligomers refers to one whose backbone is substantially resistant to nuclease cleavage, in non-hybridized or hybridized form; by common extracellular and intracellular nucleases in the body or in a bacterial cell (for example, by exonucleases such as 3'-exonucleases, endonucleases, RNase H); that is, the oligomer shows little or no nuclease cleavage under normal nuclease conditions to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2,6-diaminopurine; 5-methyl cytosine; C5-propynyl-modified pyrimidines; 9-(aminoethoxy)phenoxazine (G-clamp) and the like.

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

An oligomer "specifically hybridizes" to a target sequence if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

As used herein, "sufficient length" includes an antisense oligomer that is complementary to at least about 8, more typically about 8-10, 8-11, 8-12, 8-13, 8-14, 8-15, 8-16, 8-17, 8-18, 8-19, 8-20, 8-30, 8-40, or 10-11, 10-12, 10-13, 10-14, 10-15, 10-16, 10-17, 10-18, 10-19, 10-20, 10-30, 10-40 (including all integers and ranges in between) contiguous or non-contiguous nucleobases in a region of a bacterial mRNA target sequence. An antisense oligomer of sufficient length has at least a minimal number of nucleotides to be capable of specifically hybridizing to a region of the bacterial mRNA target. Preferably an oligomer of sufficient length is from 8 to 30 nucleotides in length, for example, about 10-20 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

A "subject" or a "subject in need thereof" includes a mammalian subject such as a human subject.

The terms "TEG," "EG3," or "triethylene glycol tail" refer to triethylene glycol moieties conjugated to the oligomer, e.g., at its 3'- or 5'-end. For example, in some embodiments, "TEG" includes, for example, wherein T of the compound of formula (I), (II), or (III) is of the formula:

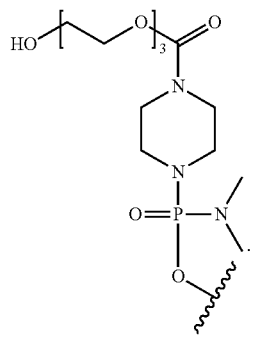

The term "pip-PDA" refers to a 5' terminal piperazine-phosphorodiamidate moiety that connects a G group, where the G group comprises a cell-penetrating peptide (CPP) and linker moiety further discussed below, to the 5'end of the oligomer by way of an amide bond between the G group linker and the piperazinyl nitrogen. For example, in some embodiments, "pip-PDA" includes wherein T of the compound of formula (I) or (II) is of the formula:

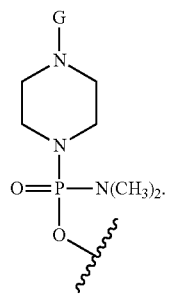

The term "target sequence" refers to a portion of the target RNA, for example, a bacterial mRNA, against which the antisense oligomer is directed, that is, the sequence to which the oligomer will hybridize by Watson-Crick base pairing of a complementary sequence. In certain embodiments, the target sequence may be a contiguous region of the translation initiation region of a bacterial gene.

The term "targeting sequence" or "antisense targeting sequence" refers to the sequence in an oligomer that is complementary or substantially complementary to the target sequence in the RNA, e.g., the bacterial mRNA. The entire sequence, or only a portion, of the antisense compound may be complementary to the target sequence. For example, in an oligomer of about 10-30 bases, about 6, 7, 8, 9, 10, 11, 12, 13, 14, 15, 16, 17, 18, 19, 20, 21, 22, 23, 24, 25, 26, 27, 28, or 29 of the bases may be targeting sequences that are complementary to the target region. Typically, the targeting sequence is formed of contiguous bases, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Bacterial Targeting Sequences

Certain embodiments relate to antisense oligomers, and related compositions and methods, which are of sufficient length and complementarity to specifically hybridize to a bacterial mRNA target sequence that encodes a gene in a biochemical pathway and/or cellular process. General examples include: cell division, global gene regulatory mechanisms, fatty acid biosynthesis, ribosomal proteins, DNA replication, transcription, translation initiation, lipopolysaccharide biosynthesis, peptidoglycan biosynthesis, nucleic acid biosynthesis, intermediary metabolism, and antibiotic resistance. Particular examples of genes in biochemical pathways and cellular processes include: rpsi and rpmB (ribosomal proteins); lpxC, waaC, waaG, waaA, waaF, lpxA, and lpxB (lipopolysaccharide biosynthesis); murA (formerly known as murZ), mraY, murC, murB, murE, murF, and murG (peptidoglycan biosynthesis); fabG, acpP, accA, accB, and fabZ (fatty acid biosynthesis); adk (cellular energy homeostasis); infA (transcription antitermination and/or protein synthesis); ftsZ (cell division); rpoD (RNA synthesis); aroC (aromatic compound biosynthesis). Examples of antibiotic resistance genes include blaT, cml, and adeA. In some embodiments, the mRNA target sequence that encodes the gene is from *Acinetobacter*, e.g., *Acinetobacter baumannii*. In some embodiments, the mRNA target sequence that encodes the gene is from *Escherichia*, e.g., *E. coli*.

In some embodiments, the bacterial target is a gene or protein that is associated with biosynthesis of fatty acids. General examples of proteins associated with fatty acid biosynthesis include: acyl carrier protein (ACP), such as AcpP, that plays an essential role in stabilizing and shuttling the intermediate fatty acid chain to each of the enzymes in the fatty acid synthase complex; acyl carrier protein synthase (AcpS), an enzyme that transfers the 4'-phosphopantetheine prosthetic group to apo-ACP to form the functional holo-ACP; acetyl-CoA carboxylase, an enzyme composed of four proteins that catalyzes the conversion of acetyl-CoA to malonyl-CoA in the first committed step of fatty acid biosynthesis: AccA (carboxyltransferase alpha subunit catalyzing the transfer of the carboxyl group from biotin to acetyl-CoA to form malonyl-CoA), AccB (biotin carboxyl carrier protein, BCCP, carrying the biotin prosthetic group covalently attached to a lysine residue proximal to the carboxyl terminus), AccC (biotin carboxylase catalyzing the carboxylation of protein bound biotin with bicarbonate), AccD (carboxyltransferase beta subunit catalyzing the transfer of the carboxyl group from biotin to acetyl-CoA to form malonyl-CoA); fatty acid biosynthesis (Fab) enzymes, such as FabA, FabI, FabF, FabB, FabD, FabH, FabG and FabZ, that each catalyze either elongation or tailoring steps on the growing fatty acid chain. Particular examples of genes associated with fatty acid biosynthesis include acpP and the carboxyltransferase alpha subunit accA. An exemplary translational start codon region sequence of the acyl carrier protein acpP gene is provided in Table 1 below.

Specific embodiment therefore relate to antisense oligomers, and related compositions and methods, which are of sufficient length and complementarity to specifically hybridize to an mRNA target sequence of a bacterial acpP gene, which encodes an acyl carrier protein (ACP). In some embodiments, the acpP gene is from *Acinetobacter*, e.g., *Acinetobacter baumannii*. In some embodiments, the acpP gene is from *Escherichia*, e.g., *E. coli*.

The bacterial cell wall peptidoglycan is an essential cellular component involved in the maintenance of shape and protection from osmotic shock lysis. The *Escherichia coli* peptidoglycan is assembled from a basic building block composed of N-acetylglucosamine (GlcNAc) and N-acetylmuramic acid with an attached pentapeptide. In some embodiments, the bacterial target is a gene or protein that is associated with peptidoglycan biosynthesis. A particular example of a gene associated with peptidoglycan biosynthesis include murA (formerly known as murZ), which encodes a UDP-N-acetylglucosamine 1-carboxyvinyltransferase, which catalyzes the first committed step of peptidoglycan biosynthesis. The enzyme catalyzes the transfer of enolpyruvate from phosphoenolpyruvate to the 3-OH of UDP-N-acetylglucosamine.

The ribosome is crucial for translation of mRNA molecules into proteins. In some embodiments, the bacterial target is a gene or protein that is associated with ribosomal proteins. A particular example of a gene associated with ribosomal proteins is rpmB, a 50S ribosomal protein L28 essential for ribosome assembly and translation.

In some embodiments, the bacterial target is a gene or protein that is associated with cellular energy homeostasis. A particular example of a gene associated with cellular energy homeostasis includes an adenylate kinase (adk) gene, which encodes a phosphotransferase enzyme that catalyzes the interconversion of adenine nucleotides.

In some embodiments, the bacterial target is a gene or protein that is associated with transcription antitermination and/or protein biosynthesis. A particular example of a gene associated with transcription antitermination and/or protein biosynthesis includes translation initiation factor IF1. IF1, encoded by infA, is a protein containing an S1-like domain that may play a role in binding and melting nucleic acid secondary structure and transcription antitermination. Other functions may also include increasing the rate of 70S ribosome dissociation and subunit association and involvement in the fidelity of translation initiation through stimulation of other translation initiation factor activities, such as IF2 and IF3.

In some embodiments, the bacterial target is a gene or protein that is associated with cell division. A particular example of a gene associated with cell division includes a ftsZ gene, which encodes a protein that assembles into a ring at the future site of the septum of bacterial cell division. This is a prokaryotic homologue to the eukaryotic protein tubulin.

In some embodiments, the bacterial target is a gene or protein that is associated with RNA synthesis. A particular example of a gene associated with RNA synthesis includes an rpoD gene, which encodes a sigma D (sigma 70) factor of RNA polymerase that allows binding of the polymerase to gene promoters and is important for transcribing most genes in growing cells. Genes recognized by this sigma factor have promoter consensus sequences centered at 10 and 35 nucleotides before the start of transcription.

The biosynthesis of aromatic compounds is important for the growth and survival of bacterial cells. The shikimate pathway is a biosynthetic route in microorganisms that lead to the synthesis of chorismic acid, a central precursor for other aromatic compounds. In some embodiments, the bacterial target is a gene or protein that is associated with aromatic compound biosynthesis. A particular example of a gene associated with aromatic compound biosynthesis includes an aroC gene, which encodes chorismate synthase (5-enolpyruvylshikimate-3-phosphate phospholyase), the final enzyme in the shikimate pathway that catalyzes the conversion of 5-enolpyruvylshikimate-3-phosphate to chorismic acid.

In some embodiments, the gene or protein is associated with resistance of the bacteria to at least one antimicrobial agent, i.e., an antibiotic resistance gene. General examples of antibiotic resistance genes include beta-lactamases, which can enzymatically deactivate certain antimicrobial agents, and proteins that increase the permeability or active efflux (pumping-out) of an antimicrobial agent. Particular examples of antibiotic resistance genes include TEM beta-lactamase (blaT), chloramphenicol resistance gene (cml), and resistance-nodulation-cell division (RND)-type multi-drug efflux pump subunit AdeA (adeA).

In certain embodiments, the target sequence contains all or a portion (e.g., 1 or 2 nucleotides) of a translational start codon of the bacterial mRNA. In some embodiments, the target sequence contains a sequence that is about or within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 bases upstream or downstream of a translational start codon of the bacterial mRNA target sequence, including common and alternative start codons (e.g., AUG, GUG, UUG, AUU, CUG). For example, in particular embodiments, the 5'-end of the target sequence is the adenine, uracil, or guanine nucleotide (respectively) in an AUG start codon of the bacterial mRNA. In some embodiments, the 5'-end of the target sequence is the guanine, uracil, or guanine nucleotide (respectively) in a GUG start codon of the bacterial mRNA. In some embodiments, the 5'-end of the target sequence is the uracil, uracil, or guanine nucleotide (respectively) in a UUG start codon of the bacterial mRNA. In some embodiments, the 5'-end or 3-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 downstream of the last (third) nucleotide of a translational start codon of the bacterial mRNA. In some embodiments, the 5'-end or 3-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 upstream of the first nucleotide of a translational start codon of the bacterial mRNA.

The target sequences of exemplary target genes from *Acinetobacter baumannii* and *E. coli* are provided in Table 1 below.

TABLE 1

Exemplary Target Sequences
Table 1A: Exemplary Antibiotic
Resistance Target Sequences

| Description | Sequence* | SEQ ID NO: |
|---|---|---|
| *E. coli* acpP Acyl carrier protein (ACP) | AAAGCGAGTTTTGATAGG AAATTTAAGAGT<u>ATG</u>AGC ACTATCGAAGAACGCGTT AAGAAA | 69 |
| *A. baumannii* acpP Acyl carrier protein (ACP) | TTTTAAAAATTTTTATAT TCAATTAAACTA<u>GT</u>GGCA AATCAAACGCCACAAGCA <u>ATG</u>AGGAGAATTCCTGTG AGCGATATCGAACAACGC | 70 |

*The thymines (T) can be uracils (U), and vice versa

Thus, in certain embodiments, antisense targeting sequences are designed to hybridize to a region of one or more of the target sequences listed in Table 1 (e.g., SEQ ID NO: 69 or 70) or a target gene described herein. Selected antisense targeting sequences can be made shorter, e.g., about 8, 9, 10, 11, 12, 13, 14, or 15 bases, or longer, e.g., about 20, 30, or 40 bases, and include a small number of mismatches, as long as the sequence is sufficiently complementary to reduce transcription or translation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligomers with the target RNA sequence may be as short as 8-9 bases, 8-10 bases, 8-11 bases, 8-12 bases, 10-11 bases, 10-12 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 10-15 bases is generally long enough to have a unique complementary sequence. In certain embodiments, a minimum length of complementary bases may be required to achieve the requisite binding Tm, as discussed herein.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths of less than about 30 or less than about 20 bases. Included are antisense oligomers that consist of about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to a target gene described herein, for example, a target sequence of Table 1 (e.g., SEQ ID NO: 69 or 70).

In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo, and reduce expression of the targeted mRNA. Hence, certain oligomers may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, for example, such that translation of the target RNA is reduced.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer.

Tables 2A-B below show exemplary targeting sequences (in a 5'-to-3' orientation) of the antisense oligomers described herein.

TABLE 2A

Exemplary Fatty Acid
Biosynthesis-Associated Targeting
Sequences

| Target Gene | Targeting Sequence (TS)* | TS SEQ ID NO: |
|---|---|---|
| acpP | CTTCGATAGTG | 1 |
| acpP | ATATCGCTCAC | 2 |
| acpP | ATTCTCCTCAT | 3 |
| acpP | CACAGGAATTC | 4 |
| acpS | TTGCCATTAGC | 5 |
| acp-E | CTGTAGTGATTTCACCA | 6 |
| fabA | TTATCTACCAT | 7 |
| fabB | GCACGTTTCAT | 8 |
| fabI | AGAAACCCAT | 9 |
| gapA | TTGATAGTCAT | 10 |
| accA | GCTTTTTTCAT | 11 |

*The thymines (T) can be uracils (U), and vice versa; I is inosine.

TABLE 2B

Exemplary targeting sequences associated with other biochemical pathways and/or cellular processes

| Target Gene | Targeting Sequence (TS)* | TS SEQ ID NO: |
|---|---|---|
| murA | ATCCATTTAGT | 12 |
| murA | CATTTAGTTTG | 13 |
| murA | AATTTATCCAT | 14 |
| murA | AAATTTATCCA | 15 |
| rpmB | ACTCGGGACAT | 16 |
| rpmB | CTATTCTCCAA | 17 |
| rpmB | GGCAGACTCGG | 18 |
| rpmB | CTTAGACATGG | 19 |
| adk | ATGATACGCAT | 20 |
| infA | TCTTTGGCCAT | 21 |
| ftsZ | TCAAATGAGGC | 22 |
| ftsZ | AATGAGGCCAT | 23 |
| ftsZ | ATAGTTTCTCTCC | 24 |
| rpoD | TCATCTTTGCT | 25 |
| rpoD | TTTTGCTCCAT | 26 |
| aroC | TTCCCTGCCAT | 27 |
| aroC | TTTCCAGCCAT | 28 |
| murF | ACGCTAATCAT | 29 |
| lpxC | TGTTTGATCAT | 30 |
| kdtA | AATTCGAGCAT | 31 |
| boxA | TGTTAAAGAGC | 32 |
| rpoD-E | CTTGTAACCACACCA | 33 |
| pryC | GGTGCAGTCAT | 34 |
| pryA | GACTTAATCAA | 35 |
| lgt | CTACTGGTCAT | 36 |
| folA | CATTGAGATTT | 37 |
| infB | ACATCTGTCAT | 38 |
| nrdA | TTCTGATTCAT | 39 |
| nrdB | GTATATGCCAT | 40 |
| zipA | TCCTGCATCAT | 41 |
| coaA | ATATACCTCAT | 42 |
| gyrA-E | GTTACCCTGACCGACCA | 43 |
| gyrA-E | GTTACCCTGACCACCA | 44 |
| mrdA | TGTTTCATACG | 45 |
| lpxB | GGTTTGCCAAG | 46 |
| lpxC | TGTTTCACCAT | 47 |
| kdtA | TTTTTCGCCAA | 48 |
| boxA | CTCTTAATGAT | 49 |
| boxC | ATCCACACAAG | 50 |
| rpoD-E | TCCACCAAGTCACCA | 51 |
| pryC | AGAGTTCAAGG | 52 |
| carA | GGTGCTCAAAC | 53 |
| adeA | ATACTGTCCAA | 54 |
| blaT | CTCTTCCTTTT | 55 |
| cml | TCCTTCTGATT | 56 |

*The thymines (T) can be uracils (U), and vice versa; I is inosine.

Certain antisense oligomers thus comprise, consist, or consist essentially of a targeting sequence in Tables 2A-B (e.g., SEQ ID NOS: 1-56) or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of the targeting sequences in Tables 2A-B (e.g., SEQ ID NOS: 1-56). For non-contiguous portions, intervening nucleotides can be deleted or substituted with a different nucleotide, or intervening nucleotides can be added. Additional examples of variants include oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of the targeting sequences in Tables 2A-B (e.g., SEQ ID NOS: 1-56).

The activity of antisense oligomers and variants thereof can be assayed according to routine techniques in the art (see, e.g., the Examples).

III. Antisense Oligomer Compounds

The antisense oligomers typically comprises a base sequence of sufficient length and complementarity to specifically hybridize to a bacterial mRNA target sequence that encodes a protein associated with a biochemical pathway and/or cellular process, and thereby reduce expression (e.g., translation) of the protein. This requirement is optionally met when the oligomer compound has the ability to be actively taken up by bacterial cells, and once taken up, form a stable duplex (or heteroduplex) with the target mRNA, optionally with a Tm greater than about 40° C. or 45° C.

A. Antisense Oligomer Chemical Features

In certain embodiments, the backbone of the antisense oligomer is substantially uncharged, and is optionally recognized as a substrate for active or facilitated transport across a cell wall and/or cell membrane. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell. Exemplary antisense oligomer targeting sequences are listed in Tables 2A-B (supra).

In certain embodiments, the antisense oligomer is a morpholino-based oligomer, for example, a phosphorodiamidate morpholino oligomer (PMO). Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligomer.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholine ring structure.

In particular embodiments, the morpholino subunits are joined by phosphorous-containing intersubunit linkages in accordance with the structure:

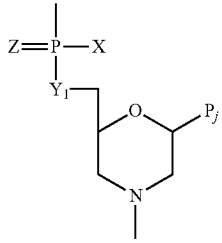

where $Y_1$=oxygen (O) or sulfur, nitrogen, or carbon; Z=oxygen or sulfur, preferably oxygen; Pj is a purine or pyrimidine base-pairing moiety effective to bind, by base-specific hydrogen bonding, to a base in a polynucleotide, and X is —NRR' where R and R' are the same or different and are either H or alkyl. In particular embodiments, X is —NRR', where R and R' are the same or different and are either H or methyl.

Figure 1A:
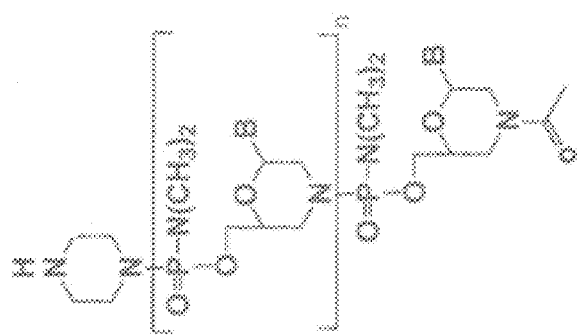
FIG. 1A shows an exemplary morpholino oligomer structure with a phosphorodiamidate linkage.

Also included are antisense oligomer that comprise a sequence of nucleotides of the formula in FIGS. 1A-1E. In FIG. 1A, B is a purine or pyrimidine base-pairing moiety effective to bind, by base-specific hydrogen bonding, to a base in a polynucleotide. $Y_1$ or $V_2$ may be oxygen, sulfur, nitrogen, or carbon, preferably oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy include 1-6 carbon atoms. The Z moieties may be sulfur or oxygen, and are preferably oxygen.

Accordingly, various embodiments of the disclosure include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a protein associated with a biochemical pathway and/or cellular process, or a protein associated with antibiotic resistance, as described herein. In some instances, the oligomer is conjugated to a cell-penetrating peptide (CPP).

In various aspects, an antisense oligomer of the disclosure includes a compound of formula (I)

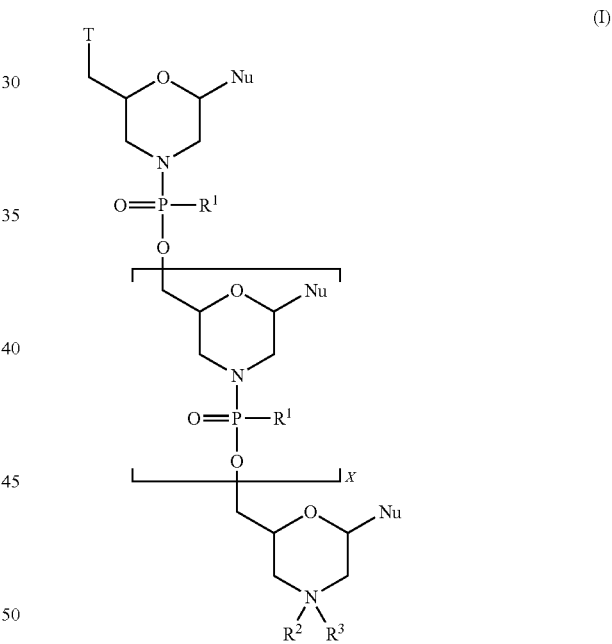

(I)

or a pharmaceutically acceptable salt thereof, where each Nu is a nucleobase which taken together forms a targeting sequence;

X is an integer from 9 to 38;

T is selected from OH and a moiety of the formula:

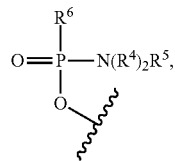

where each $R^4$ is independently $C_1$-$C_6$ alkyl, and $R^5$ is selected from an electron pair and H, and $R^6$ is selected from OH, —N($R^7$)CH$_2$C(O)NH$_2$, and a moiety of the formula:

where:
$R^7$ is selected from H and $C_1$-$C_6$ alkyl, and
$R^8$ is selected from G, —C(O)—$R^9$OH, acyl, trityl, and 4-methoxytrityl, where:
  $R^9$ is of the formula —(O-alkyl)$_y$- wherein y is an integer from 3 to 10 and each of
  the y alkyl groups is independently selected from $C_2$-$C_6$ alkyl;
each instance of $R^1$ is —N($R^{10}$)$_2$$R^{11}$ wherein each $R^{10}$ is independently $C_1$-$C_6$ alkyl, and $R^{11}$ is
selected from an electron pair and H;
$R^2$ is selected from H, G, acyl, trityl, 4-methoxytrityl, benzoyl, stearoyl, and a moiety of the formula:

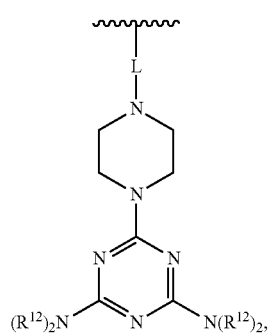

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{14}$)$_2$ wherein each $R^{14}$ is of the formula —(CH$_2$)$_6$NHC(=NH)NH$_2$; and
$R^3$ is selected from an electron pair, H, and $C_1$-$C_6$ alkyl, wherein G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, and —C(O)CH$_2$NH-CPP, or G is of the formula:

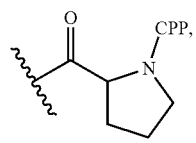

wherein the CPP is attached to the linker moiety by an amide bond at the CPP carboxy terminus, with the proviso that only one instance of G is present,
wherein the targeting sequence specifically hybridizes to a bacterial mRNA target sequence that encodes a protein associated with a biochemical pathway and/or cellular process.

In some embodiments, X is from 9 to 18. In certain embodiments, X is 9, 10, 11, 12, 13, 14, 15, 16, 17, 18, 19, 20, 21, 22, 23, 24, 25, 26, 27, 28, 29 or 30.

In certain embodiments, T is selected from:

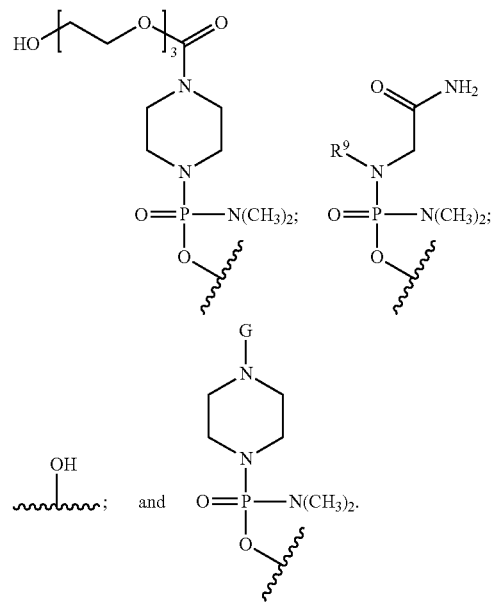

In some embodiments, $R^2$ is selected from H, G, acyl, trityl, 4-methoxytrityl, benzoyl, and stearoyl.

In various embodiments, T is selected from:

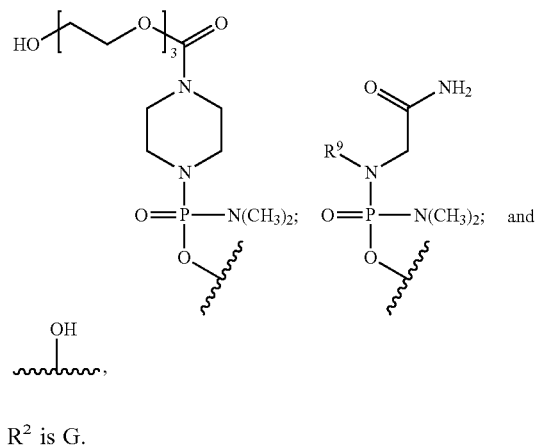

and $R^2$ is G.

In some embodiments, T is of the formula:

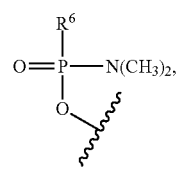

$R^6$ is of the formula:

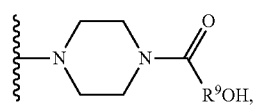

and $R^2$ is G.

In certain embodiments, T is of the formula:

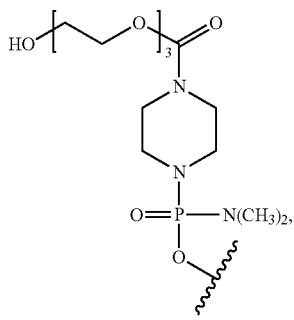

and R² is G.

In certain embodiments, T is of the formula:

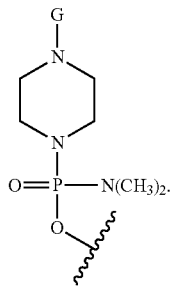

In some embodiments, R² is G or T is of the formula:

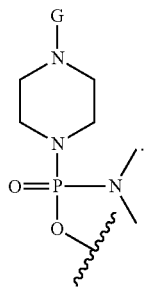

In some embodiments, R² is selected from H, acyl, trityl, 4-methoxytrityl, benzoyl, and stearoyl.

In various embodiments, R² is selected from H or G, and R³ is selected from an electron pair or H. In a particular embodiment, R² is G. In some embodiments, R² is H or acyl. In some embodiments, each R¹ is —N(CH$_3$)$_2$. In some embodiments, at least one instance of R¹ is —N(CH$_3$)$_2$. In certain embodiments, each instance of R¹ is —N(CH$_3$)$_2$.

In various embodiments of the disclosure, an antisense oligomer of the disclosure includes a compound of formula (II):

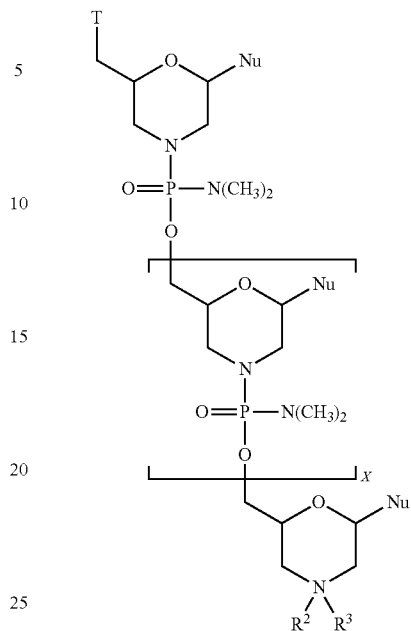

or a pharmaceutically acceptable salt thereof, where each Nu is a nucleobase which taken together forms a targeting sequence;

X is an integer from 9 to 28;

T is selected from:

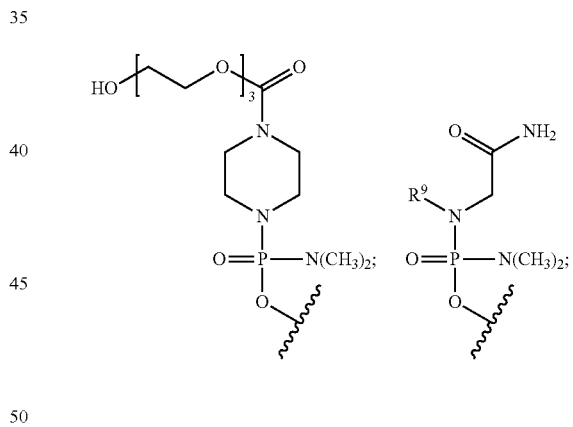

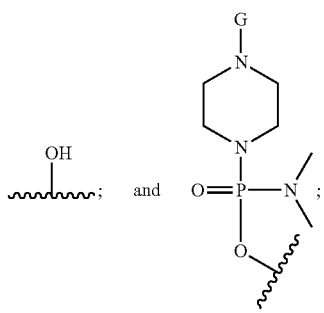

$R^2$ is selected from H, G, acyl, trityl, 4-methoxytrityl, benzoyl, and stearoyl; and $R^3$ is selected from an electron pair, H, and $C_1$-$C_6$ alkyl, wherein G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, and —C(O)CH$_2$NH-CPP, or G is of the formula:

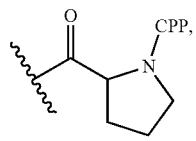

wherein the CPP is attached to the linker moiety by an amide bond at the CPP carboxy terminus, with the proviso that only one instance of G is present. In some embodiments, T is TEG as defined above, $R^2$ is G, and $R^3$ is an electron pair or H. In certain embodiments, $R^2$ is selected from H, acyl, trityl, 4-methoxytrityl, benzoyl, and stearoyl and T is of the formula:

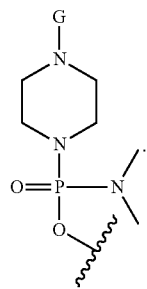

In some embodiments, $R^2$ is G or T is of the formula:

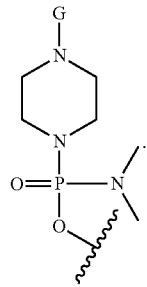

In various aspects, an antisense oligomer of the disclosure includes a compound of formula (III):

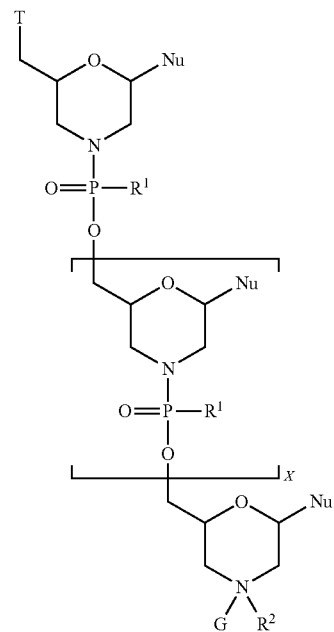

(III)

or a pharmaceutically acceptable salt thereof, where each Nu is a nucleobase which taken together forms a targeting sequence;

X is an integer from 9 to 28;

T is selected from:

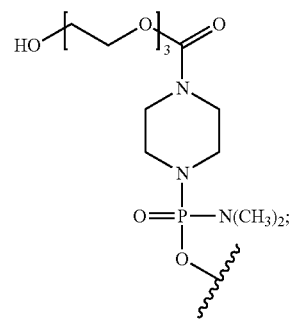

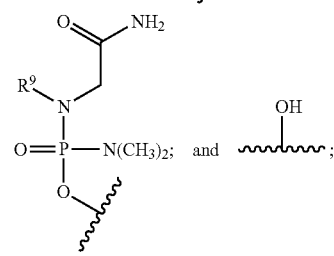

each instance of $R^1$ is —N(R$^{10}$)$_2$R$^{11}$ wherein each $R^{10}$ is independently $C_1$-$C_6$ alkyl, and $R^{11}$ is selected from an electron pair and H;

$R^2$ is selected from an electron pair, H, and $C_1$-$C_6$ alkyl; and

G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, and —C(O)CH₂NH-CPP, or G is of the formula:

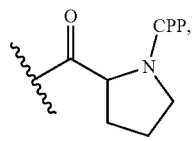

wherein the CPP is attached to the linker moiety by an amide bond at the CPP carboxy terminus. In some embodiments, at least one instance of $R^1$ is —N(CH₃)₂. In certain embodiments, each instance of $R^1$ is —N(CH₃)₂.

In various aspects, an antisense oligomer of the disclosure includes a compound of formula (IV):

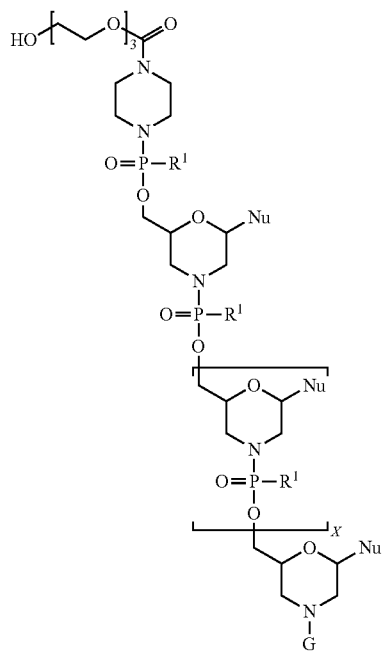

(IV)

or a pharmaceutically acceptable salt thereof, wherein:
X is an integer from 9 to 28;
each Nu is a nucleobase which taken together forms a targeting sequence;
each instance of $R^1$ is —N($R^{10}$)₂$R^{11}$ wherein each $R^{10}$ is independently $C_1$-$C_6$ alkyl, and $R^{11}$ is selected from an electron pair and H; and
G is a cell penetrating peptide ("CPP") and linker moiety selected from —C(O)(CH₂)₅NH-CPP, —C(O)(CH₂)₂NH-CPP, —C(O)(CH₂)₂NHC(O)(CH₂)₅NH-CPP,
and —C(O)CH₂NH-CPP, or G is of the formula:

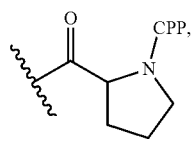

wherein the CPP is attached to the linker moiety by an amide bond at the CPP carboxy terminus. In some embodiments, at least one instance of $R^1$ is —N(CH₃)₂. In certain embodiments, each instance of $R^1$ is —N(CH₃)₂.

In various aspects, an antisense oligomer of the disclosure can be a compound of formula (V):

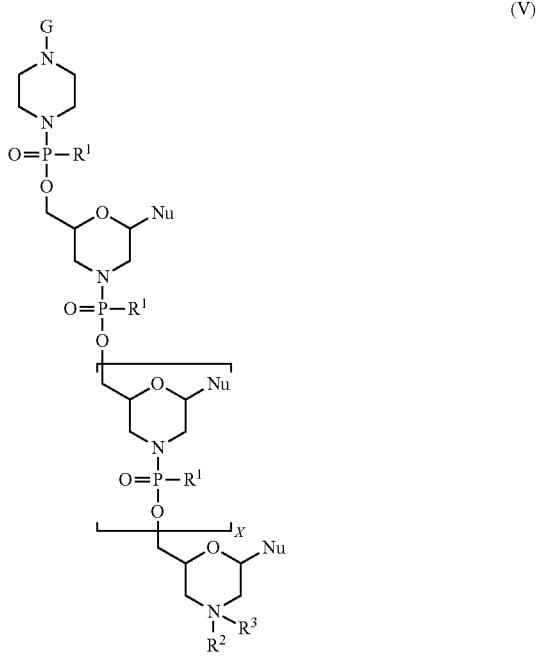

(V)

wherein:
X is an integer from 9 to 18;
each Nu is a nucleobase which taken together forms a targeting sequence;
each instance of $R^1$ is —N($R^{10}$)₂$R^{11}$ wherein each $R^{10}$ is independently $C_1$-$C_6$ alkyl, and $R^{11}$ is selected from an electron pair and H;
$R^2$ is selected from H, trityl, 4-methoxytrityl, acyl, benzoyl, and stearoyl; and
$R^3$ is selected from an electron pair, H, and $C_1$-$C_6$ alkyl,
wherein G is a cell penetrating peptide ("CPP") and linker moiety selected from —C(O)(CH₂)₅NH-CPP, —C(O)(CH₂)₂NH-CPP, —C(O)(CH₂)₂NHC(O)(CH₂)₅NH-CPP, and —C(O)CH₂NH-CPP, or G is of the formula:

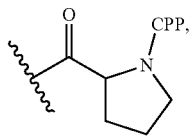

wherein the CPP is attached to the linker moiety by an amide bond at the CPP carboxy terminus. In some embodiments, at least one instance of $R^1$ is —N(CH₃)₂. In certain embodiments, each instance of $R^1$ is —N(CH₃)₂.

In various aspects, an antisense oligomer of the disclosure includes a compound of formula (VI):

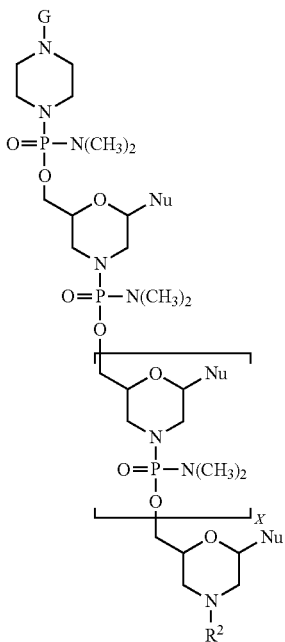

(VI)

or a pharmaceutically acceptable salt thereof, wherein:

X is an integer from 9 to 28;

each Nu is a nucleobase which taken together forms a targeting sequence;

$R^2$ is selected from H or acyl; and

G is a cell penetrating peptide ("CPP") and linker moiety selected from —C(O)(CH$_2$)$_5$NH-CPP, —C(O)(CH$_2$)$_2$NH-CPP, —C(O)(CH$_2$)$_2$NHC(O)(CH$_2$)$_5$NH-CPP, and —C(O)CH$_2$NH-CPP, or G is of the formula:

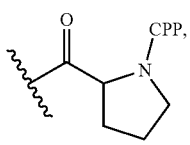

wherein the CPP is attached to the linker moiety by an amide bond at the CPP carboxy terminus.

The antisense oligomers can be prepared by stepwise solid-phase synthesis, employing methods known in the art and described in the references cited herein.

B. Cell-Penetrating Peptides

In certain embodiments, the antisense oligomer is conjugated to a cell-penetrating peptide (CPP). In some embodiments, the CPP is an arginine-rich peptide. By "arginine-rich carrier peptide" is meant that the CPP has at least 2, and preferably 2, 3, 4, 5, 6, 7, or 8 arginine residues, each optionally separated by one or more uncharged, hydrophobic residues, and optionally containing about 6-14 amino acid residues. FIGS. 1F-1H show exemplary chemical structures of CPP-PMO conjugates used in the Examples, including 5' and 3' PMO conjugates.

Exemplary CPPs are provided in Table C1 (SEQ ID NOS:57-68).

TABLE C1

Exemplary Cell-Penetrating Peptides

| Name | Sequence | SEQ ID NO: |
|---|---|---|
| (RXR)$_4$ | RXRRXRRXRRXR | 57 |
| (RFF)$_3$R | RFFRFFRFFR | 58 |
| (RXR)$_4$XB | RXRRXRRXRRXRXB | 59 |
| (RFF)$_3$RXB | RFFRFFRFFRXB | 60 |
| (RFR)$_4$ | RFRRFRRFRRFR | 61 |
| (RYR)$_4$ | RYRRYRRYRRYR | 62 |
| (RGR)$_4$ | RGRRGRRGRRGR | 63 |
| (RFR)$_4$XB | RFRRFRRFRRFRXB | 64 |
| (RYR)$_4$XB | RYRRYRRYRRYRXB | 65 |
| (RGR)$_4$XB | RGRRGRRGRRGRXB | 66 |
| (RFF)$_3$RXB | RFFRFFRFFRXB | 67 |
| (RFF)$_3$RG | RFFRFFRFFRG | 68 |

X is 6-aminohexanoic acid; B is β-alanine; F is phenylalanine; Y is tyrosine; G is glycine; R is arginine In some embodiments, the CPP is linked at its C-terminus to the 3'-end or the 5'-end of the oligomer via a 1, 2, 3, 4, or 5 amino acid linker.

CPPs, their synthesis, and methods of conjugating a CPP to an oligomer are detailed, for example, in International Patent Application Publication Nos. WO 2004/097017, WO 2009/005793, and WO 2012/150960, which are all incorporated by reference in their entirety.

In some embodiments, the CPP is linked at its C-terminus to the 3'-end or the 5'-end of the oligomer via a 1, 2, 3, 4, or 5 amino acid linker. In particular embodiments, including antisense oligomer compounds of formula (I)-(VI), the linkers can include: —C(O)(CH$_2$)$_5$NH-CPP (X linker), —C(O)(CH$_2$)$_2$NH-CPP (B linker), —C(O)(CH$_2$)$_2$NHC(O)(CH$_2$)$_5$NH-CPP (XB peptide linker), and —C(O)CH$_2$NH-CPP (G linker), or formula:

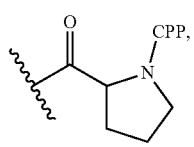

wherein the CPP is attached to the linker moiety by an amide bond at the CPP carboxy terminus. In some embodiments of the disclosure, including antisense oligomer compounds of formula (I)-(VI), G is selected from SEQ ID NOS: 59, 60, and 64-68. In various embodiments, including antisense oligomer compounds of formula (I)-(VI), the CPP is selected from SEQ ID NO: 57, and 61-63.

In some embodiments, including antisense oligomer compounds of formula (I)-(VI), the CPP is selected from:

35
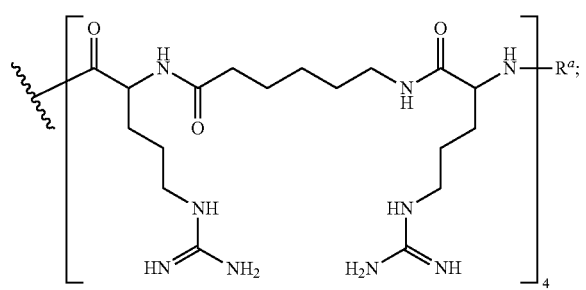
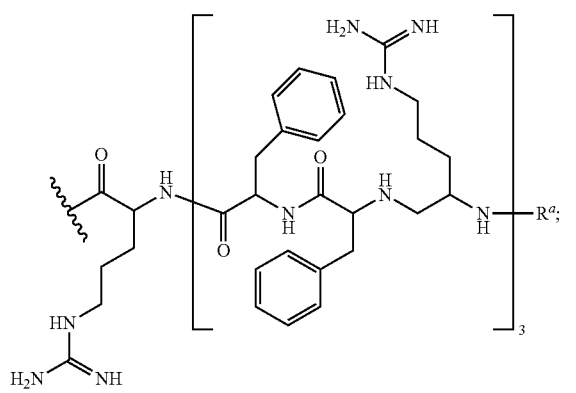
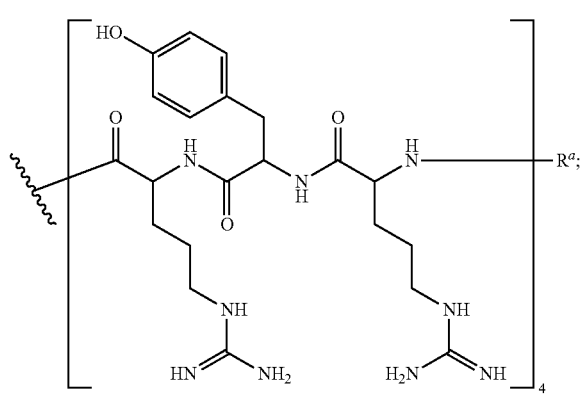
36
-continued
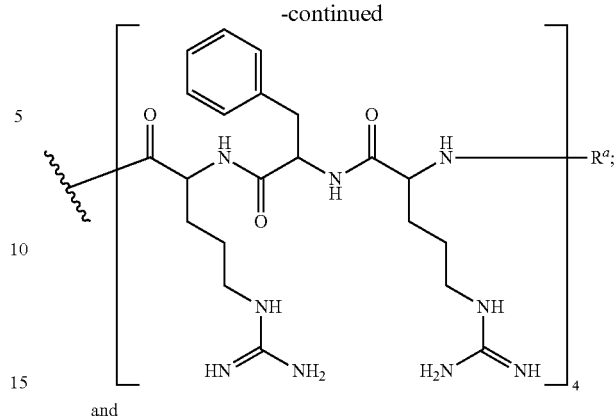
and
wherein $R^a$ is selected from H, acetyl, benzoyl, and stearoyl.
In some embodiments, including antisense oligomer compounds of formula (I)-(VI), G is selected from:
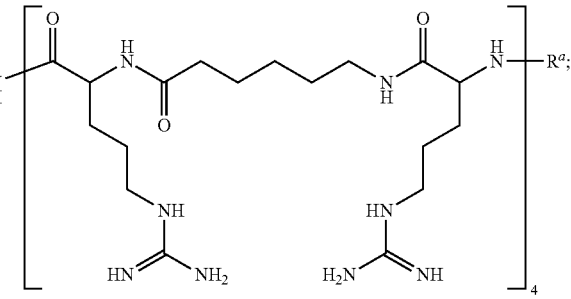

-continued
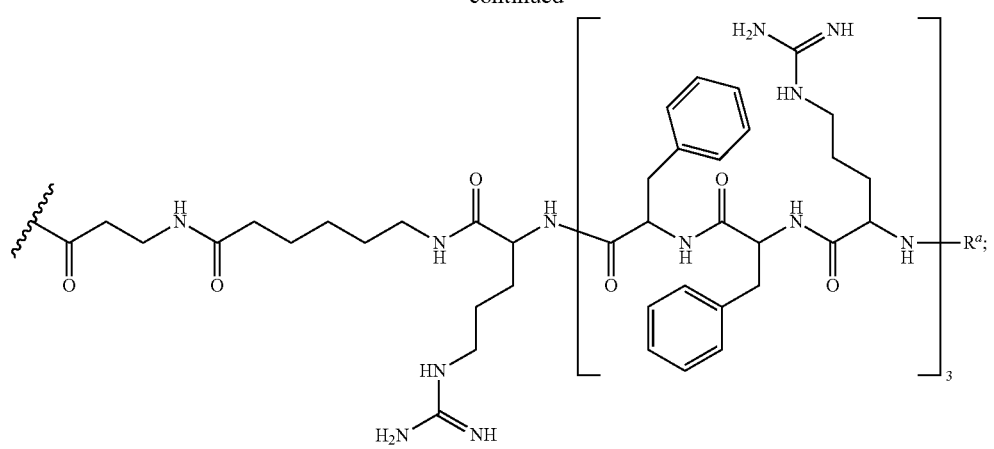
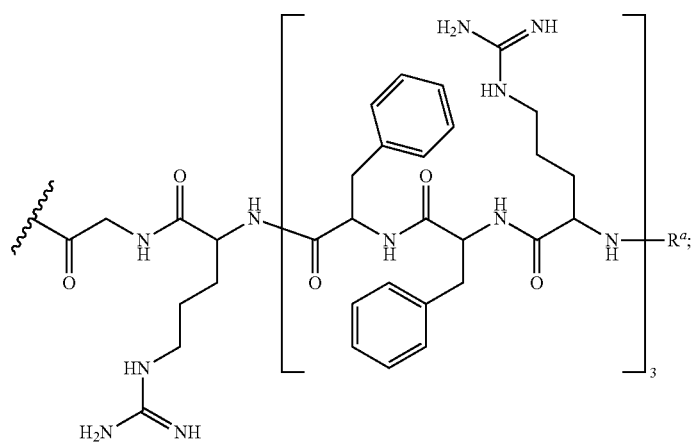
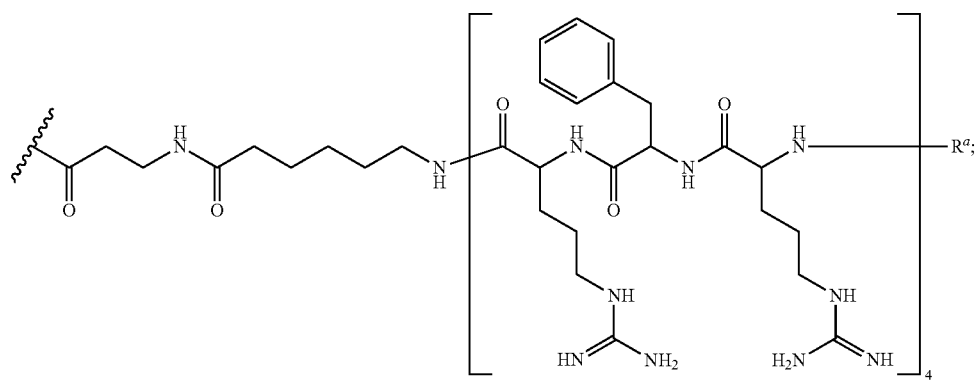
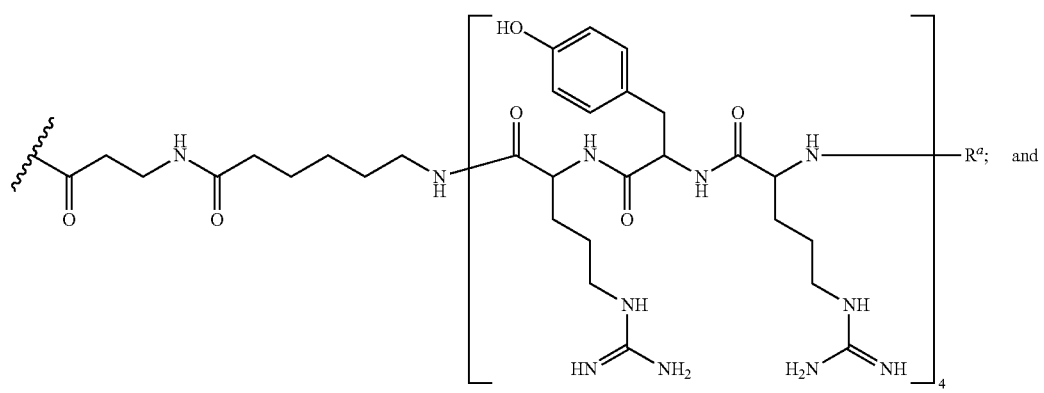

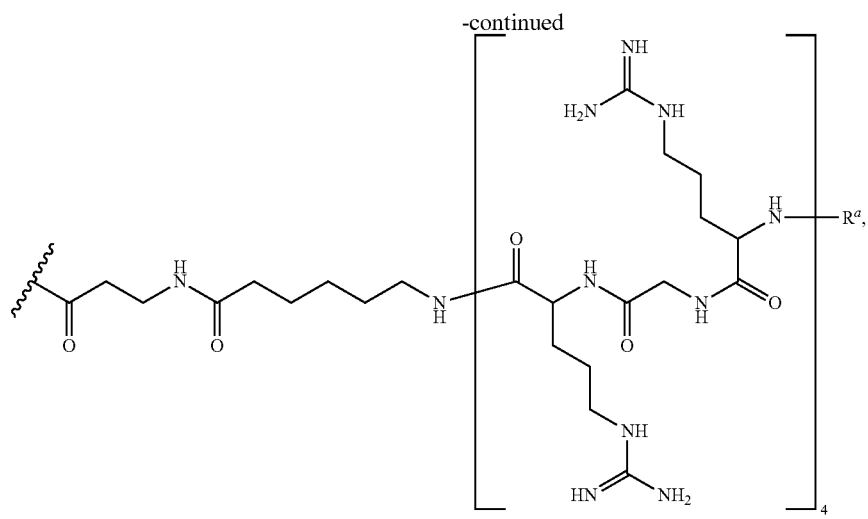
wherein $R^a$ is selected from H, acetyl, benzoyl, and stearoyl.
In various aspects, an antisense oligomer of the disclosure, or a pharmaceutically acceptable salt thereof, includes an antisense oligomer of the formula (VII) selected from:

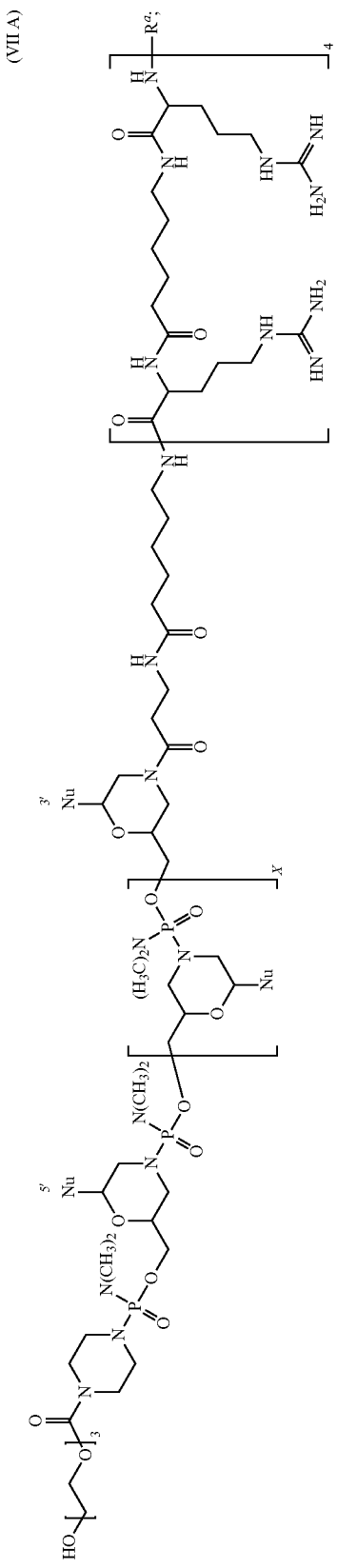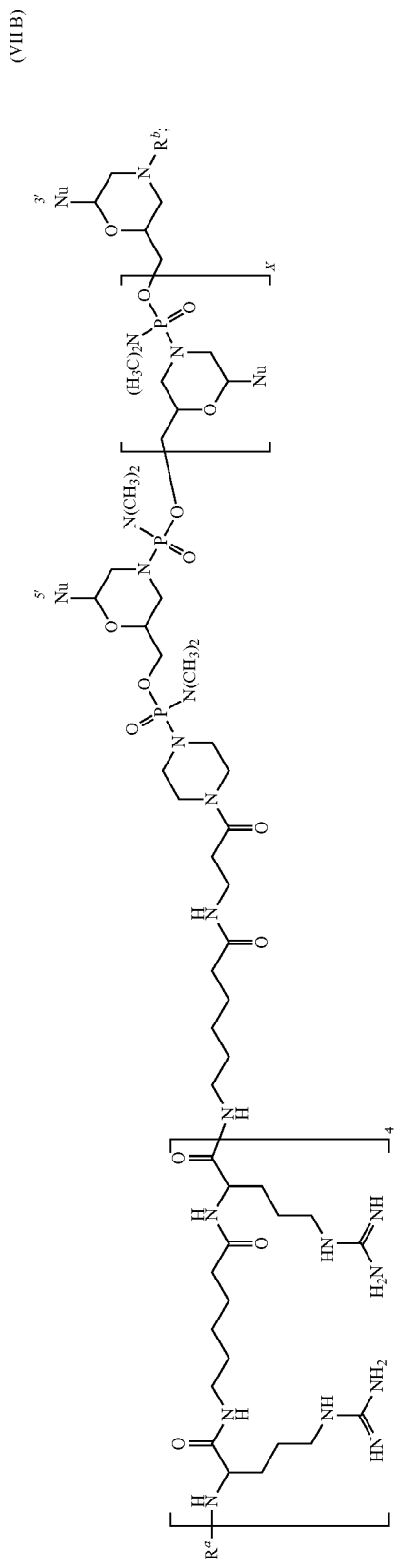

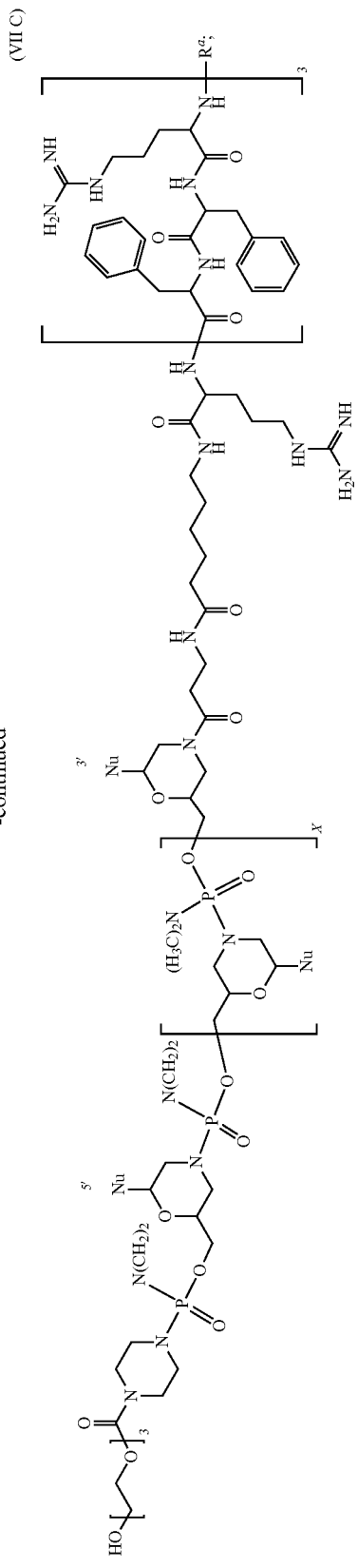
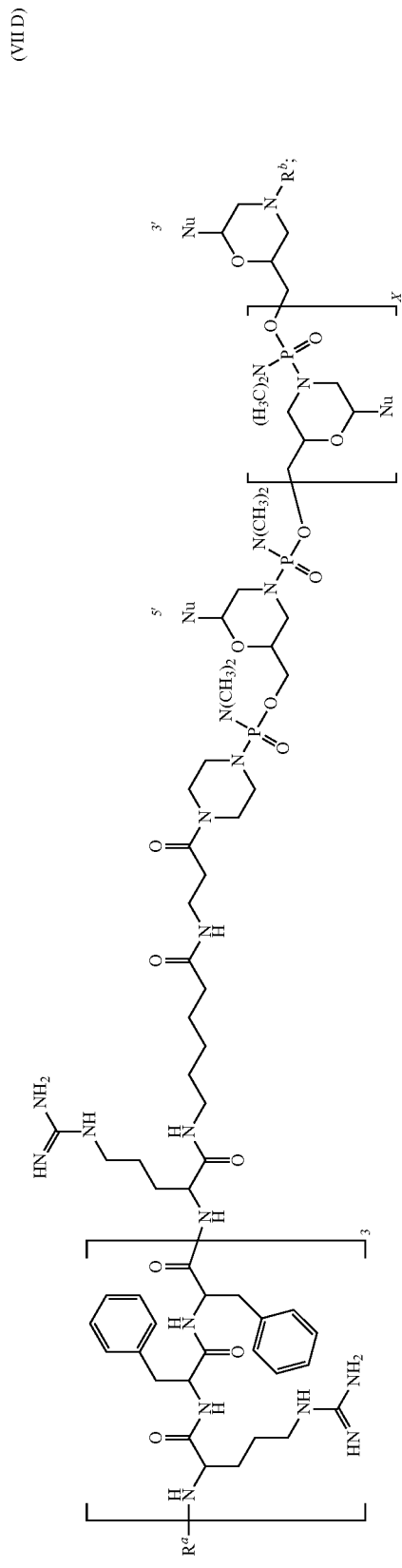

-continued
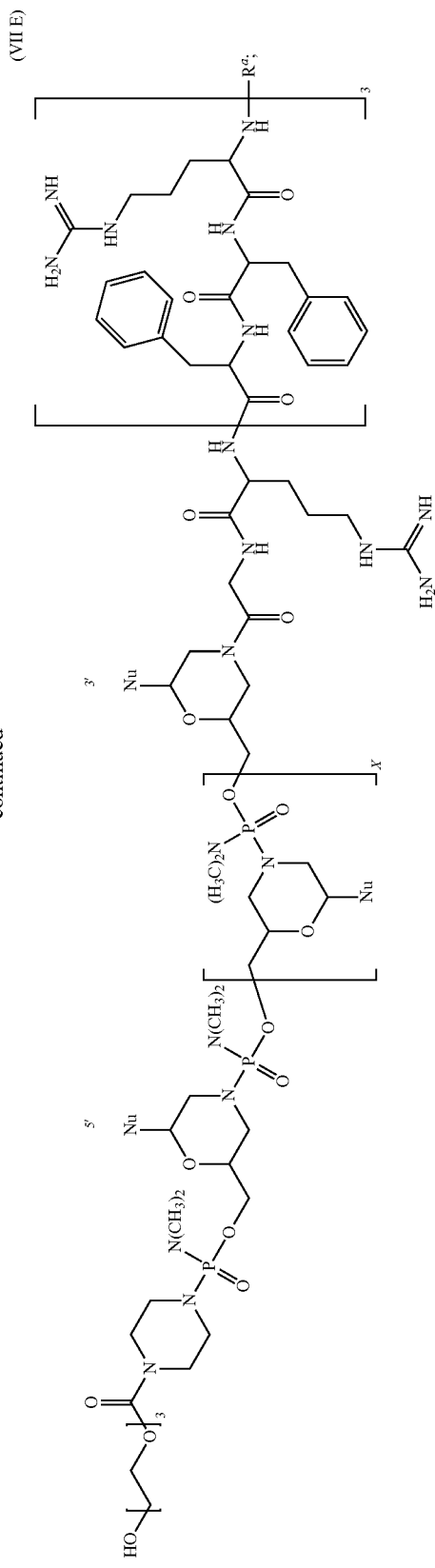
(VII E)
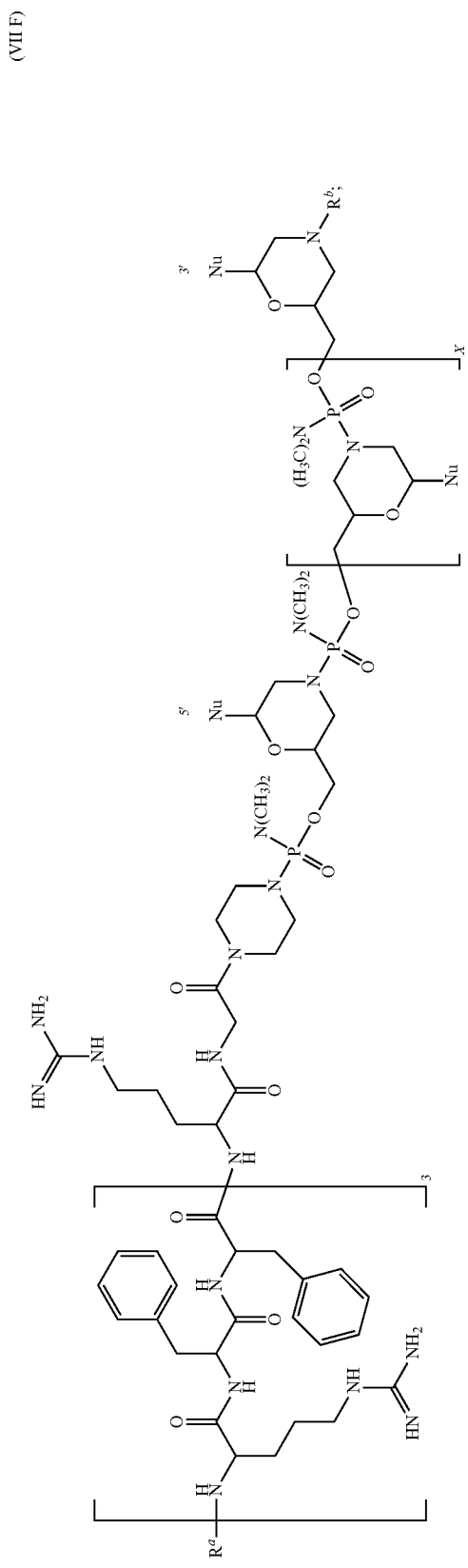
(VII F)

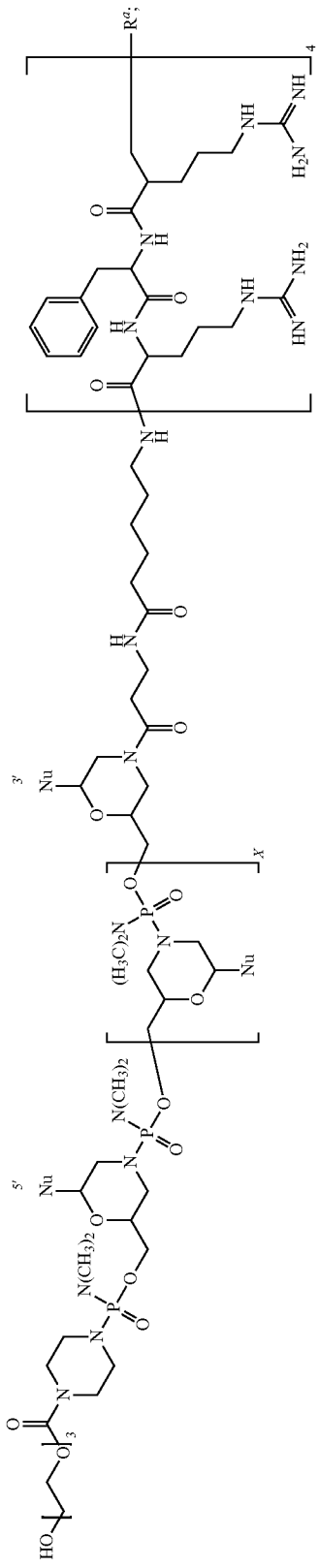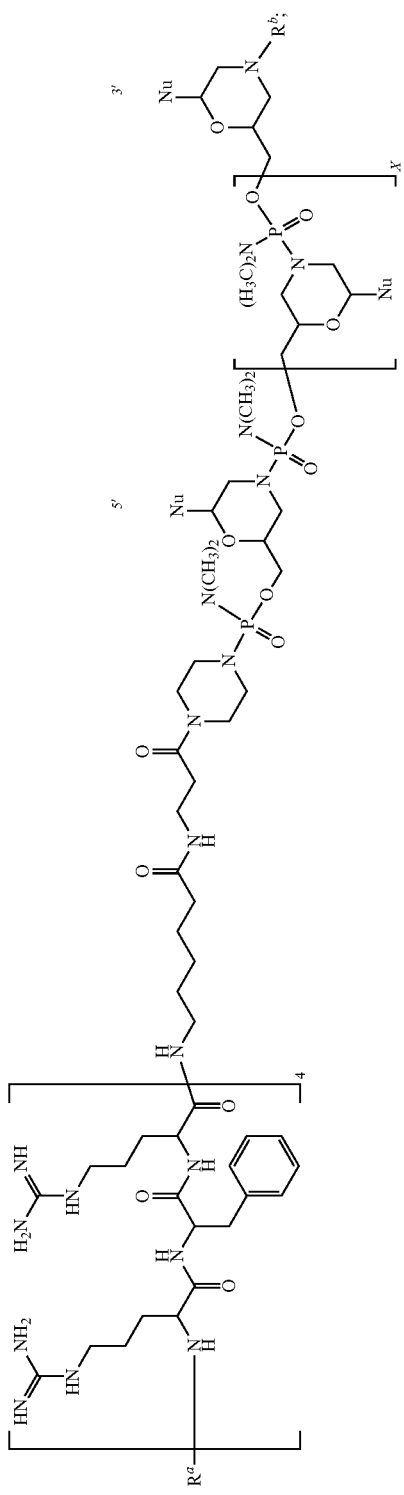

-continued
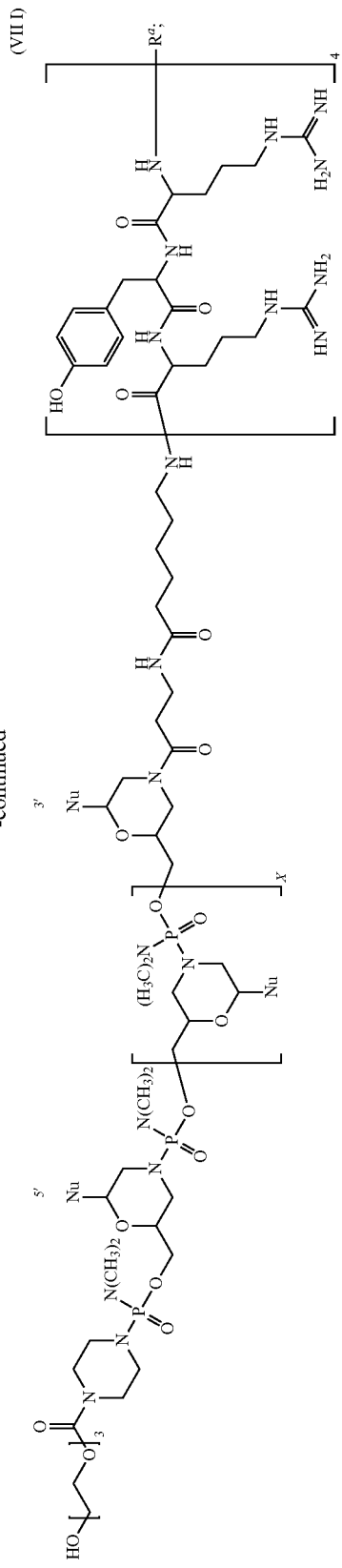
(VIII)
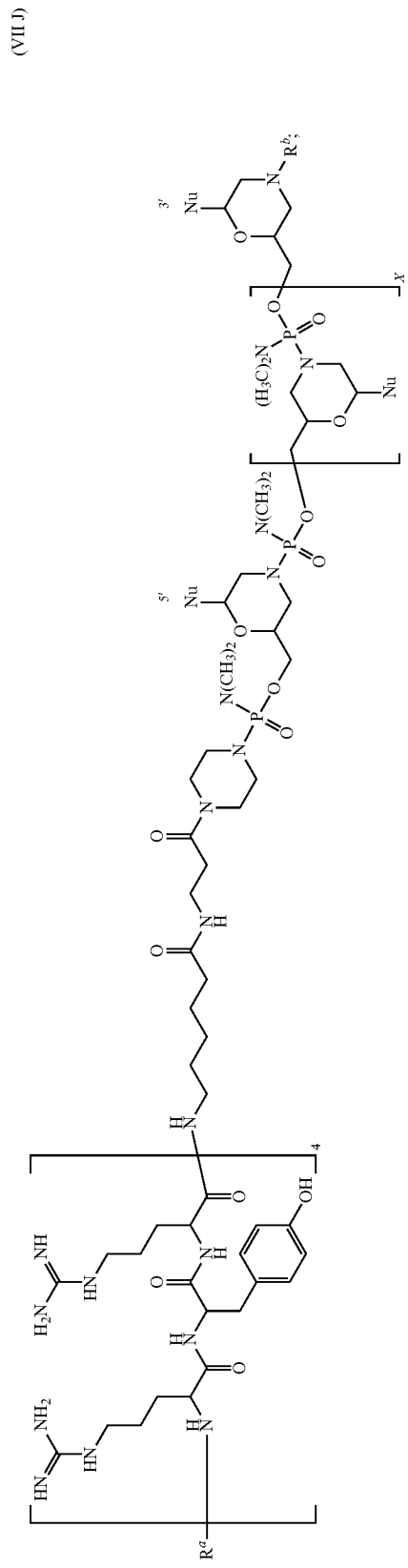
(VIIJ)

-continued
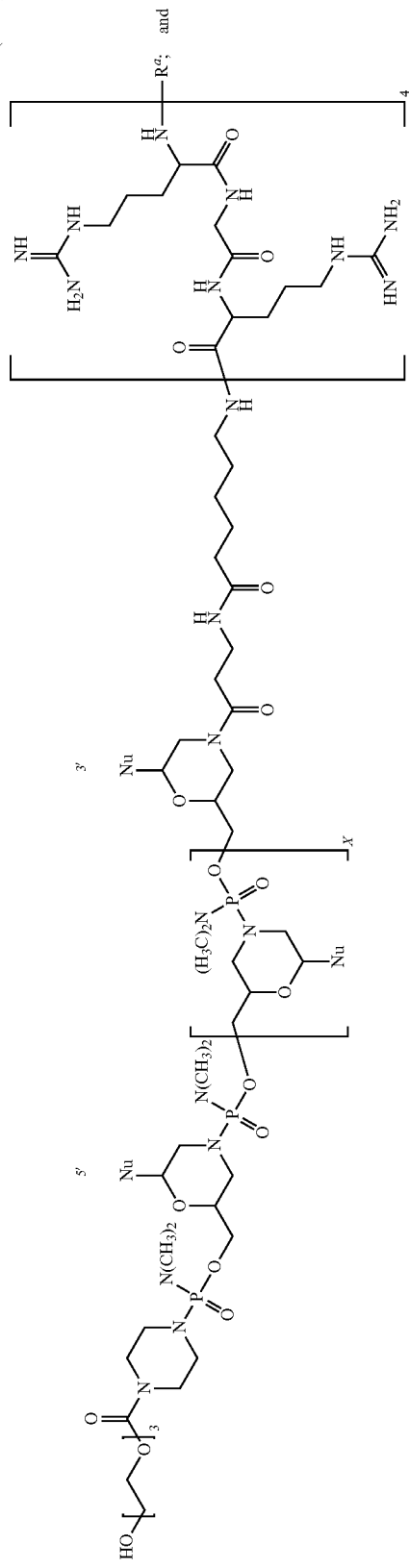
(VII K)
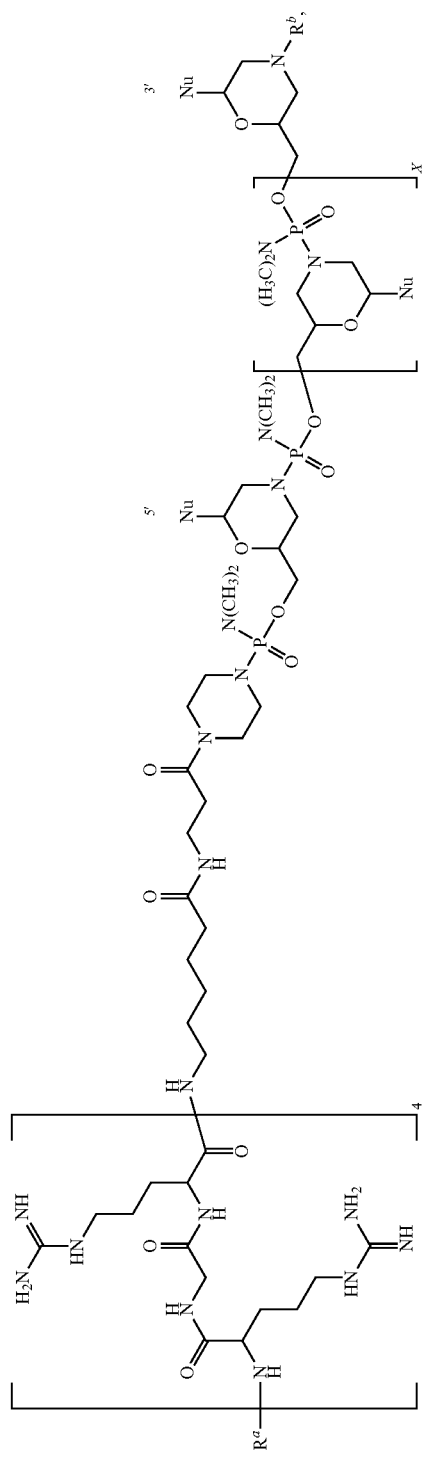
(VII L)

wherein X is an integer from 9 to 38, $R^a$ is selected from H, acetyl, benzoyl, and stearoyl, $R^b$ is selected from H, acetyl, benzoyl, stearoyl, trityl, and 4-methoxytrityl, and each Nu is a purine or pyrimidine base-pairing moiety which taken together form a targeting sequence described above.

C. Antisense Oligomer Targeting Sequences

In various embodiments of the antisense oligomers of the disclosure, including the antisense oligomer compounds of formulas (I)-(VII), the targeting sequence can specifically hybridizes to a bacterial mRNA target sequence that encodes a protein associated with a biochemical pathway and/or cellular process, or a protein associated with antibiotic resistance. In some embodiments, the target sequence comprises a translational start codon of the bacterial mRNA and/or a sequence within about 30 bases upstream or downstream of the translational start codon of the bacterial mRNA.

In various embodiments, the protein associated with a biochemical pathway and/or cellular process may be a fatty acid biosynthesis protein. In some embodiments, the fatty acid biosynthesis protein can be an acyl carrier protein. In certain embodiments, the acyl carrier protein may be AcpP. In some embodiments, the fatty acid biosynthesis protein may be a carboxyltransferase alpha subunit of an acetyl Coenzyme A carboxylase. In certain embodiments, the carboxyltransferase alpha subunit of an acetyl Coenzyme A carboxylase may be AccA. In some embodiments, the target sequence may be SEQ ID NOs: 1-11, wherein thymine bases (T) are optionally uracil bases (U). In certain embodiments, the targeting sequence comprises or consists of at least one of the targeting sequences in Table 2A (e.g., SEQ ID NOS: 1-11), comprises or consists of a fragment of at least 10 contiguous nucleotides of a targeting sequence in Table 2A (e.g., SEQ ID NOS: 1-11), or comprises or consists of a variant having at least 80% sequence identity to a targeting sequence in Table 2A (e.g., SEQ ID NOS: 1-11), wherein thymine bases (T) are optionally uracil bases (U).

In some embodiments, the protein associated with a biochemical pathway and/or cellular process may be a peptidoglycan biosynthesis protein. In certain embodiments, the peptidoglycan biosynthesis protein can be a UDP-N-acetylglucosamine 1-carboxyvinyltransferase. In some embodiments, the UDP-N-acetylglucosamine 1-carboxyvinyltransferase may be MurA.

In some embodiments, the protein associated with a biochemical pathway and/or cellular process is a ribosomal protein. In certain embodiments, the ribosomal protein is a 50S ribosomal protein L28. In some embodiments, the 50S ribosomal protein L28 is RpmB.

In various embodiments, the protein associated with a biochemical pathway and/or cellular process is a cellular energy homeostasis protein. In some embodiments, the cellular energy homeostasis protein is an adenylate kinase. In certain embodiments, the adenylate kinase is Adk.

In some embodiments, the protein associated with a biochemical pathway and/or cellular process is a protein biosynthesis protein. In certain embodiments, the protein biosynthesis protein is a translation initiation factor. In various embodiments, the translation initiation factor is InfA.

In some embodiments, the protein associated with a biochemical pathway and/or cellular process is a cell division protein. In certain embodiments, the cell division protein is a protein that assembles into a ring at the future site of the septum of bacterial cell division. For example, in some embodiments, the protein that assembles into a ring at the future site of the septum of bacterial cell division is FtsZ.

In certain embodiments, the protein associated with a biochemical pathway and/or cellular process is an RNA synthesis protein. In some embodiments, the RNA synthesis protein is a sigma D factor of RNA polymerase. For example, in certain embodiments, the sigma D factor of RNA polymerase is RpoD.

In some embodiments, the protein associated with a biochemical pathway and/or cellular process is an aromatic compound biosynthesis protein. In certain embodiments, the aromatic compound biosynthesis protein is a chorismate synthase (5-enolpyruvylshikimate-3-phosphate phospholyase). For example, in some embodiments, the chorismate synthase (5-enolpyruvylshikimate-3-phosphate phospholyase) is AroC.

In some embodiments, the protein associated with antibiotic resistance is selected from one or more of BlaT, Cml, and AdeA.

In some embodiments where the protein associated with a biochemical pathway and/or cellular process may be a peptidoglycan biosynthesis protein, a ribosomal protein, a cellular energy homeostasis protein, a protein biosynthesis protein, a cell division protein, an RNA synthesis protein, an aromatic compound biosynthesis protein, or antibiotic resistance, the targeting sequence comprises or consists of at least one of the targeting sequences set forth in Table 2B (e.g., SEQ ID NOS: 12-56), comprises or consists of a fragment of at least 10 contiguous nucleotides of a targeting sequence in Table 2B (e.g., SEQ ID NOS: 12-56), or comprises or consists of a variant having at least 80% sequence identity to a targeting sequence in Table 2B (e.g., SEQ ID NOS: 12-56), wherein thymine bases (T) are optionally uracil bases (U).

In certain embodiments, including the antisense oligomer compounds of formulas (I)-(VII), the targeting sequence is selected from:
a) SEQ ID NO: 1 (CTTCGATAGTG) wherein X is 9;
b) SEQ ID NO: 2 (ATATCGCTCAC) wherein X is 9;
c) SEQ ID NO: 3 (ATTCTCCTCAT) wherein X is 9;
d) SEQ ID NO: 4 (CACAGGAATTC) wherein X is 9;
e) SEQ ID NO: 5 (TTGCCATTAGC) wherein X is 9;
f) SEQ ID NO: 6 (CTGTAGTGATTTCACCA) wherein X is 15;
g) SEQ ID NO: 7 (TTATCTACCAT) wherein X is 9;
h) SEQ ID NO: 8 (GCACGTTTCAT) wherein X is 9;
i) SEQ ID NO: 9 (AGAAAACCCAT) wherein X is 9;
j) SEQ ID NO: 10 (TTGATAGTCAT) wherein X is 9; and
k) SEQ ID NO: 11 (GCTTTTTTCAT) wherein X is 9, wherein thymine bases (T) may be uracil bases (U).

In some embodiments, including the antisense oligomer compounds of formulas (I)-(VII), the targeting sequence is selected from:
a) SEQ ID NO: 12 (ATCCATTTAGT) wherein X is 9;
b) SEQ ID NO: 13 (CATTTAGTTTG) wherein X is 9;
c) SEQ ID NO: 14 (AATTTATCCAT) wherein X is 9;
d) SEQ ID NO: 15 (AAATTTATCCA) wherein X is 9;
e) SEQ ID NO: 16 (ACTCGGGACAT) wherein X is 9;
f) SEQ ID NO: 17 (CTATTCTCCAA) wherein X is 9;
g) SEQ ID NO: 18 (GGCAGACTCGG) wherein X is 9;
h) SEQ ID NO: 19 (CTTAGACATGG) wherein X is 9;
i) SEQ ID NO: 20 (ATGATACGCAT) wherein X is 9;
j) SEQ ID NO: 21 (TCTTTGGCCAT) wherein X is 9;
k) SEQ ID NO: 22 (TCAAATGAGGC) wherein X is 9;
l) SEQ ID NO: 23 (AATGAGGCCAT) wherein X is 9;
m) SEQ ID NO: 24 (ATAGTTTCTCTCC) wherein X is 11;
n) SEQ ID NO: 25 (TCATCTTTGCT) wherein X is 9;
o) SEQ ID NO: 26 (TTTTGCTCCAT) wherein X is 9;

p) SEQ ID NO: 27 (TTCCCTGCCAT) wherein X is 9;
q) SEQ ID NO: 28 (TTTCCAGCCAT) wherein X is 9;
r) SEQ ID NO: 29 (ACGCTAATCAT) wherein X is 9;
s) SEQ ID NO: 30 (TGTTTGATCAT) wherein X is 9;
t) SEQ ID NO: 31 (AATTCGAGCAT) wherein X is 9;
u) SEQ ID NO: 32 (TGTTAAAGAGC) wherein X is 9;
v) SEQ ID NO: 33 (CTTGTAACCACACCA) wherein X is 13;
w) SEQ ID NO: 34 (GGTGCAGTCAT) wherein X is 9;
x) SEQ ID NO: 35 (GACTTAATCAA) wherein X is 9;
y) SEQ ID NO: 36 (CTACTGGTCAT) wherein X is 9;
z) SEQ ID NO: 37 (CATTGAGATTT) wherein X is 9;
aa) SEQ ID NO: 38 (ACATCTGTCAT) wherein X is 9;
bb) SEQ ID NO: 39 (TTCTGATTCAT) wherein X is 9;
cc) SEQ ID NO: 40 (GTATATGCCAT) wherein X is 9;
dd) SEQ ID NO: 41 (TCCTGCATCAT) wherein X is 9;
ee) SEQ ID NO: 42 (ATATACCTCAT) wherein X is 9;
ff) SEQ ID NO: 43 (GTTACCCTGACCGACCA) wherein X is 15;
gg) SEQ ID NO: 44 (GTTACCCTGACCACCA) wherein X is 14;
hh) SEQ ID NO: 45 (TGTTTCATACG) wherein X is 9;
ii) SEQ ID NO: 46 (GGTTTGCCAAG) wherein X is 9;
jj) SEQ ID NO: 47 (TGTTTCACCAT) wherein X is 9;
kk) SEQ ID NO: 48 (IIIITCGCCAA) wherein X is 9;
ll) SEQ ID NO: 49 (CTCTTAATGAT) wherein X is 9;
mm) SEQ ID NO: 50 (ATCCACACAAG) wherein X is 9;
nn) SEQ ID NO: 51 (TCCACCAAGTCACCA) wherein X is 13;
oo) SEQ ID NO: 52 (AGAGTTCAAGG) wherein X is 9;
pp) SEQ ID NO: 53 (GGTGCTCAAAC) wherein X is 9, wherein thymine bases (T) may be uracil bases (U).

In some embodiments of the disclosure, including the antisense oligomer compounds of formulas (I)-(VII), the targeting sequence is selected from:
a) SEQ ID NO: 54 (ATACTGTCCAA);
b) SEQ ID NO: 55 (CTCTTCCTTTT); and
SEQ ID NO: 56 (TCCTTCTGATT),
wherein X is 9, and thymine bases (T) may be uracil bases (U).

D. Exemplary Antisense Oligomers

Exemplary antisense oligomers (AONs) of the disclosure include those described in Tables 3A-B below.

TABLE 3A

Exemplary Fatty Acid Biosynthesis-Associated Targeting Sequences AONs

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#1 | acpP | CTTCGATAGTG | 1 | (RXR)$_4$XB- | Acetyl | 59 |
| PPMO#2 | acpP | CTTCGATAGTG | 1 | TEG | (RXR)$_4$XB- | 59 |
| PPMO#3 | acpP | CTTCGATAGTG | 1 | (RFR)$_4$XB- | Acetyl | 59 |
| PPMO#4 | acpP | CTTCGATAGTG | 1 | TEG | (RYR)$_4$XB | 59 |
| PPMO#5 | acpP | CTTCGATAGTG | 1 | TEG | (RGR)$_4$XB- | 59 |
| PPMO#6 | acpP | ATATCGCTCAC | 2 | (RXR)$_4$XB- | Acetyl | 59 |
| PPMO#7 | acpP | ATATCGCTCAC | 2 | TEG | (RXR)$_4$XB- | 59 |
| PPMO#8 | acpP | ATTCTCCTCAT | 2 | (RXR)$_4$XB- | Acetyl | 59 |
| PPMO#9 | acpP | ATATCGCTCAC | 2 | (RFR)$_4$XB- | Acetyl | 64 |
| PPMO#10 | acpP | ATATCGCTCAC | 2 | (RGR)$_4$XB | Acetyl | 66 |
| PPMO#11 | acpP | ATATCGCTCAC | 2 | (RYR)$_4$XB- | Acetyl | 65 |
| PPMO#12 | acpP | ATATCGCTCAC | 2 | (RXR)$_4$XB- | H | 59 |
| PPMO#13 | acpP | ATTCTCCTCAT | 3 | TEG | (RFF)$_3$RXB- | 67 |
| PPMO#14 | acpP | CACAGGAATTC | 4 | TEG | (RXR)$_4$XB- | 59 |
| PPMO#15 | acpS | TTGCCATTAGC | 5 | TEG | (RXR)$_4$XB- | 59 |
| PPMO#16 | acp-E | CTGTAGTGATTCACCA | 6 | TEG | (RXR)$_4$XB- | 59 |
| PPMO#17 | fabA | TTATCTACCAT | 7 | TEG | (RXR)$_4$XB- | 59 |
| PPMO#18 | fabB | GCACGTTTCAT | 8 | TEG | (RXR)$_4$XB- | 59 |
| PPMO#19 | fabI | AGAAAACCCAT | 9 | TEG | (RXR)$_4$XB- | 59 |
| PPMO#20 | gapA | TTGATAGTCAT | 10 | TEG | (RXR)$_4$XB- | 59 |

TABLE 3A-continued

Exemplary Fatty Acid Biosynthesis-Associated Targeting Sequences AONs

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#21 | accA | GCTTTTTTCAT | 11 | (RXR)$_4$XB- | Acetyl | 59 |
| PPMO#68 | Scramble | TCT CAG ATG GT | 71 | TEG | (RXR)$_4$XB- | 59 |

The thymines (T) can be uracils (U), and vice versa; I is inosine;
** X is 6-aminohexanoic acid, B is beta-alanine, G is glycine, F is phenylalanine, Y is tyrosine, and TEG is defined above.
*** X is 6-aminohexanoic acid, B is beta-alanine, and a 5' CPP is linked through a pip-PDA moiety described above.

TABLE 3B

Exemplary AONS targeting other biochemical pathways, cellular processes, and/or antibiotic resistance

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#22 | murA | ATCCATTTAGT | 12 | TEG | (RXR)$_4$XB- | 59 |
| PPMO#23 | murA | CATTTAGTTTG | 13 | TEG | (RXR)$_4$XB- | 59 |
| PPMO#24 | murA | AATTTATCCAT | 14 | TEG | (RXR)$_4$XB- | 59 |
| PPMO#25 | murA | AAATTTATCCA | 15 | TEG | (RXR)$_4$XB- | 59 |
| PPMO#26 | rpmB | ACTCGGGACAT | 16 | TEG | (RXR)$_4$XB- | 59 |
| PPMO#27 | rpmB | CTATTCTCCAA | 17 | TEG | (RXR)$_4$XB- | 59 |
| PPMO#28 | rpmB | GGCAGACTCGG | 18 | TEG | (RXR)$_4$XB- | 59 |
| PPMO#29 | rpmB | CTTAGACATGG | 19 | TEG | (RXR)$_4$XB- | 59 |
| PPMO#30 | adk | ATGATACGCAT | 20 | TEG | (RXR)$_4$XB- | 59 |
| PPMO#31 | infA | TCTTTGGCCAT | 21 | TEG | (RXR)$_4$XB- | 59 |
| PPMO#32 | ftsZ | TCAAATGAGGC | 22 | (RXR)$_4$XB- | Acetyl | 59 |
| PPMO#33 | ftsZ | TCAAATGAGGC | 22 | TEG | (RXR)$_4$XB- | 59 |
| PPMO#34 | ftsZ | AATGAGGCCAT | 23 | TEG | (RXR)$_4$XB- | 59 |
| PPMO#35 | ftsZ | ATAGTTTCTCTCC | 24 | (RXR)$_4$XB- | Acetyl | 59 |
| PPMO#36 | rpoD | TCATCTTTGCT | 25 | TEG | (RXR)$_4$XB- | 59 |
| PPMO#37 | rpoD | TTTTGCTCCAT | 26 | TEG | (RXR)$_4$XB- | 59 |
| PPMO#38 | aroC | TTCCCTGCCAT | 27 | TEG | (RXR)$_4$XB- | 59 |
| PPMO#39 | aroC | TTTCCAGCCAT | 28 | TEG | (RXR)$_4$XB- | 59 |
| PPMO#40 | murF | ACGCTAATCAT | 29 | TEG | (RXR)$_4$XB- | 59 |
| PPMO#41 | lpxC | TGTTTGATCAT | 30 | TEG | (RXR)$_4$XB- | 59 |
| PPMO#42 | kdtA | AATTCGAGCAT | 31 | TEG | (RXR)$_4$XB- | 59 |
| PPMO#43 | boxA | TGTTAAAGAGC | 32 | TEG | (RXR)$_4$XB- | 59 |
| PPMO#44 | rpoD-E | CTTGTAACCACACCA | 33 | TEG | (RXR)$_4$XB- | 59 |
| PPMO#45 | pryC | GGTGCAGTCAT | 34 | TEG | (RXR)$_4$XB- | 59 |
| PPMO#46 | pryA | GACTTAATCAA | 35 | TEG | (RXR)$_4$XB- | 59 |

TABLE 3B-continued

Exemplary AONS targeting other biochemical pathways, cellular processes, and/or antibiotic resistance

| PMO Name | Target Gene | Targeting Sequence (TS)* | TS SEQ ID NO: | 5' Attachment *** | 3' Attachment ** | CPP SEQ ID NO. |
|---|---|---|---|---|---|---|
| PPMO#47 | lgt | CTACTGGTCAT | 36 | TEG | (RXR)₄XB- | 59 |
| PPMO#48 | folA | CATTGAGATTT | 37 | TEG | (RXR)₄XB- | 59 |
| PPMO#49 | infB | ACATCTGTCAT | 38 | TEG | (RXR)₄XB- | 59 |
| PPMO#50 | nrdA | TTCTGATTCAT | 39 | TEG | (RXR)₄XB- | 59 |
| PPMO#51 | nrdB | GTATATGCCAT | 40 | TEG | (RXR)₄XB- | 59 |
| PPMO#52 | zipA | TCCTGCATCAT | 41 | TEG | (RXR)₄XB- | 59 |
| PPMO#53 | coaA | ATATACCTCAT | 42 | TEG | (RXR)₄XB- | 59 |
| PPMO#54 | gyrA-E | GTTACCCTGACCGACCA | 43 | TEG | (RXR)₄XB- | 59 |
| PPMO#55 | gyrA-E | GTTACCCTGACCACCA | 44 | TEG | (RXR)₄XB- | 59 |
| PPMO#56 | mrdA | TGTTTCATACG | 45 | TEG | (RXR)₄XB- | 59 |
| PPMO#57 | lpxB | GGTTTGCCAAG | 46 | TEG | (RXR)₄XB- | 59 |
| PPMO#58 | lpxC | TGTTTCACCAT | 47 | TEG | (RXR)₄XB- | 59 |
| PPMO#59 | kdtA | TTTTTCGCCAA | 48 | TEG | (RXR)₄XB- | 59 |
| PPMO#60 | boxA | CTCTTAATGAT | 49 | TEG | (RXR)₄XB- | 59 |
| PPMO#61 | boxC | ATCCACACAAG | 50 | TEG | (RXR)₄XB- | 59 |
| PPMO#62 | rpoD-E | TCCACCAAGTCACCA | 51 | TEG | (RXR)₄XB- | 59 |
| PPMO#63 | pryC | AGAGTTCAAGG | 52 | TEG | (RXR)₄XB- | 59 |
| PPMO#64 | carA | GGTGCTCAAAC | 53 | TEG | (RXR)₄XB- | 59 |
| PPMO#65 | adeA | ATACTGTCCAA | 54 | TEG | (RXR)₄XB- | 59 |
| PPMO#66 | blaT | CTCTTCCTTTT | 55 | TEG | (RXR)₄XB- | 59 |
| PPMO#67 | cml | TCCTTCTGATT | 56 | TEG | (RXR)₄XB- | 59 |

The thymines (T) can be uracils (U), and vice versa; I is inosine;
** X is 6-aminohexanoic acid, B is beta-alanine, G is glycine, F is phenylalanine, Y is tyrosine, and TEG is defined above.
*** X is 6-aminohexanoic acid, B is beta-alanine, and a 5' CPP is linked through a pip-PDA moiety described above.

IV. Methods of Use and Formulations

Embodiments of the present disclosure include methods of using the antisense oligomers described herein to reduce the expression and activity of one or more bacterial proteins associated with biochemical pathways, cellular processes, and/or antibiotic resistance. Certain embodiments include methods of using the antisense oligomers to reduce replication, proliferation, or growth of a bacteria, for example, to treat a bacterial infection in a subject, either alone or in combination with one or more additional antimicrobial agents. In some instances, the antisense oligomers increase the susceptibility of the bacterium to one or more antimicrobial agents.

Also included are pharmaceutical compositions comprising the antisense oligomers, typically in combination with a pharmaceutically-acceptable carrier. Certain pharmaceutical compositions can further comprise one or more antimicrobial agents. The methods provided herein can be practiced in vitro or in vivo.

For example, certain embodiments include methods of treating a bacterial infection in a subject, comprising administering to a subject in need thereof (e.g., subject having or at risk for having a bacterial infection) an antisense oligomer or pharmaceutical composition described herein. Also included are methods of reducing replication of a bacteria, comprising contacting the bacterium with an antisense oligomer described herein.

In some embodiments, the bacterium is selected from the genus *Escherichia* and *Acinetobacter*.

*Escherichia* is a genus of Gram-negative, non-spore forming, facultatively anaerobic, rod-shaped bacteria from the family Enterobacteriaceae, and includes the species *Escherichia coli*, which is responsible for the vast majority of *Escherichia*-related pathogenesis.

*Acinetobacter* is a genus of Gram-negative bacteria belonging to the class of Gammaproteobacteria. Examples of clinically-relevant *Acinetobacter* complexes include the *Acinetobacter calcoaceticus-baumannii* complex (glucose-oxidizing non hemolytic), *Acinetobacter lwoffii* (glucose-negative non hemolytic), and *Acinetobacter haemolyticus* (hemolytic). Specific examples include *Acinetobacter baumannii*.

Thus, in some embodiments, the bacterium is any of the foregoing members of the genera *Escherichia* or *Acinetobacter*. In specific embodiments, the bacterium is *Escherichia coli* or *Acinetobacter baumannii*. In some embodiments, the bacterium is selected from one or more of the strains in Table E1.

In certain embodiments, the bacterium is a multi-drug resistance (MDR) strain of bacteria. Multiple drug resistance (MDR), multi-drug resistance or multiresistance is a condition enabling disease-causing microorganisms (bacteria, viruses, fungi or parasites) to resist distinct antimicrobials such as antibiotics, antifungal drugs, antiviral medications, antiparasitic drugs, and others. In particular embodiments, the bacterium is extensively-drug resistant (XDR) or pan-drug resistant (PDR). In some embodiments, the bacterium is an extended-spectrum β-lactamase (ESBLs) producing Gram-negative bacteria, or a multi-drug-resistant gram negative rod (MDR GNR) MDRGN bacteria. In specific embodiments, the bacterium is MDR *Escherichia*, for example, MDR *Escherichia coli*, or MDR *Acinetobacter*, for example, MDR *Acinetobacter baumannii*.

Examples of genes associated with biochemical pathways and/or cellular processes include fatty acid biosynthesis genes (and their related proteins) such as acpP, accA, acpS, and/or fab genes, for example, from *Escherichia* or *Acinetobacter*. In particular embodiments, the bacterium comprises or expresses the acpP gene, which encodes an acyl carrier protein. In particular embodiments, the bacterium comprises or expresses the accA gene, which encodes a carboxyltransferase alpha subunit of an acetyl Coenzyme A carboxylase. In specific embodiments, the bacterium that comprises or expresses one or more genes associated with fatty acid biosynthesis is a *Escherichia* species, for example, *Escherichia coli*. In specific embodiments, the bacterium that comprises or expresses one or more genes associated with fatty acid biosynthesis is an *Acinetobacter* species. In some of these and related embodiments, the subject in need thereof is immunocompromised and has an underlying lung disease, such as cystic fibrosis (CF) or chronic granulomatous disease (CGD).

Examples of genes associated with biochemical pathways and/or cellular processes include peptidoglycan biosynthesis genes (and their related proteins), for example, from *Escherichia* species. In particular embodiments, the bacterium comprises or expresses the murA gene, which encodes a UDP-N-acetylglucosamine 1-carboxyvinyltransferase. In specific embodiments, the bacterium that comprises or expresses one or more genes associated with peptidoglycan biosynthesis is *Escherichia coli*.

Examples of genes associated with biochemical pathways and/or cellular processes include ribosomal protein genes (and their related proteins), for example, from *Escherichia* species or *Acinetobacter* spp. In particular embodiments, the bacterium comprises or expresses the rpmB gene, which encodes a 50S ribosomal protein L28. In specific embodiments, the bacterium that comprises or expresses one or more genes associated with ribosomal protein genes is *Escherichia coli* or *Acinetobacter* spp.

Examples of genes associated with biochemical pathways and/or cellular processes include cellular homeostasis genes (and their related proteins), for example, from *Escherichia* species. In particular embodiments, the bacterium comprises or expresses the adk gene, which encodes an adenylate kinase. In specific embodiments, the bacterium that comprises or expresses one or more genes associated with cellular homeostasis genes is *Escherichia coli*.

Examples of genes associated with biochemical pathways and/or cellular processes include protein biosynthesis genes (and their related proteins), for example, from *Escherichia* species. In particular embodiments, the bacterium comprises or expresses the infA gene, which encodes a translation initiation factor. In specific embodiments, the bacterium that comprises or expresses one or more genes associated with protein biosynthesis genes is *Escherichia coli*.

Examples of genes associated with biochemical pathways and/or cellular processes include cell division genes (and their related proteins), for example, from *Acinetobacter* spp. In particular embodiments, the bacterium comprises or expresses the ftsZ gene, which encodes a protein that assembles into a ring at the future site of the septum of bacterial cell division. In specific embodiments, the bacterium that comprises or expresses one or more genes associated with cell division genes is *Acinetobacter* spp.

Examples of genes associated with biochemical pathways and/or cellular processes include RNA synthesis genes (and their related proteins), for example, from *Acinetobacter* spp. In particular embodiments, the bacterium comprises or expresses the rpoD gene, which encodes a sigma D factor of RNA polymerase. In specific embodiments, the bacterium that comprises or expresses one or more genes associated with RNA synthesis genes is *Acinetobacter* spp.

Examples of genes associated with biochemical pathways and/or cellular processes include aromatic compound biosynthesis genes (and their related proteins), for example, from *Acinetobacter* spp. In particular embodiments, the bacterium comprises or expresses the aroC gene, which encodes a chorismate synthase (5-enolpyruvylshikimate-3-phosphate phospholyase). In specific embodiments, the bacterium that comprises or expresses one or more genes associated with aromatic compound biosynthesis genes is *Acinetobacter* spp.

In some embodiments, the bacteria or bacterium comprises (e.g., encodes) one or more antibiotic resistance genes. General examples of antibiotic resistance genes (and their related proteins) include beta-lactamases, which can enzymatically deactivate certain antimicrobial agents, and genes/proteins which increase the permeability or active efflux (pumping out) of an antimicrobial agent. Particular examples of antibiotic resistance genes include TEM beta-lactamase (blaT), chloramphenicol resistance gene cml and resistance-nodulation-cell division (RND)-type multidrug efflux pump subunit AdeA (adeA). In specific embodiments, the bacterium is *Escherichia coli* or *Acinetobacter* spp., which comprises or expresses at least one antibiotic resistance gene selected from blaT, cml and adeA.

In some embodiments, the antisense oligomer reduces expression of the gene(s) associated with biochemical pathways, cellular processes, and/or antibiotic resistance in the bacteria or bacterium. For instance, in some embodiments, the antisense oligomer reduces expression by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligomer, scrambled oligomer, prior to contacting with the oligomer), or by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to a control. In some embodiments, the antisense oligomer reduces expression of one or more of AcpP, AccA, MurA, RpmB, Adk, InfA, FtsZ, RpoD, AroC, BlaT, Cml and/or AdeA and the bacterium is an *Acinetobacter* or *Escherichia* species which comprises or expresses one or more of AcpP, AccA, MurA, RpmB, Adk, InfA, FtsZ, RpoD, AroC, BlaT, Cml and/or AdeA. Gene or protein expression can be measured in vitro (see, e.g., the Examples) or in vivo.

In some embodiments, the antisense oligomer reduces or inhibits the growth of the bacteria or bacterium. For instance, in some embodiments, the antisense oligomer reduces growth of the bacteria or bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligomer, scrambled oligomer, prior to contacting with the oligomer), or by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to a control. Bacterial growth can be measured in vitro (see, e.g., the Examples) or in vivo. In particular embodiments, the antisense oligomer that reduces growth of the bacterium is targeted against a protein associated with a biochemical pathway and/or cellular process selected from one or more of AcpP, AccA, MurA, RpmB, Adk, InfA, FtsZ, RpoD, AroC, BlaT, Cml and/or AdeA and the bacterium is an *Acinetobacter* or *Escherichia* species which comprises or expresses one or more of AcpP, AccA, MurA, RpmB, Adk, InfA, FtsZ, RpoD, AroC, BlaT, Cml and/or AdeA. In some embodiments, as described herein, the antisense oligomer is employed in combination with one or more antimicrobial agents, for example, to synergistically reduce the growth of the bacteria or bacterium.

In some embodiments, the antisense oligomer reduces beta-lactamase (e.g., carbapenemase) activity in the periplasm of the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In some embodiments, the antisense oligomer reduces meropenemase enzymatic activity in the periplasm of the bacterium. In particular embodiments, the antisense oligomer that reduces beta-lactamase activity is targeted against blaT, and the bacterium is an *Acinetobacter*, or *Escherichia* species, for example, *Escherichia coli* or *Acinetobacter baumannii* which comprises or expresses BlaT. These are exemplary bacterial species and it is expected that any bacterium expressing the blaT gene is susceptible to the compounds and methods described herein. Beta-lactamase activity can be measured according to routine techniques in the art.

In some embodiments, the methods are practiced in vivo, and comprise administering the antisense oligomer to a subject in need thereof, for example, a subject in need thereof that is infected or at risk for being infected by one or more of the bacteria described herein. The antisense oligomers described herein can thus be administered to subjects to treat (prophylactically or therapeutically) an infection by any of the bacteria described herein. In conjunction with such treatment, pharmacogenomics (e.g., the study of the relationship between an individual's genotype/phenotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal, and topical delivery. The appropriate route may be determined by one of skill in the art, as appropriate to the condition of the subject under treatment. Vascular or extravascular circulation, the blood or lymph system, and the cerebrospinal fluid are some non-limiting sites where the antisense oligomers may be introduced. Direct CNS delivery may be employed, for instance, intracerebral, intraventricular, or intrathecal administration may be used as routes of administration.

In certain embodiments, the antisense oligomers can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

The antisense oligomers described herein may also be delivered via an implantable device. Design of such a device is an art-recognized process, with, e.g., synthetic implant design described in, e.g., U.S. Pat. No. 6,969,400, the contents of which are incorporated by reference.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (see, e. g., Dokka and Rojanasakul, Advanced Drug Delivery Reviews 44:35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions The compounds (e.g., antisense oligomers, antimicrobial agents) described herein may generally be utilized as the free acid or free base. Alternatively, the compounds described herein may be used in the form of acid or base addition salts. Acid addition salts of the free amino compounds described herein may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers described herein. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In certain embodiments, the antisense oligomer is administered to a mammalian subject, e.g., human or domestic animal, exhibiting the symptoms of a bacterial infection (e.g., antibiotic resistance or MDR bacterial infection), in a suitable pharmaceutical carrier. In some aspects, the subject is a human subject, e.g., a patient diagnosed as having a bacterial infection. In particular embodiments, the antisense oligomer is contained in a pharmaceutically acceptable carrier, and is delivered orally. In some embodiments, the antisense oligomer is contained in a pharmaceutically acceptable carrier, and is delivered intravenously (i.v.).

In some embodiments, the antisense oligomer is administered in an amount and manner effective to result in a peak blood concentration of at least 200-400 nM antisense oligomer. Typically, one or more doses of antisense oligomer are administered, generally at regular intervals, for a period of about one to two weeks. Certain doses for oral administration are from about 1-1000 mg oligomer per 70 kg. In some cases, doses of greater than 1000 mg oligomer/patient may be necessary. For i.v. administration, some doses are from about 0.5 mg to 1000 mg oligomer per 70 kg. The antisense oligomer may be administered at regular intervals for a short time period, e.g., daily for two weeks or less. However, in some cases the antisense oligomer is administered intermittently over a longer period of time. Administration may be followed by, or concurrent with, administration of an antimicrobial (e.g., antibiotic) or other therapeutic treatment, as described herein. The treatment regimen may be adjusted (dose, frequency, route, etc.) as indicated, based on the results of immunoassays, other biochemical tests and physiological examination of the subject under treatment.

An effective in vivo treatment regimen using the antisense oligomers described herein may vary according to the duration, dose, frequency and route of administration, as well as the condition of the subject under treatment (i.e., prophylactic administration versus administration in response to localized or systemic infection). Accordingly, such in vivo therapy will often include monitoring by tests appropriate to the particular type of disorder or bacterial infection under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer described herein may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

V. Combination Therapies

Certain embodiments include combination therapies, for example, the administration of antisense oligomers in combination with antimicrobial agents such as antibiotics. Combination therapies can be employed, for example, to increase the sensitivity or susceptibility of a given bacteria to one or more antimicrobial agents, and thereby improve the therapeutic outcome (e.g., resolution of the infection). Likewise, certain combination therapies can be employed, for example, to reduce or reverse the resistance of a given bacteria to one or more antimicrobial agents. In particular embodiments, the antisense oligomer reduces the minimum inhibitory concentration (MIC) of an antibiotic against a given bacterium. In certain embodiments, the antisense oligomer and the antimicrobial agent display synergy in reducing bacterial growth and/or increasing bacterial cell-killing. Also included are pharmaceutical compositions, as described herein, which comprise an antisense oligomer and an antimicrobial agent such as antibiotic.

In some embodiments, the antisense oligomer and the antimicrobial agent are administered separately. In certain embodiments, the antisense oligomer and the antimicrobial agent are administered sequentially. In some embodiments, the antisense oligomer and the antimicrobial agent are administered concurrently, for example, as part of the same or different pharmaceutical composition.

Examples of antimicrobial agents (e.g., antibiotics) that can be administered in combination with an antisense oligomer include beta-lactam antibiotics such as carbapenems, penicillin and penicillin derivatives (or penams), ampicillin, chloramphenicol, cephalosporins (e.g., Cefacetrile (cephacetrile), Cefadroxil (cefadroxyl; Duricef), Cephalexin (cefalexin; Keflex), Cefaloglycin (cephaloglycin), Cefalonium (cephalonium), Cefaloridine (cephaloridine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, loracarbef (Lorabid); Cephamycins: cefbuperazone, cefmetazole (Zefazone), cefminox, cefotetan (Cefotan), cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Meezat, Fortum, Fortaz), latamoxef (moxalactam), Cefclidine, cefepime (Maxipime), cefluprenam, cefoselis, Cefozopran, Cefpirome (Cefrom), Cefquinome, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime), and monobactams (e.g., aztreonam, tigemonam, nocardin A, tabtoxin); aminoglycosides such as tobramycin, gentamicin, kanamycin a, amikacin, dibekacin, sisomicin, netilmicin, neomycin B, neomycin C, neomycin E (paromomycin), and streptomycin; tetracyclines such as tetracycline, chlortetracycline, oxytetracycline, demeclocycline, lymecycline, meclocycline, methacycline, minocycline, rolitetracycline, and doxycyline; sulfonamides such as sulfacetamide, sulfadiazine, sulfadimidine, sulfafurazole, sulfisomidine, sulfadoxine, sulfamethoxazole, sulfamoxole, sulfadimethoxine, sulfamethoxypyridazine, sulfametoxydiazine, sulfadoxine, and sulfametopyrazine; quinolones such as cinoxacin, nalidixic acid, oxolinic acid (Uroxin), piromidic acid (Panacid), pipemidic acid (Dolcol) rosoxacin (Eradacil), ciprofloxacin (Alcipro, Ciprobay, Cipro, Ciproxin, ultracipro), enoxacin (Enroxil, Penetrex), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin, Tavanic), pazufloxacin (Pasil, Pazucross), sparfloxacin (Zagam), temafloxacin (Omniflox), tosufloxacin (Ozex, Tosacin), clinafloxacin, gatifloxacin (Zigat, Tequin) (Zymar-opth.), gemifloxacin (Factive), moxifloxacin (Acflox Woodward, Avelox, Vigamox, sitafloxacin (Gracevit), trovafloxacin (Trovan), prulifloxacin (Quisnon); oxazolidinones such as eperezolid, linezolid, posizolid, radezolid, ranbezolid, sutezolid, and tedizolid; polymyxins such as polysporin, neosporin, polymyxin B, polymyxin E (colistin); rifamycins such as rifampicin or rifampin, rifabutin, rifapentine, and rifaximin; lipiarmycins such as fidaxomicin; macrolides such as azithromycin, clarithromycin, dirithromycin, erythromycin, roxithromycin, telithromycin, carbomycin A, josamycin, kitasamycin, midecamycin/midecamycin acetate, oleandomycin, solithromycin, spiramycin, and troleandomycin; lincosamides such as lincomycin, clindamycin, and pirlimycin; cyclic lipopeptides such as daptomycin; glycopeptides such as vancomycin and teichoplanin; glycylcyclines such as tigecycline. Thus, any one or more of the foregoing antibiotics can be combined with any of the antisense oligomers described herein, for the treatment of any of the bacterium or bacteria described herein.

In some embodiments, the antimicrobial agent is selected from one or more of aminoglycoside antibiotics, tetracycline antibiotics, and β-lactam antibiotics, as described herein. In some of these and related embodiments, the bacterium comprises or expresses a gene selected from one or more of accA, and the antisense oligomer is targeted against the fatty acid biosynthesis gene. In some of these and related embodiments, the bacterium comprises or expresses a gene selected from one or more of murA, and the antisense oligomer is targeted against the peptidoglycan biosynthesis gene. In some of these and related embodiments, the bacterium comprises or expresses a gene selected from one or more of rpmB, and the antisense oligomer is targeted against the ribosomal protein gene. In some of these and related embodiments, the bacterium comprises or expresses a gene selected from one or more of adk, and the antisense oligomer is targeted against the cellular homeostasis gene. In some of these and related embodiments, the bacterium comprises or expresses a gene selected from one or more of infA, and the antisense oligomer is targeted against the protein biosynthesis gene. In some of these and related embodiments, the bacterium comprises or expresses a gene selected from one or more of ftsZ, and the antisense oligomer is targeted against the cell division gene. In some of these and related embodiments, the bacterium comprises or expresses a gene selected from one or more of rpoD, and the antisense oligomer is targeted against the RNA synthesis gene. In some of these and related embodiments, the bacterium comprises or expresses a gene selected from one or more of aroC, and the antisense oligomer is targeted against the aromatic compound biosynthesis gene. In specific embodiments, the bacterium is *Escherichia coli* or *Acinetobacter* spp.

In some embodiments, the antimicrobial agent is a beta-lactam antibiotic, as described herein. In certain of these and related embodiments, the bacterium comprises or expresses a beta-lactamase such as BlaT, and the antisense oligomer is targeted against the beta-lactamase. In particular embodiments, the antimicrobial agent is a carbapenem. Examples of carbapenems include meropenem, imipenem, ertapenem, doripenem, panipenem, biapenem, razupenem, tebipenem, lenapenem, tomopenem, and ampicillin. In specific embodiments, the antimicrobial agent is meropenem. In particular embodiments, the antimicrobial agent is a cephalosporin (cephem), penicillin or penicillin derivative (penam). In particular embodiments, the antisense oligomer reduces the MIC of a carbapenem such as meropenem against a bacteria, for example, a MDR strain of *E. coli* or *Acinetobacter baumannii*. In some embodiments, the combination of the antisense oligomer and the carbapenem such as meropenem reduces (e.g., synergistically reduces) bacterial cell growth or increase (e.g., synergistically increases) bacterial cell-killing, for example, of a MDR strain of *E. coli* or *Acinetobacter baumannii*.

In some embodiments, the antimicrobial agent is an aminoglycoside, as described herein. Examples of aminoglycosides include tobramycin, gentamicin, kanamycin a, amikacin, dibekacin, sisomicin, netilmicin, neomycin B, neomycin C, neomycin E (paromomycin), and streptomycin. In specific embodiments, the antimicrobial agent is tobramycin. In particular embodiments, the antisense oligomer reduces the MIC of an aminoglycoside such as tobramycin against a bacteria, for example, a MDR strain of *E. coli* or *Acinetobacter baumannii*. In some embodiments, the combination of the antisense oligomer and the aminoglycoside such as tobramycin reduces (e.g., synergistically reduces) bacterial cell growth or increases (e.g., synergistically increases) bacterial cell-killing, for example, of a MDR strain of *E. coli* or *Acinetobacter baumannii*. In some of these and related embodiments, the bacterium comprises or expresses the antibiotic resistance gene adeA, and the antisense oligomer is targeted against the antibiotic resistance gene. In specific embodiments, the bacterium is *Escherichia coli* or *Acinetobacter baumannii*.

In certain embodiments, the antimicrobial agent is a polymyxin such as colistin (polymyxin E), polysporin, neosporin, or polymyxin B. In specific embodiments, the antimicrobial agent is colistin. In particular embodiments, the antisense oligomer reduces the MIC of a polymyxin such as colistin against a bacteria, for example, a MDR strain of *E. coli* or *Acinetobacter baumannii*. In some embodiments, the combination of the antisense oligomer and the polymyxin such as colistin reduces (e.g., synergistically reduces) bacterial cell growth or increases (e.g., synergistically increases) bacterial cell-killing, for example, of a MDR strain of *E. coli* or *Acinetobacter baumannii*.

In certain embodiments, the antimicrobial agent includes one or more of ceftazidime, doxycycline, piperacillin, meropenem, chloramphenicol, and/or co-trimoxazole (trimethoprim/sulfamethoxazole). In some of these and related embodiments, the bacterium is an *Escherichia* species that comprises or expresses one or more antibiotic resistance genes such as cml, and the antisense oligomer is targeted against the antibiotic resistance gene(s). In specific embodiments, the bacterium is *Escherichia coli*.

In some embodiments, the antisense oligomer increases the susceptibility or sensitivity of a given bacterium to the antimicrobial agent, relative to the antimicrobial agent alone. For example, in certain embodiments, the antisense oligomer increases the susceptibility or sensitivity of the bacteria or bacterium to the antimicrobial agent by increasing the bactericidal (cell-killing) and/or bacteriostatic (growth-slowing) activity of the antimicrobial agent against the bacteria or bacterium being targeted, relative to the antimicrobial agent alone. In particular embodiments, the antisense oligomer increases the susceptibility or sensitivity by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone, or by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to the antimicrobial agent alone. In some embodiments, the antisense oligomer synergistically increases the susceptibility or sensitivity of a given bacteria to the antimicrobial agent, relative to the antimicrobial agent alone.

In some embodiments, the antisense oligomer reduces the minimum inhibitory concentration (MIC) of an antimicrobial agent against the bacteria or bacterium being targeted, relative to the antimicrobial agent alone. The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in certain embodiments, the oligomer reduces the minimum inhibitory concentration (MIC) of an antimicrobial agent against the bacteria or bacterium by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone. In certain embodiments, the oligomer reduces the minimum inhibitory concentration (MIC) of an antimicrobial agent against the bacteria or bacterium by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to the antimicrobial agent alone. In some embodiments, the antisense oligomer synergistically reduces the MIC of an antimicrobial agent against the bacteria or bacterium being targeted, relative to the antimicrobial agent alone.

In some embodiments, the antisense oligomer that increases the sensitivity or reduces the MIC is targeted against blaT, the bacterium is *Escherichia coli* or *Acinetobacter* spp. that comprises or expresses BlaT, and the antimicrobial agent is a beta-lactam such as cephalosporins, penicillin, penicillin derivatives (penams) or ampicillin.

In some embodiments, the antisense oligomer that increases the sensitivity or reduces the MIC is targeted against cml, the bacterium is *Escherichia coli* or *Acinetobacter* spp. that comprises or expresses Cml, and the antimicrobial agent is chloramphenicol.

In particular embodiments, the antisense oligomer that increases the sensitivity or reduces the MIC is targeted against adeA, the bacterium is *Escherichia coli* or *Acinetobacter baumannii* that comprises or expresses AdeA, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against accA, the bacterium is *Escherichia coli* or *Acinetobacter baumannii* that comprises or expresses AccA, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against murA, the bacterium is *Escherichia coli* or *Acinetobacter baumannii* that comprises or expresses MurA, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against rpmB, the bacterium is *Escherichia coli* or *Acinetobacter baumannii* that comprises or expresses RpmB, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against adk, the bacterium is *Escherichia coli* or *Acinetobacter baumannii* that comprises or expresses Adk, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against infA, the bacterium is *Escherichia coli* or *Acinetobacter baumannii* that comprises or expresses InfA, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against ftsZ, the bacterium is *Escherichia coli* or *Acinetobacter baumannii* that comprises or expresses FtsZ, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against rpoD, the bacterium is *Escherichia coli* or *Acinetobacter baumannii* that comprises or expresses RpoD, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

In particular embodiments, the antisense oligomer that increases the sensitivity or reduces the MIC is targeted against aroC, the bacterium is *Escherichia coli* or *Acinetobacter baumannii* that comprises or expresses AroC, and the antimicrobial agent is an aminoglycoside antibiotic (e.g., tobramycin, gentamicin, kanamycin, amikacin, dibekacin, sisomicin, netilmicin, neomycin B, neomycin C, neomycin E (paromomycin), streptomycin), a tetracycline antibiotic (e.g., tetracycline, chlortetracycline, oxytetracycline, demeclocycline, lymecycline, meclocycline, methacycline, minocycline, rolitetracycline, doxycyline), or a β-lactam antibiotic (e.g., carbapenem, penicillin derivative (penam), cephalosporin (cephem), monobactam).

VI. Treatment Monitoring Methods

The efficacy of a given therapeutic regimen involving the methods described herein may be monitored, for example, by general indicators of bacterial infection, such as complete blood count (CBC), nucleic acid detection methods, immunodiagnostic tests, or bacterial culture.

In some aspects, identification and monitoring of bacterial infection involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The PMO or PPMO treatment regimen may be adjusted (dose, frequency, route, etc.), as indicated, based on the results of immunoassays, other biochemical tests and physiological examination of the subject under treatment.

From the foregoing, it will be appreciated how various objects and features of the present disclosure are met. The method provides an improvement in therapy against bacterial infection, for example, multi-drug resistant (MDR) bacteria, using anti-acpP antisense oligomers to achieve enhanced cell uptake and anti-bacterial action. As a result, drug therapy is more effective and less expensive, both in terms of cost and amount of compound required.

One exemplary aspect is that compounds effective against virtually any pathogenic bacterial can be readily designed and tested, e.g., for rapid response against new drug-resistant strains.

The following examples are intended to illustrate but not to limit the disclosure. Each of the patent and non-patent references referred to herein is incorporated by reference in its entirety.

EXAMPLES

Materials and Methods

Peptide-Conjugated Phosphorodiamidate Morpholino Oligomers. PPMOs were synthesized and purified at Sarepta Therapeutics Inc. (Cambridge, Mass., USA) as previously described (Tilley et al., Antimicrob Agents Chemother 50:2789-2796, 2006). Lyophilized PPMOs were dissolved in ultrapure water and sterile-filtered. PPMO peptides were attached to either the 5' or 3' end of the oligomer sequence as indicated.

Bacteria. Bacterial strains were obtained through the clinical microbiology lab at UT Southwestern unless otherwise noted. Strains also included those purchased through ATCC, the *E. coli* Genetic Stock Center (Yale University), or received from collaborators. They included both genome-sequenced isolates as well as clinical isolates with varying levels of antibiotic resistance. Single colonies were grown aerobically to stationary phase (1-2 mLs at 37° C., 250 rpm) in Mueller Hinton cation-adjusted (MH II) broth (Becton-Dickinson Difco BBL, Franklin Lakes, N.J., USA). The OD600 was taken and a working stock of $5 \times 10^5$ was generated based on the individual strain's colony forming units (CFU)/mL/OD. Working stocks were diluted in 150 mM NaCl and plated on tryptic-soy agar w/5% sheep blood plate (Remel, Lenexa, Kans.) to verify the starting concentration. For minimal nutrient conditions, *E. coli* was incubated in MOPS minimal medium (Neidhart et al., J Bacteriol 119:736-747, 1974) and *Acinetobacter* was performed in AB minimal media (*Agrobacterium* minimal media) with 10 mM citrate (Clark, J Mol Biol 23:99-112, 1967).

Minimal Inhibitory Concentration Assays. Minimal inhibitory concentration (MIC) assays were performed in Mueller Hinton II medium using the microdilution method as described by the Clinical and Laboratory Standards Institute (CLSI). Optical density (OD) of cultures was read in a microplate spectrophotometer at 595-600 nm. After 18-20 hours of aerobic growth (200-250 rpm) at 37° C., 100 µl cultures with an OD of <0.06 were scored as no growth. Antibiotics were purchased from Sigma Chemical Co. (St. Louis, Mo., USA).

Minimal Bactericidal Concentration Assays. Minimum Bactericidal Concentration (MBC) assays were performed as MICs, with aliquots taken at noted time points, diluted in 150 mM NaCl and plated. Plates were incubated for 18 hours and colonies were enumerated. The $IC_{75}$ of a PPMO was defined as the MIC value in 75% of the strains tested.

Transmission election microscopy (TEM). At the specified time points the bacterial samples were centrifuged, washed with Hank's Balanced Salt Solution (HBSS-) (Life Technologies, Gibco, Grand Island, N.Y., USA), resuspended in ½ Karnovsky's fixative (4% Paraformaldehyde, 2.5% Glutaraldehyde and 0.1M Sodium Phosphate Buffer), and stored at 4° C. until processing by the Electron Microscopy Core Facility UT Southwestern Medical Center, Dallas, Tex. The TEM grids were examined and images were captured on a FEI Tecnai G2 Spirit Biotwin microsope (FEI Company, Hillsboro, Oreg., USA).

Synergy Studies. MICs were performed with a PPMO and a classic antibiotic (as indicated) in a 96 well plate. The PPMO was diluted first horizontally down the plate and the classic antibiotic was diluted across the rows of the plate. Inhibition was determined by visual observation and OD600 (see Berenbaum et al., J Antimicrob Chemother 12:555-563, 1983; and Berenbaum, J Infect Dis 137:122-130, 1978). For determination of colony counts, aliquots of the target organisms were incubated with the desired concentration of PPMO, traditional antibiotic or combination of both and grown at 37° C., with centrifugation at 250 rpm. Cultures were diluted in 150 mM NaCl at 0 and 24 hour time points, plated and then colonies were enumerated. Synergy was quantified using the method of isoboles as described (see Tallarida, Genes Cancer. 2:1003-8, 2011): (Effective concentration of antibiotic/MIC of antibiotic)+(Effective concentration of PPMO/MIC of PPMO). Calculated values less than 1 indicated synergy.

Graphical Software. Standard deviation and graphical analysis was performed on GraphPad Prism®6 software (GraphPad Software, Inc., San Diego, Calif., USA).

Example 1

Activity of PPMO Targeted Against acpP of *E. coli*

A cell-penetrating peptide-conjugated phosphorodiamidate morpholino oligomer (PPMO) targeted against the *E. coli* acpP gene was prepared and its efficacy was evaluated in vitro against a multi-drug-resistant strain of *E. coli* (A15070834).

The acpP-targeted PPMO#2 has the following sequence: 5'-CTTCGATAGTG-3' (SEQ ID NO:1). The PPMO was conjugated at its 3'-end to the C-terminal beta-alanine of (RXR)$_4$XB (SEQ ID NO:59).

The acpP-targeted PPMO (1 μM) was added to bacterial cultures either alone or in combination with tobramycin (2 μg/ml). PPMO scramble control (1 μM), peptide control (1 μM), and tobramycin (2 μg/ml) were added to bacterial cultures separately or in various combinations. Colony-forming units (CFUs) were counted at 24 hours.

Figure 2A:
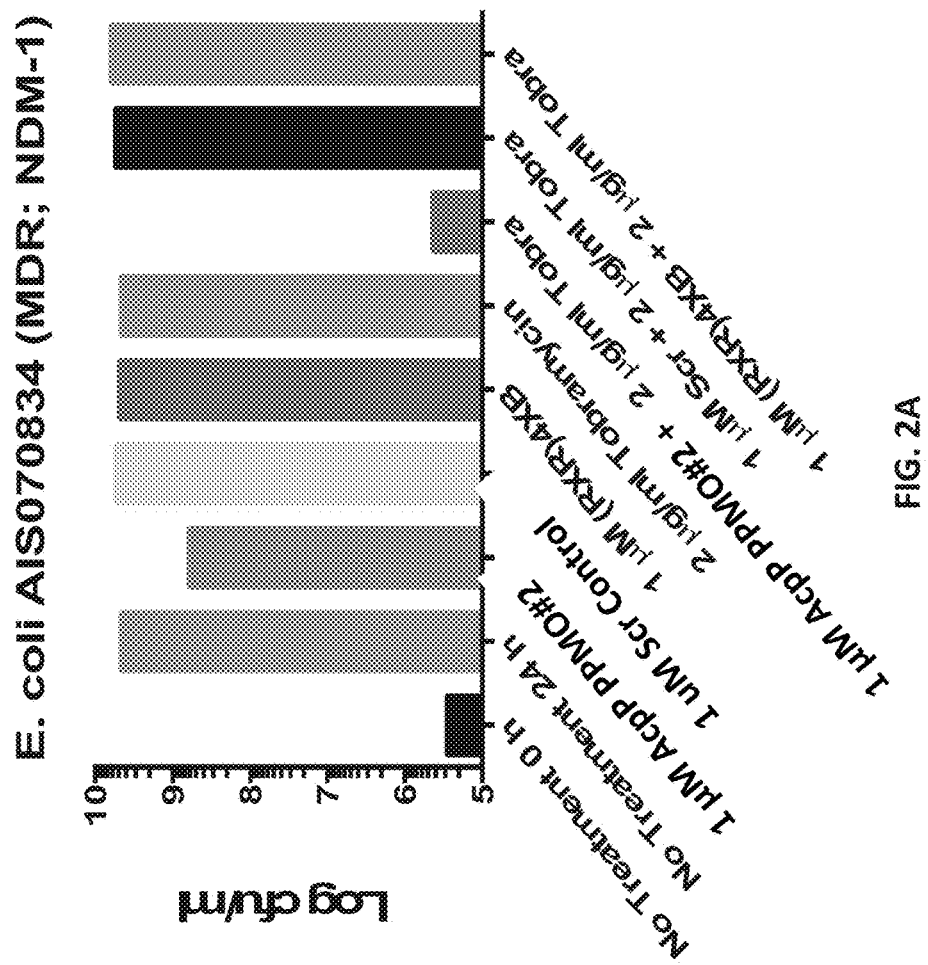
FIG. 2A shows that acpP-targeted PPMO#2 not only reduced bacterial growth (colony-forming units; CFUs) of a multi-drug-resistant strain of *E. coli* by about 1-log relative to scramble PPMO control, but in combination with tobramycin also synergistically reduced bacterial growth by over 4-logs relative to controls. Tobramycin and control PPMOs (either alone or in combination) had no significant effect on bacterial growth.

As shown in FIG. 2A, the acpP-targeted PPMO#2 not only reduced bacterial growth (colony-forming units; CFUs) of the multi-drug-resistant strain of *E. coli* by about 1-log relative to scramble PPMO and peptide controls, but in combination with tobramycin also synergistically reduced bacterial growth by over 4-logs relative to controls. Tobramycin and control PPMOs (either alone or in combination) had no significant effect on bacterial growth.

Example 2

Effect of acpP-Targeted PPMO on MIC of Tobramycin

A PPMO was tested for its effects on the minimum inhibitory concentration (MIC) of tobramycin against a multi-drug-resistant strain of *E. coli* (A15070834).

The acpP-targeted PPMO#1 has the following sequence: 5'-CTTCGATAGTG-3' (SEQ ID NO:1). The PPMO was conjugated at its 5'-end to the C-terminal beta-alanine of (RXR)$_4$XB (SEQ ID NO:59).

The MIC of the tobramycin was measured using the microdilution method of the Clinical Laboratory Standards Institute in a 96-well microtiter plate format. Multiple, identical dilution series of tobramycin were included on each microtiter plate. In each dilution series of tobramycin, a fixed amount of PPMO was added. Each dilution series of antibiotic included a different concentration of PPMO. The results are shown in FIGS. 2B-2C.

Figure 2B:
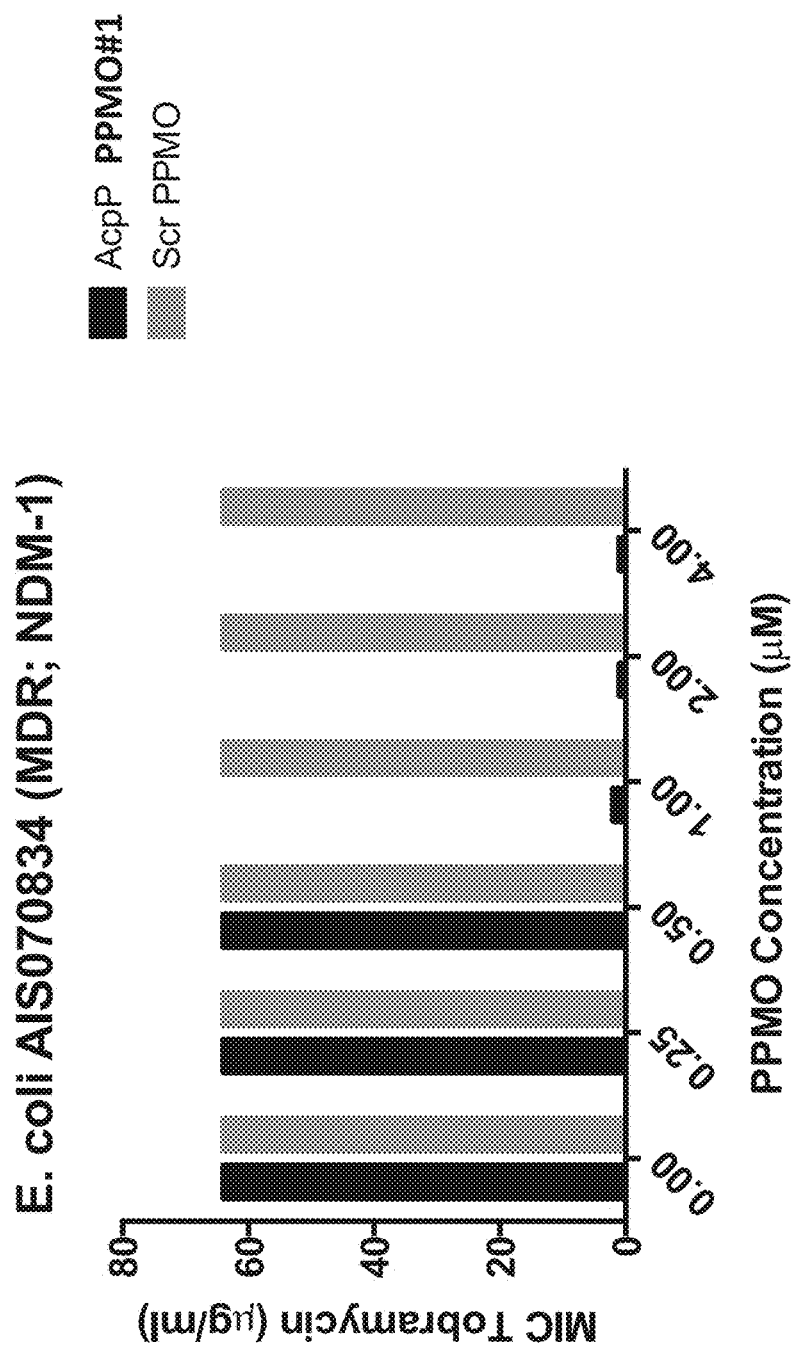
FIG. 2B (linear scale) and FIG. 2C (log scale) show that increasing amounts of acpP-targeted PPMO#1 significantly decreased the minimum inhibitory concentration (MIC) of tobramycin against a multi-drug-resistant strain of *E. coli* in a concentration-dependent manner.
Figure 2C:
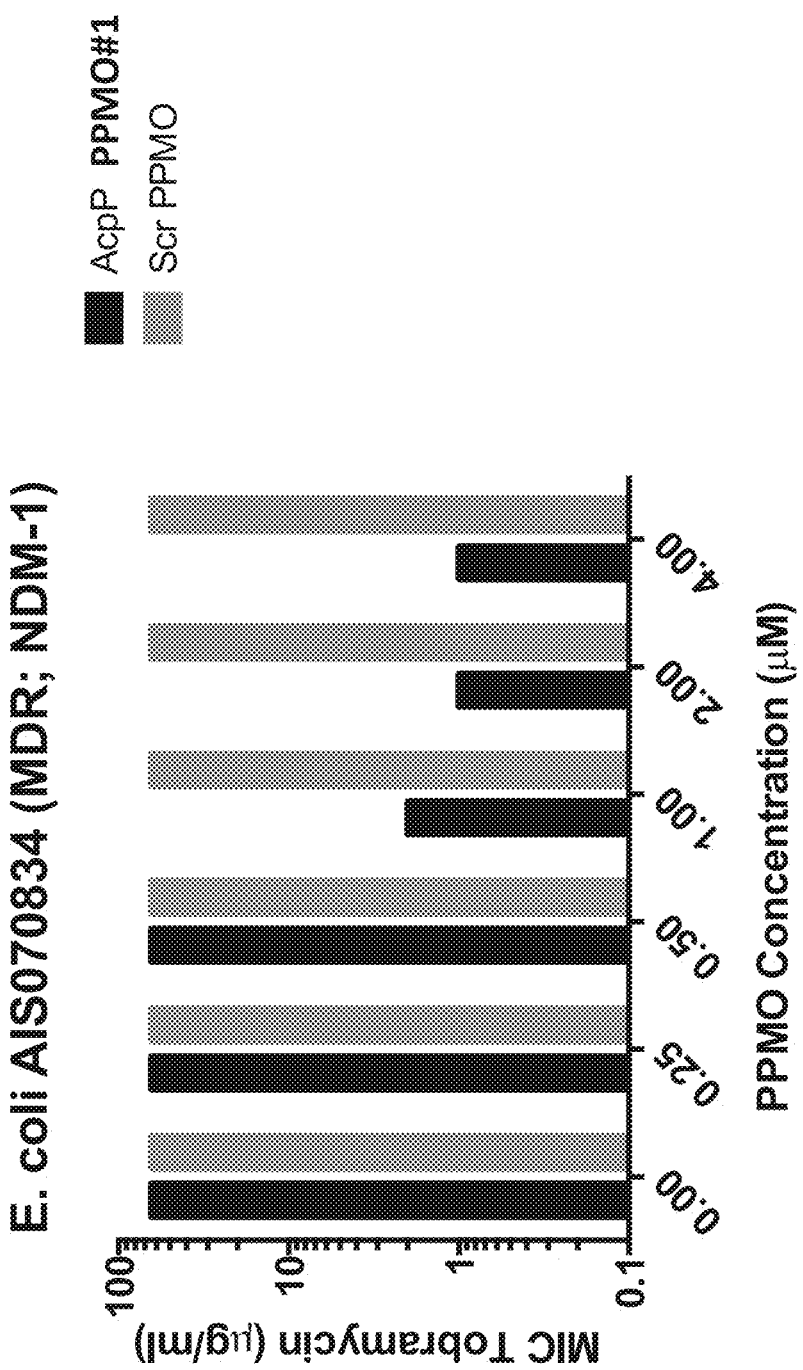

FIG. 2B (linear scale) and FIG. 2C (log scale) show that increasing amounts of acpP-targeted PPMO#1 significantly decreased the minimum inhibitory concentration (MIC) of tobramycin against a multi-drug-resistant strain of *E. coli* in a concentration-dependent manner.

Example 3

Activity of PPMO Targeted Against acpP of *A. baumannii*

A cell-penetrating peptide-conjugated phosphorodiamidate morpholino oligomer (PPMO) targeted against the *A. baumannii* acpP gene was prepared and its efficacy was evaluated in vitro against a multi-drug-resistant strain of *A. baumannii* (AYE).

The acpP-targeted PPMO#7 has the following sequence: 5'-ATATCGCTCAC-3' (SEQ ID NO:2). The PPMO was conjugated at its 3'-end to the C-terminal beta-alanine of (RXR)$_4$XB (SEQ ID NO:59).

The acpP-targeted PPMO#7 (2 μM) was added to bacterial cultures either alone or in combination with colistin (0.25 μg/ml), meropenem (0.5 μg/ml), or tobramycin (2 μg/ml). PPMO scramble control (2 μM), colistin (0.25 μg/ml), meropenem (0.5 μg/ml), and tobramycin (2 μg/ml) were added to bacterial cultures separately or in various combinations. Colony-forming units (CFUs) were counted at 24 hours. The results are shown in FIGS. 3-5.

Figure 3:
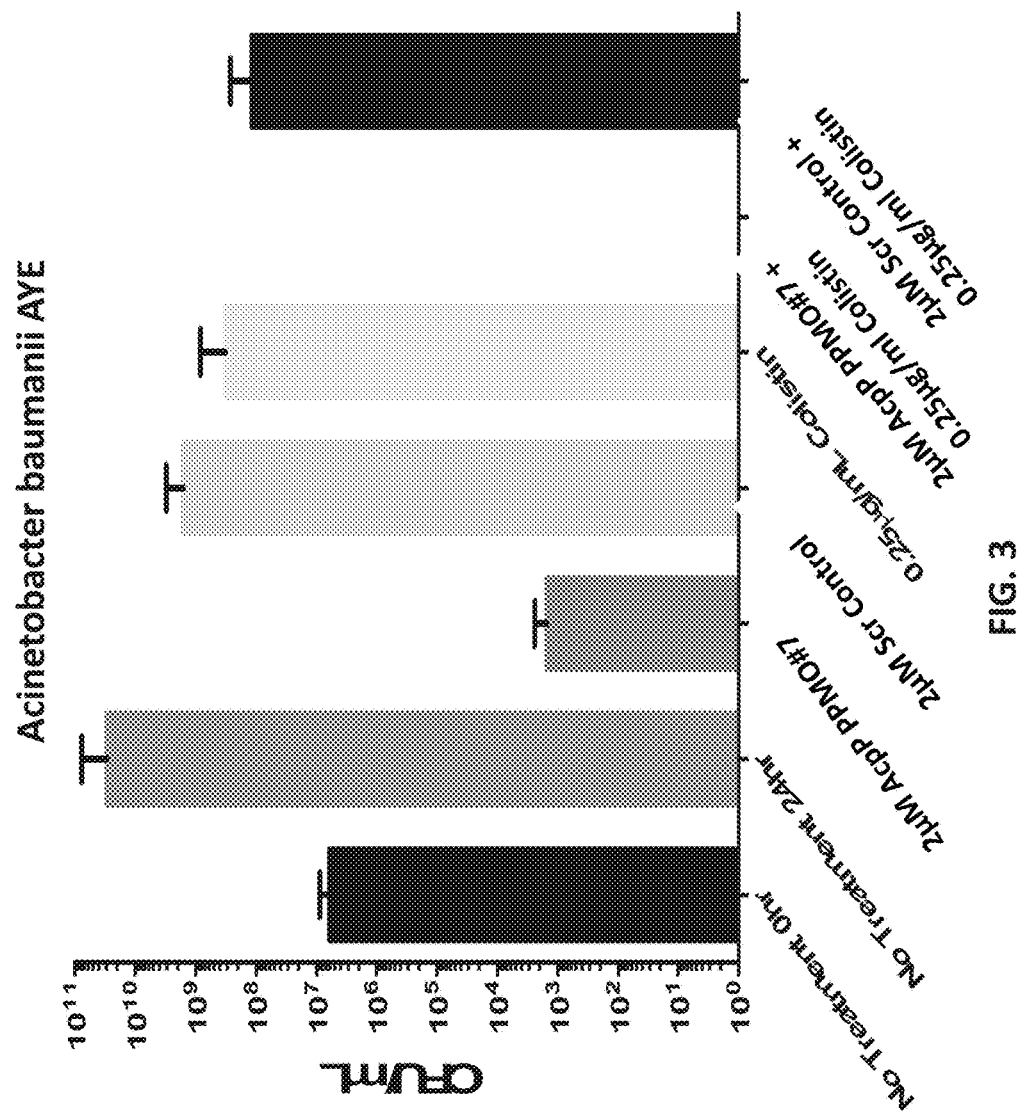
FIG. 3 shows that acpP-targeted PPMO#7 not only reduced bacterial growth (colony-forming units; CFUs) of a multi-drug-resistant strain of *Acinetobacter baumannii* (AYE) by about 6-logs relative to scramble PPMO control, but in combination with colistin also synergistically reduced bacterial growth to undetectable levels (an additional ~3 logs relative to the acpP-targeted PPMO alone). Colistin and control PPMOs (either alone or in combination) did not have this significant of an effect on bacterial growth.

FIG. 3 shows that the acpP-targeted PPMO#7 not only reduced bacterial growth (colony-forming units; CFUs) of the multi-drug-resistant strain of *Acinetobacter baumannii* (AYE) by about 6-logs relative to scramble PPMO control, but in combination with colistin also synergistically reduced bacterial growth to undetectable levels (an additional ~3 logs relative to the acpP-targeted PPMO alone). Colistin and control PPMOs (either alone or in combination) did not have this significant of an effect on bacterial growth.

Figure 4:
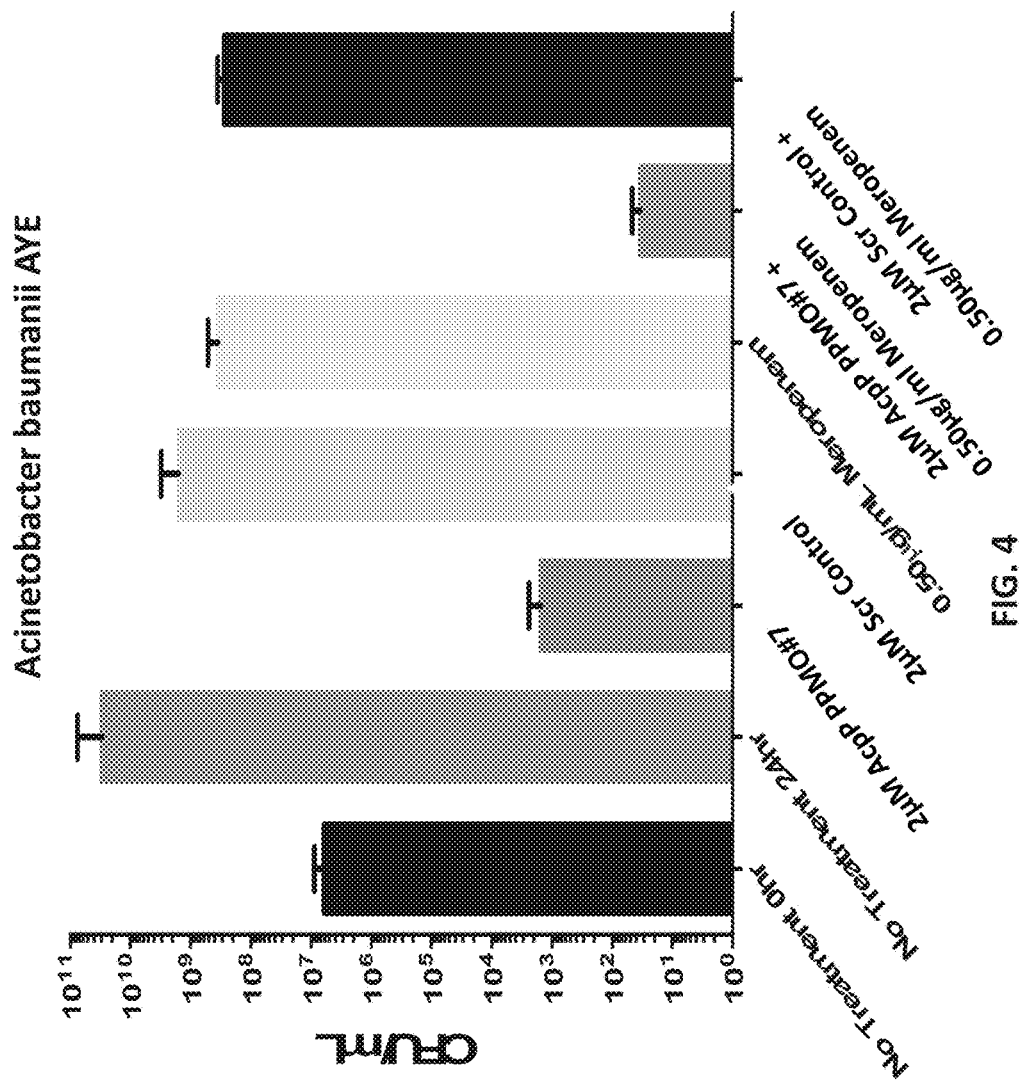
FIG. 4 shows that acpP-targeted PPMO#7 not only reduced bacterial growth (colony-forming units; CFUs) of a multi-drug-resistant strain of *Acinetobacter baumannii* (AYE) by about 5-logs relative to scramble PPMO control, but in combination with meropenem also synergistically reduced bacterial growth by an additional ~2-logs relative to the acpP-targeted PPMO alone. Meropenem and control PPMOs (either alone or in combination) did not have this significant of an effect on bacterial growth.

FIG. 4 shows that the acpP-targeted PPMO#7 not only reduced bacterial growth (colony-forming units; CFUs) of the multi-drug-resistant strain of *Acinetobacter baumannii* (AYE) by about 5-logs relative to scramble PPMO control, but in combination with meropenem also synergistically reduced bacterial growth by an additional ~2-logs relative to the acpP-targeted PPMO alone. Meropenem and control PPMOs (either alone or in combination) did not have this significant of an effect on bacterial growth.

Figure 5:
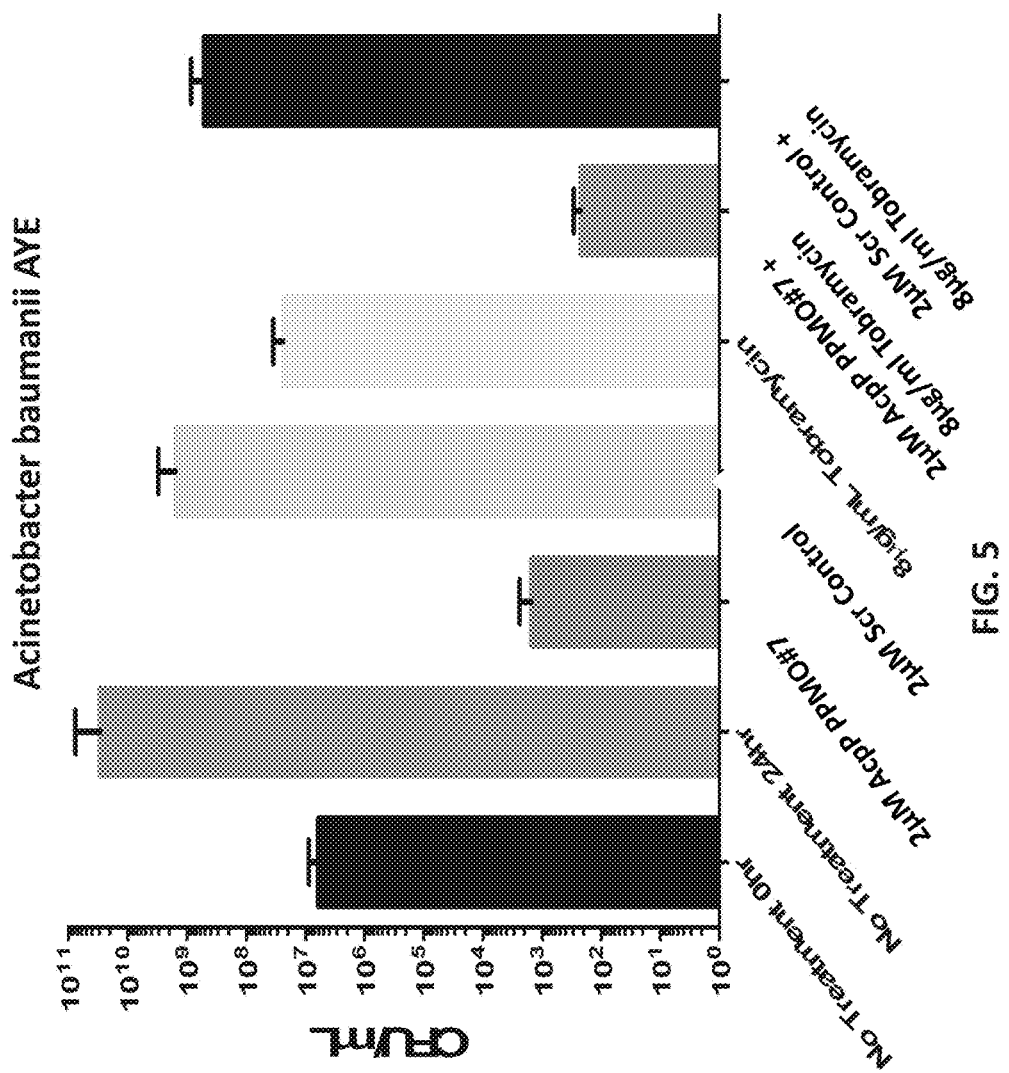
FIG. 5 shows that acpP-targeted PPMO#7 not only reduced bacterial growth (colony-forming units; CFUs) of a multi-drug-resistant strain of *Acinetobacter baumannii* (AYE) by about 6-logs relative to scramble PPMO control, but in combination with tobramycin also synergistically reduced bacterial by an additional ~1-log relative to the acpP-targeted PPMO alone. Tobramycin and control PPMOs (either alone or in combination) did not have this significant of an effect on bacterial growth.

FIG. 5 shows that the acpP-targeted PPMO#7 not only reduced bacterial growth (colony-forming units; CFUs) of the multi-drug-resistant strain of *Acinetobacter baumannii* (AYE) by about 6-logs relative to scramble PPMO control, but in combination with tobramycin also synergistically reduced bacterial by an additional ~1-log relative to the acpP-targeted PPMO alone. Tobramycin and control PPMOs (either alone or in combination) did not have this significant of an effect on bacterial growth.

Example 4

Effect of acpP-Targeted PPMO on MIC of Antibiotics

The PPMO#7 from Example 3 was tested for its effects on the minimum inhibitory concentration (MIC) of colistin, meropenem, and tobramycin against multi-drug-resistant strains of *Acinetobacter baumannii* (AYE) and *E. coli* AIS070834.

The MIC of the antibiotics colistin, meropenem, and tobramycin was measured using the microdilution method of the Clinical Laboratory Standards Institute in a 96-well microtiter plate format. Multiple, identical dilution series of each antibiotic were included on each microtiter plate. In each dilution series of antibiotic, a fixed amount of PPMO was added. Each dilution series of antibiotic included a different concentration of PPMO. The results are shown in FIGS. 3-8.

Figure 6:
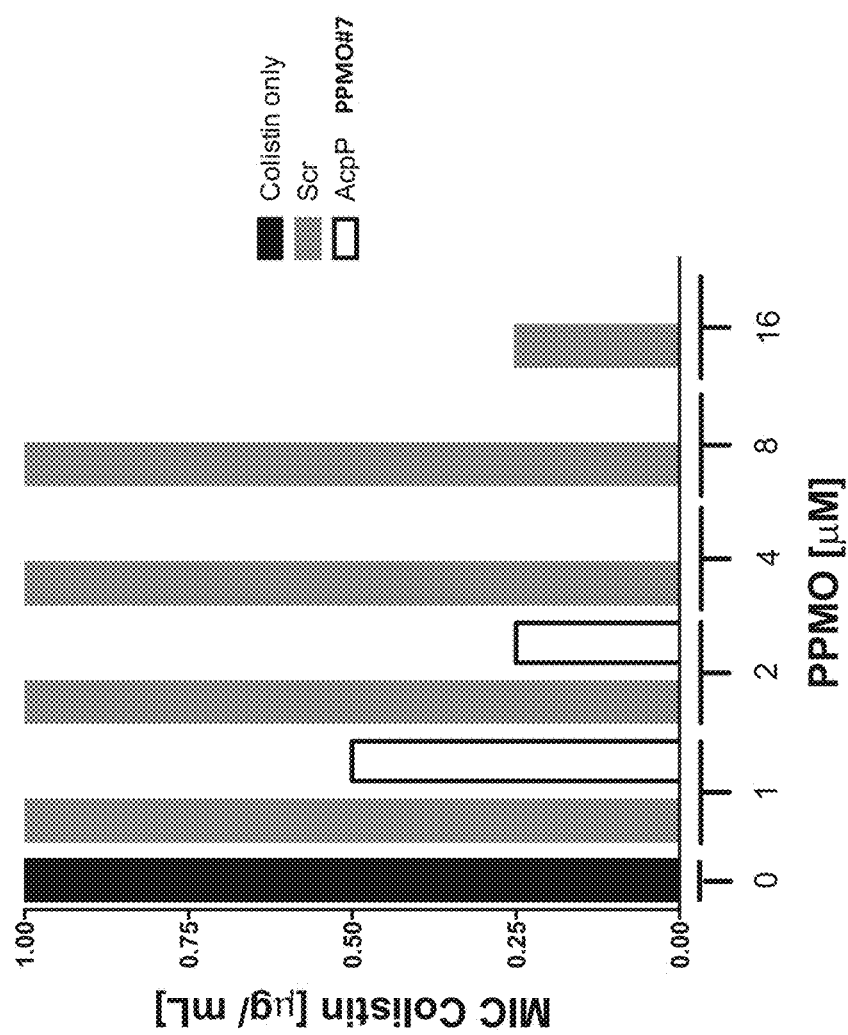
FIG. 6 shows that increasing amounts of acpP-targeted PPMO#7 significantly decreased the minimum inhibitory concentration (MIC) of colistin against a multi-drug-resistant strain of *Acinetobacter baumannii* (AYE) in a concentration-dependent manner.

FIG. 6 shows that increasing amounts of the acpP-targeted PPMO#7 significantly decreased the MIC of colistin against the multi-drug-resistant strain of *Acinetobacter baumannii* (AYE) in a concentration-dependent manner. In the presence of 2 μM of PPMO, the MIC of colistin decreased from 1 μg/mL to 0.25 μg/mL (see also FIG. 3), and synergy was 0.75.

Figure 7:
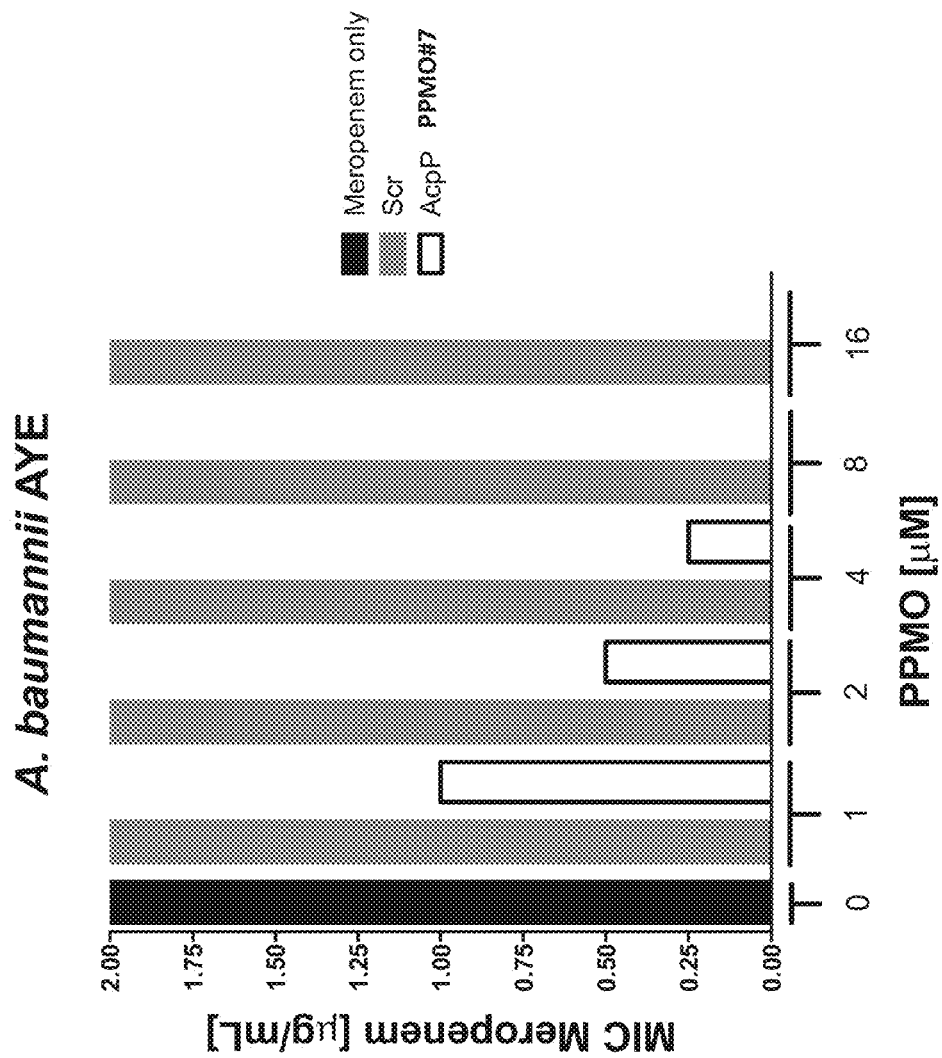
FIG. 7 shows that increasing amounts of acpP-targeted PPMO#7 significantly decreased the minimum inhibitory concentration (MIC) of meropenem against a multi-drug-resistant strain of *Acinetobacter baumannii* (AYE) in a concentration-dependent manner.

FIG. 7 shows that increasing amounts of the acpP-targeted PPMO#7 also significantly decreased the MIC of meropenem against the multi-drug-resistant strain of *Acinetobacter baumannii* (AYE) in a concentration-dependent manner. In the absence of PPMO the MIC of the meropenem was 2 μg/mL, and this was reduced to 0.25 μg/mL when 4 μM PPMO was present (see also FIG. 4). Synergy between meropenem and the acpP-targeted PPMO was 0.75.

Figure 8:
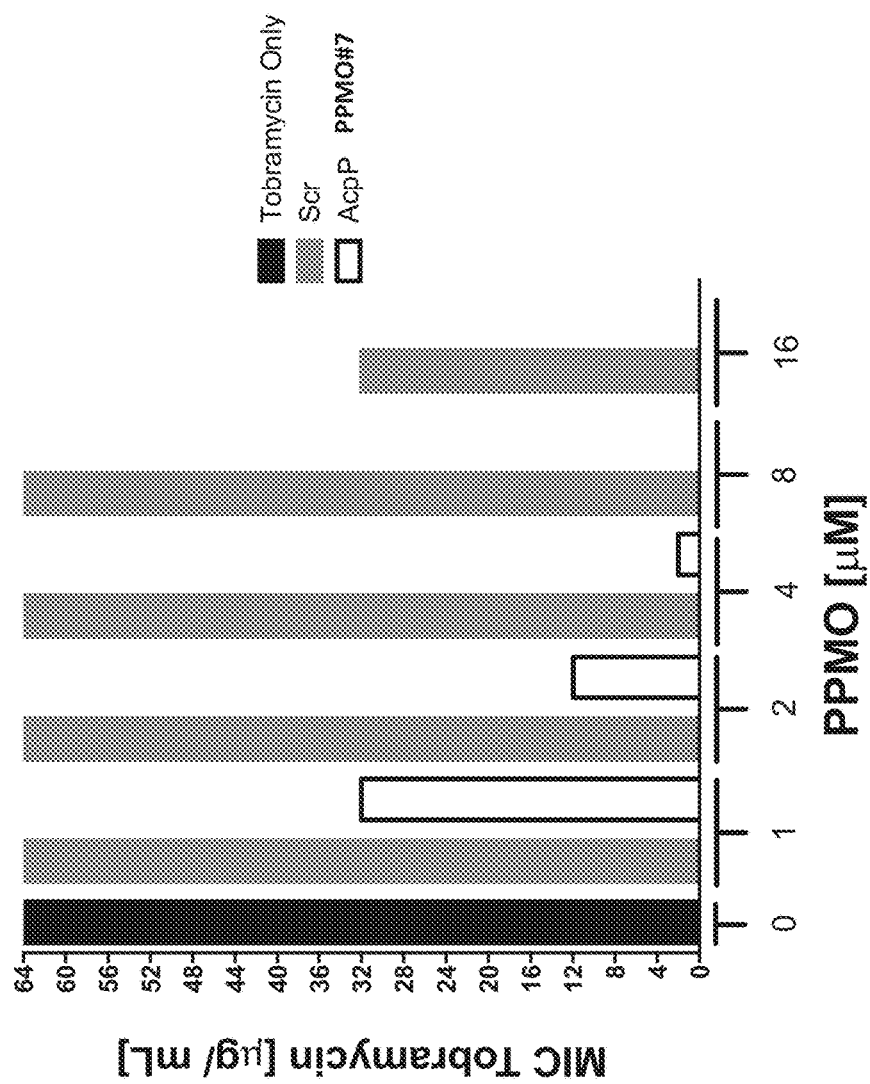
FIG. 8 shows that increasing amounts of acpP-targeted PPMO#7 significantly decreased the minimum inhibitory concentration (MIC) of tobramycin against a multi-drug-resistant strain of *Acinetobacter baumannii* (AYE) in a concentration-dependent manner.

This effect was not limited to antibiotics that affected bacterial membrane structure as synergy was also seen with the aminoglycoside tobramycin. FIG. 8 shows that increasing amounts of the acpP-targeted PPMO#7 significantly decreased the MIC of tobramycin against the multi-drug-resistant strain of *Acinetobacter baumannii* (AYE) in a concentration-dependent manner. In the absence of PPMO, the MIC of tobramycin was 64 μg/mL. The MUC was reduced to 2 μg/mL in the presence of 4 μM PPMO (see also FIG. 5). The synergy between tobramycin and the acpP-targeted PPMO was 0.625.

MICs were performed in both rich and minimal media for both genera of bacteria. Panels of *E. coli* (~22 strains) and *Acinetobacter* spp. (~34 strains) comprised both drug-sensitive and multidrug-resistant strains, as shown in Table E1 below.

TABLE E1

| Pathogen | Strain | Characteristics | Source |
| --- | --- | --- | --- |
| *E. coli* | W3110 | non-pathogenic, K-12 | *E. coli* Genetics Stock Center, New Haven, CT |
| *E. coli* | SMS-3-5 | MDR | ATCC |
| *E. coli* | CVB-1 | NDM1 producer | G. Rossolini, University of Siena, Italy |
| *E. coli* | BCT-B-036NDM-1 | NDM1 producer | P. Nordmann, Hopital de Bicetre, Paris |
| *E. coli* | NDM1-E | NDM1 producer | S. Poutanen, Mt. Sinai Hospital, Toronto |
| *E. coli* | BAA-196 | ESBL, TEM-10 | ATCC |
| *E. coli* | BAA-200 | MDR, SVH-4 | ATCC |
| *E. coli* | BAA-202 | ESBL, ceftazidine resist. | ATCC |
| *E. coli* | ATCC700928 | UTI, genome sequenced | ATCC |
| *E. coli* | ATCC 25922 | Control strain for MIC suscept. | ATCC |
| *E. coli* | E2348/69 | EPEC | J. Kaper, University of Maryland, Baltimore, MD |
| *E. coli* | 1001728 | NDM1 producer | J. K. Rasheed, CDC, Atlanta, GA |
| *E. coli* | 1101851 | NDM1 producer | J. K. Rasheed, CDC, Atlanta, GA |
| *E. coli* | A15070834 | NDM1 producer | J. K. Rasheed, CDC, Atlanta, GA |
| *E. coli* | A1071077 | NDM1 producer | J. K. Rasheed, CDC, Atlanta, GA |
| *A. baumannii* | BAA-1710 | MDR, genome sequenced | ATCC |
| *A. baumannii* | BAA-1709 | Genome sequenced | ATCC |
| *A. baumannii* | AB0057 | MDR | Todd Hoopman, UTSW |
| *A. baumannii* | ATCC 17978 | Genome sequenced | ATCC |
| *A. baumannii* | ATCC 17961 | | ATCC |
| *A. baumannii* | ATCC 17906 | | ATCC |
| *A. baumannii* | AYE (pNDM-1) | AYE with NDM-1 | Bruce Geller, OSU |
| *A. baumannii* | BCT-13-026NDM-1 | NDM1 producer | P. Nordmann, Hopital de Bicetre, Paris |
| *A. baumannii* | ATCC 19606 | Genome sequenced | ATCC |
| *A. iwoffii* | ATCC 17976 | Genome sequenced | ATCC |
| *A. baumannii* | HUMC-1 | | Brad Spellberg, USC |

For all antibiotics tested, there was a corresponding reduction in CFU/ml of at least 1-log when PPMO was combined with the antibiotic compared to either the PPMO or antibiotic alone. The scrambled PPMO at 8 μM or less, showed no activity alone or synergy with the antibiotics tested.

Figure 12B:
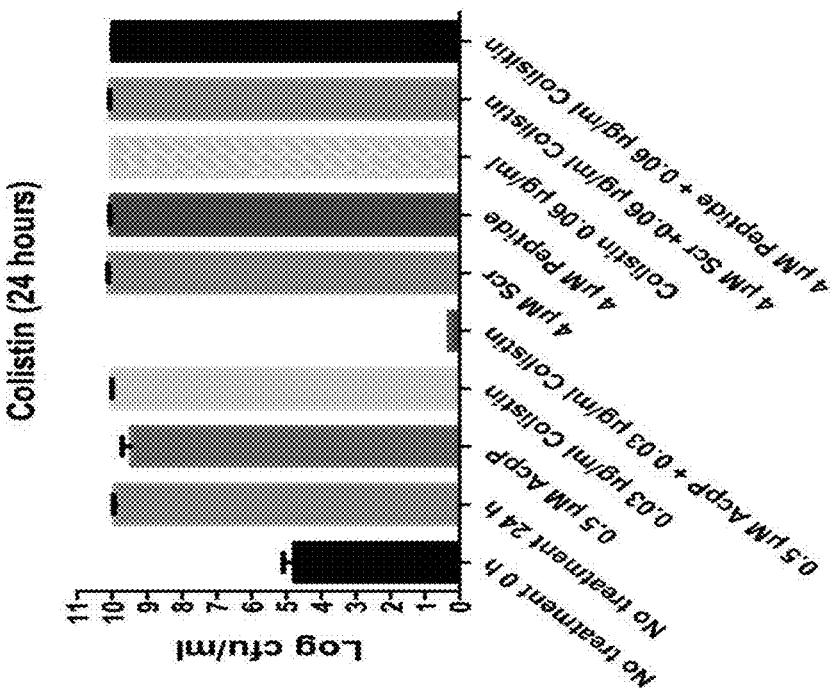
Figure 12A:
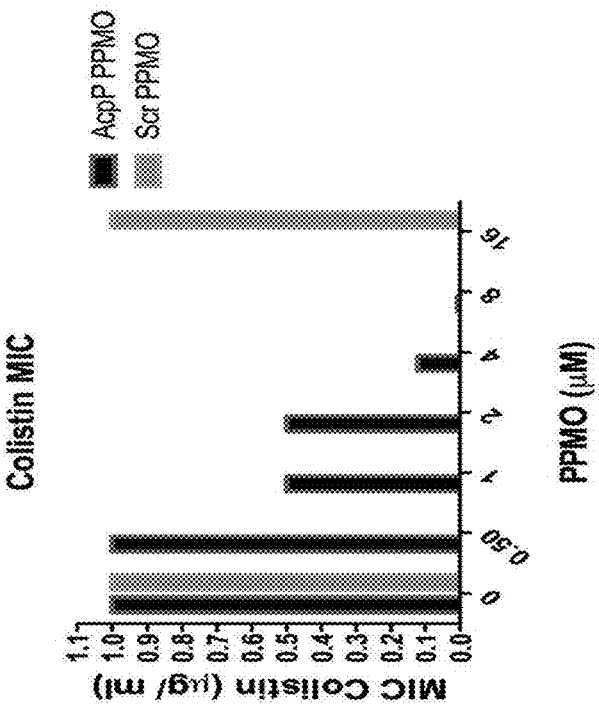
Figure 12C:
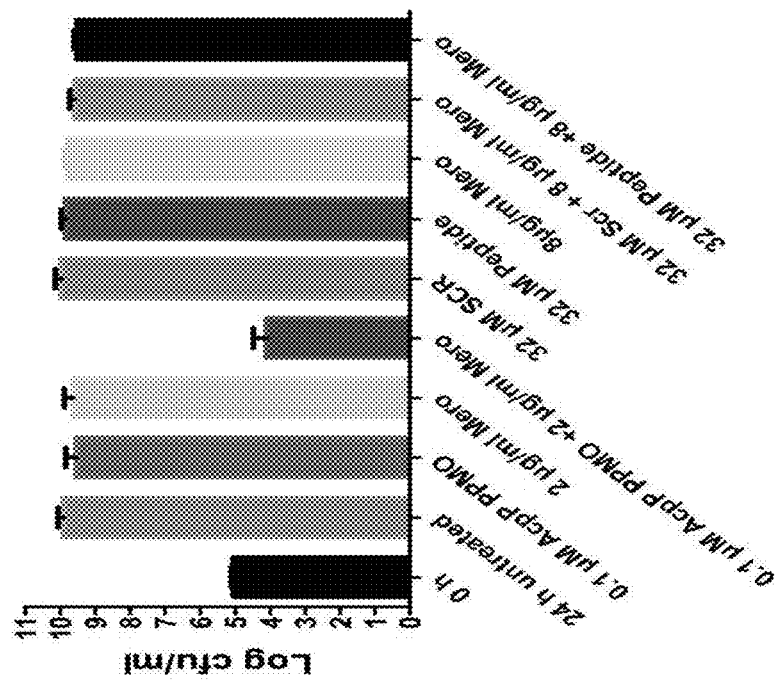
Figure 12D:
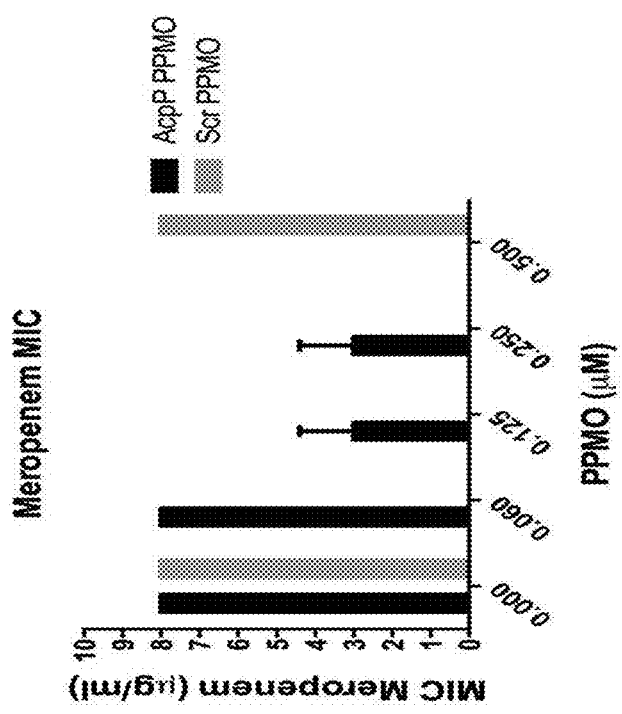

Similar synergy between the acpP (PPMO#1) and the same three antibiotics was seen in the *E. coli* strain A15070834 (see FIGS. 12A-12F). FIGS. 12A-12B show the results for colistin, FIGS. 12C-12D show the results for meropenem, and FIGS. 12E-12F show the results for tobramycin. In all instances, the acpP-targeted PPMO significantly reduced the MIC of the tested antibiotic. The free peptide (RXR)4XB was also tested and by itself had an unmeasurable MIC (data not shown).

Example 5

PPMOs Targeting Essential Genes Inhibit Growth of *Acinetobacter* Spp. and *E. coli* In Vitro PPMOs targeted against acpP were tested for the ability to inhibit the growth of *Acinetobacter* spp. and *E. coli* in vitro. Bacterial strains and culture and assay conditions are described in the Materials and Methods section above.

Figure 13A:
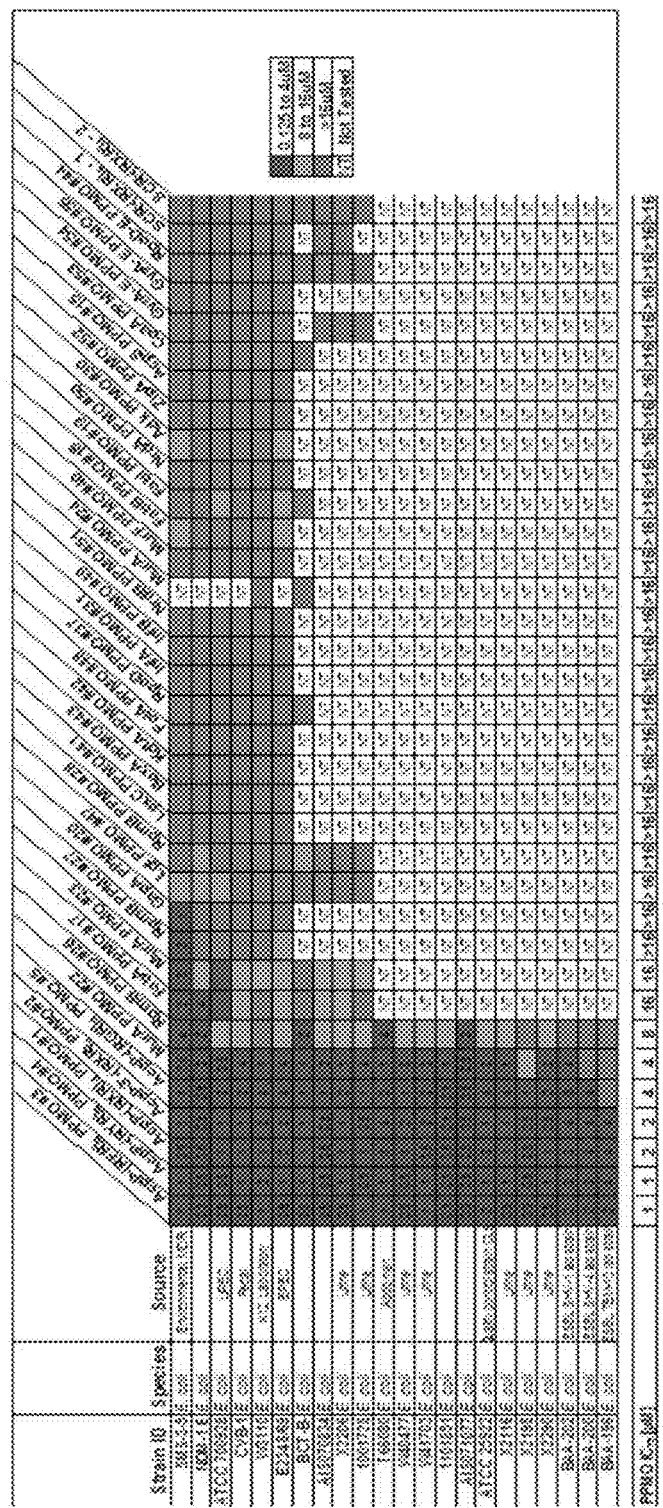

A list of all PPMOs used and their sequences are provided (Tables 3A-B). PPMOs were designed against known or putative essential bacterial genes in a variety of pathways including fatty acid, lipopolysaccharide or peptidoglycan biosynthesis. Regardless of the media used, PPMOs targeted to the acyl carrier protein (AcpP) showed the best in vitro inhibition in both *E. coli* and *Acinetobacter*. In MHII, 6 PPMOs were the most active in *E. coli* with an $IC_{75}$ of 4 μM or less (FIG. 13A). Five of the 6 were all targeted to acpP with the differences related to various peptide attachments or position on the target. The acpP PPMOs had $IC_{75}$ MICs that ranged from 1 to 4 μM. The other active PPMO targeted murA and had an $IC_{75}$ MICs of 4 μM.

Figure 13B:
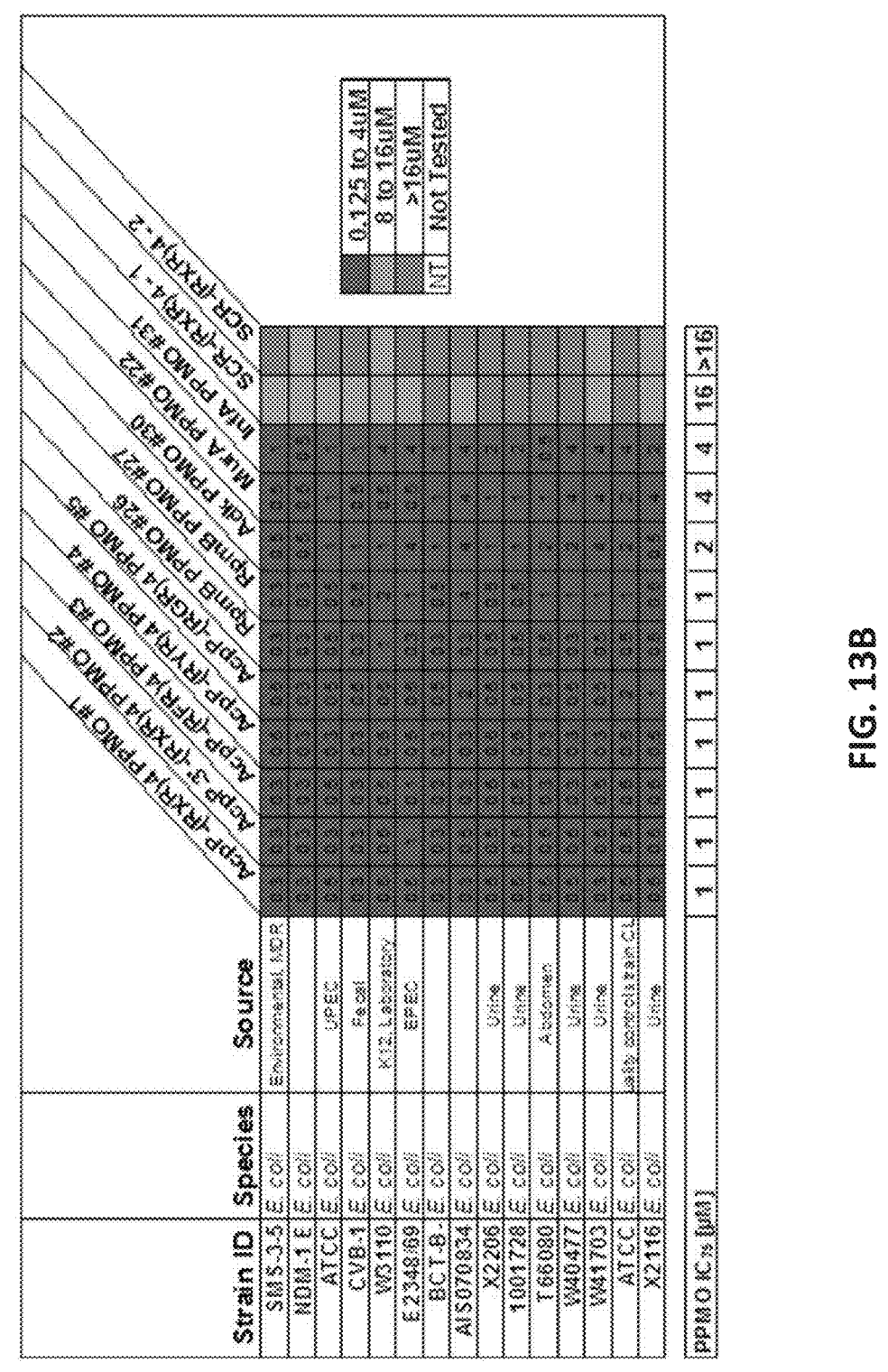

The determination of whether a bacterial gene is essential can vary based on the media in which the bacteria are grown. Fifteen *E. coli* strains were screened in MOPS minimal media (FIG. 13B). This screen increased the number of PPMOs with $IC_{75}$ MICs of 4 μM or less to 10. Six of the ten represented the PPMOs that were found to be effective in MHII media although the MIC values improved with the most potent acpP PPMO having $IC_{75}$ MICs of 0.5 μM. Additional potent PPMOs were identified and included the gene targets: rpmB (a recombinant ribosomal protein gene; $IC_{75}$ MICs of 0.5 and 1 μM), adk (an adenylate kinase gene; $IC_{75}$ MIC of 2 μM) and infA (a transcription antiterminator gene; $IC_{75}$ MIC of 4 μM).

Figure 13C:
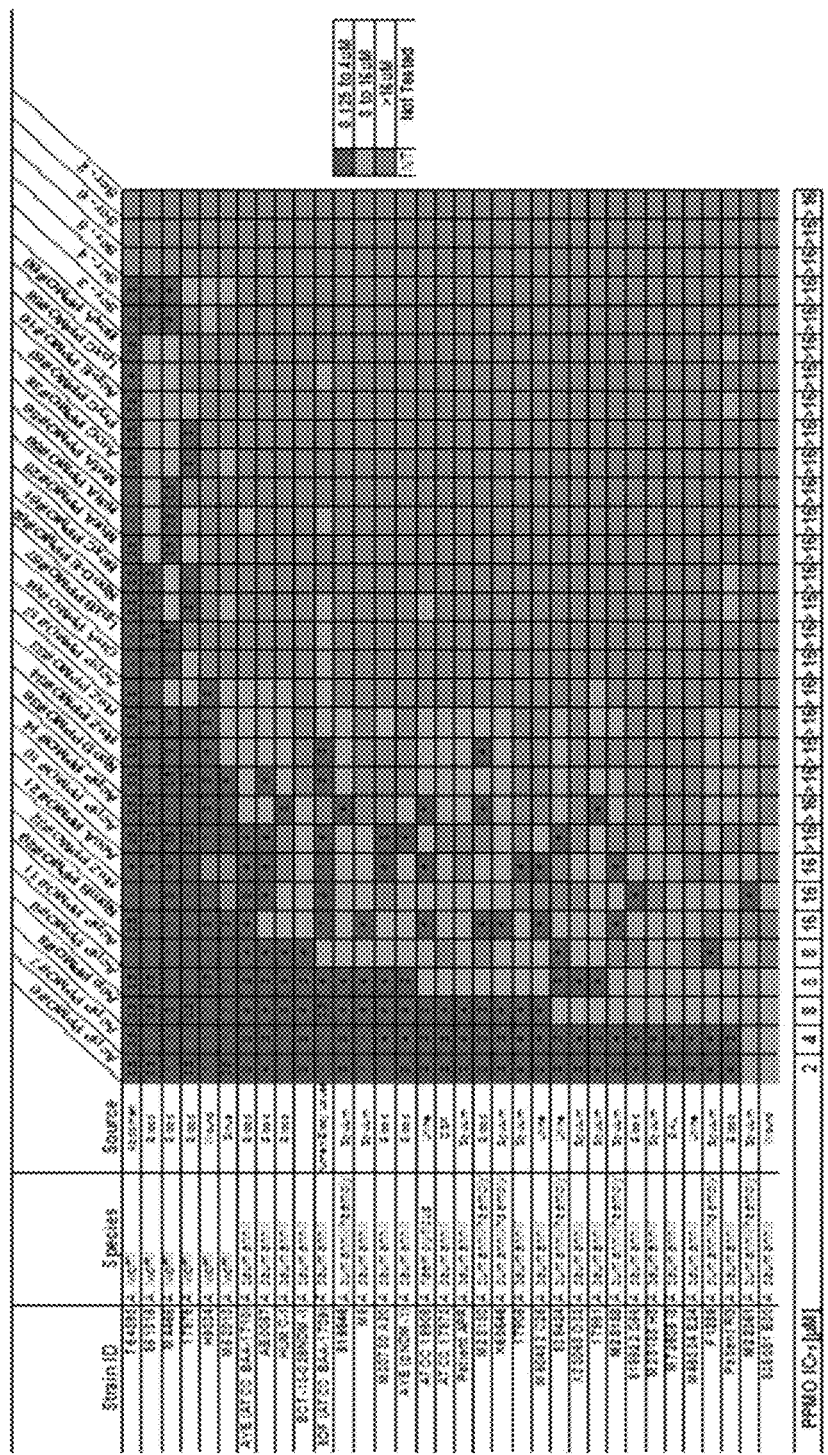
Figure 13D:
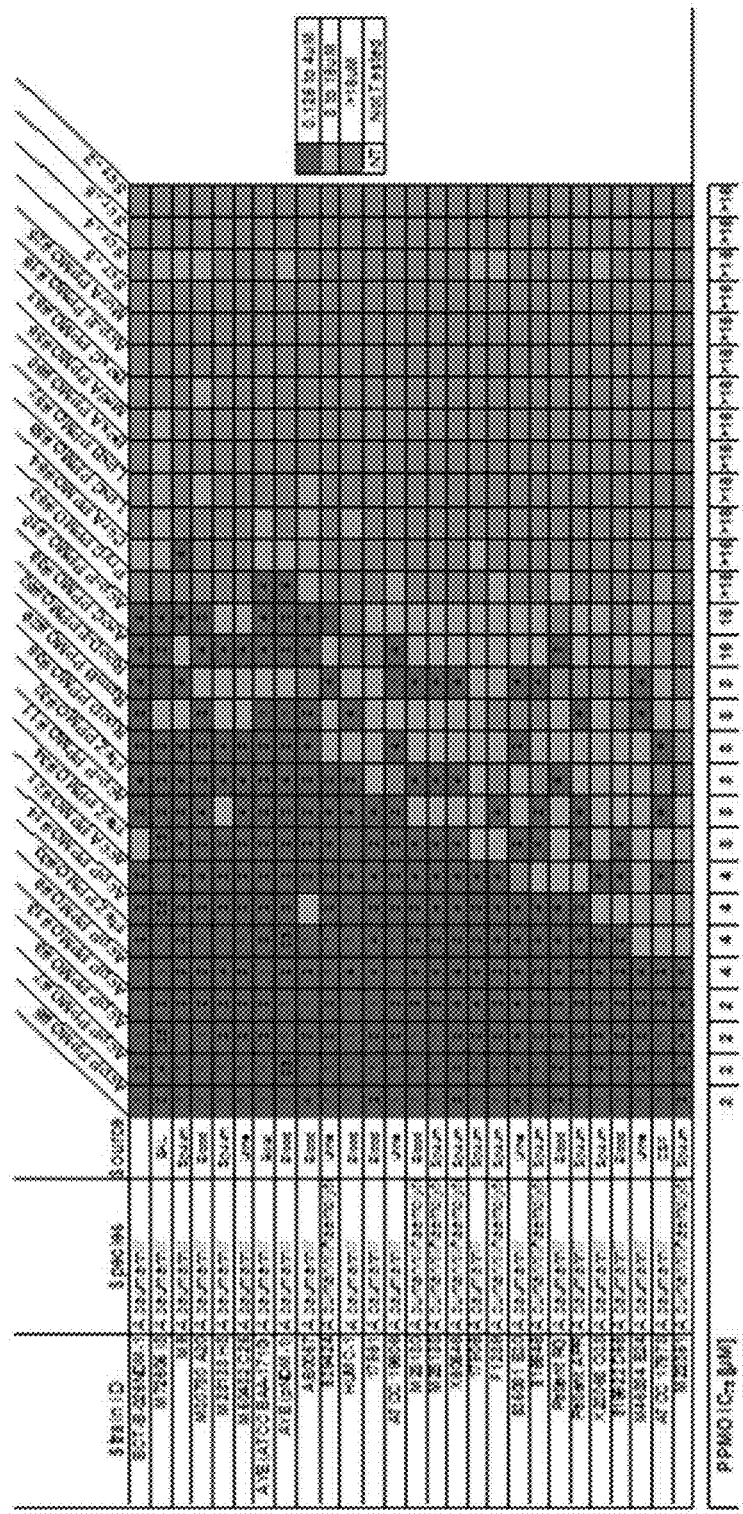

In *Acinetobacter*, acpP PPMOs #6 and #7 had IC$_{75}$ MICs of 2 to 4 μM, respectively, in nutrient rich MHII media. These PPMOs differed only in the positioning of the same peptide on the 5' (PPMO#6) or 3' (PPMO#7) end of the oligomer (FIG. 13C). As was seen in *E. coli*, *Acinetobacter* tested in minimal media increased the number of PPMOs that showed in vitro activity. Four additional acpP PPMOs were found to have activity along with the two that were active in MHII with IC$_{75}$ MICs ranging from 2 to 4 μM. Further gene targets were identified in AB minimal media including ftsZ (Cell division Z ring) with an IC$_{75}$ of 4 μM and accA (carboxyltransferase alpha subunit of acetyl Coenzyme A carboxylase) with an IC$_{75}$ of 4 μM (FIG. 13D).

Figure 9A:
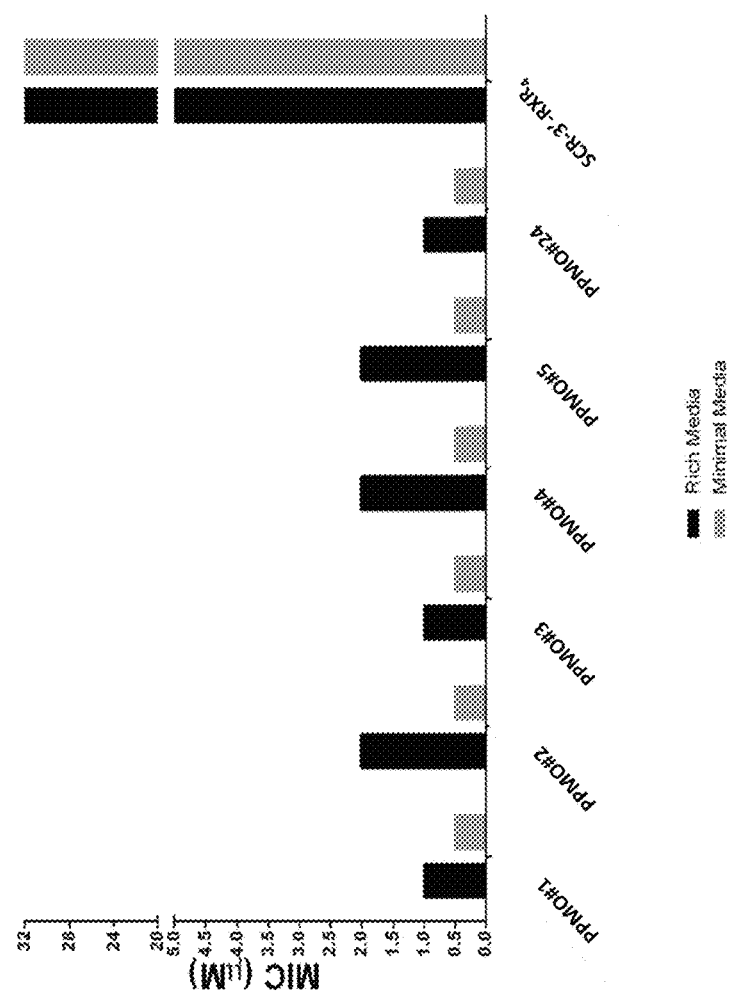
FIGS. 9A-9C show MIC comparisons of *E. coli* and *Acinetobacter* strains in rich and minimal media with various PPMOs and Scr controls.
Figure 9B:
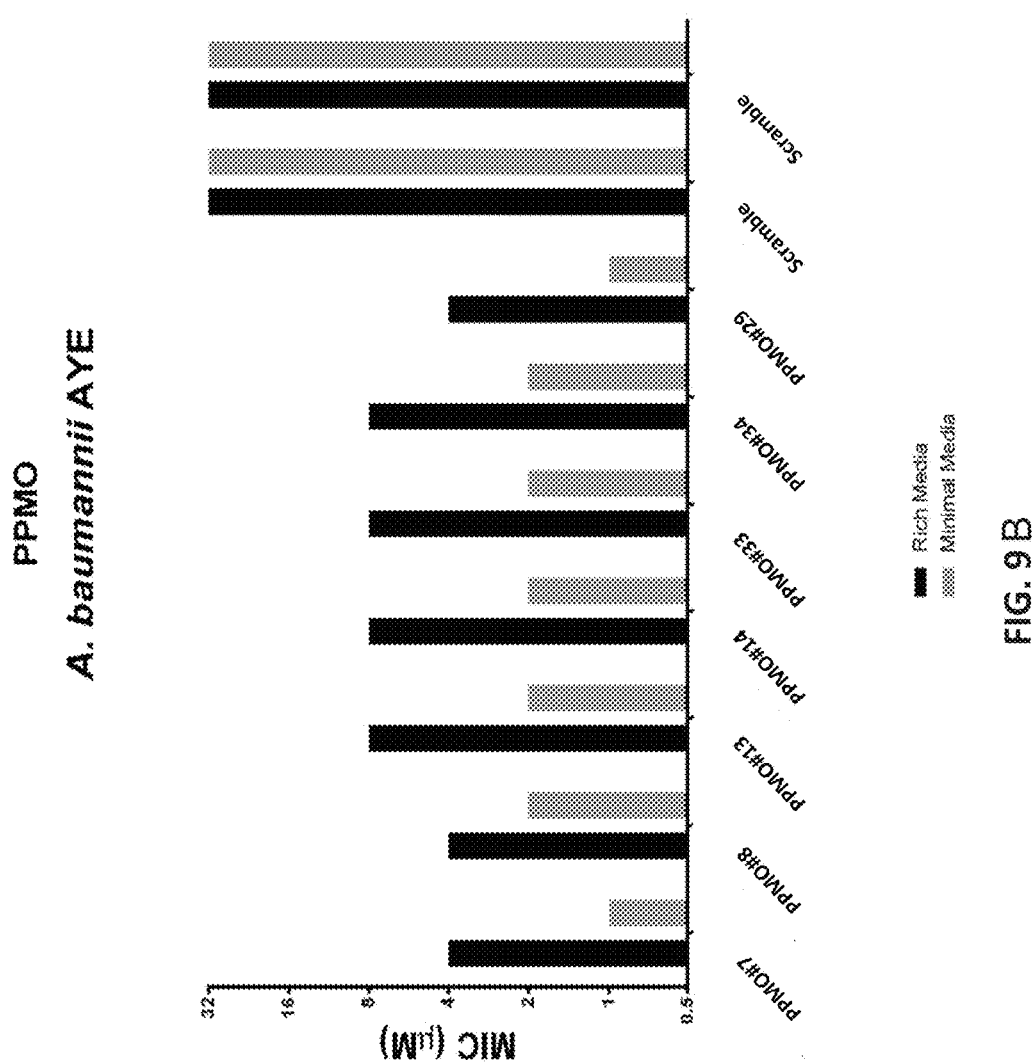
Figure 9C:
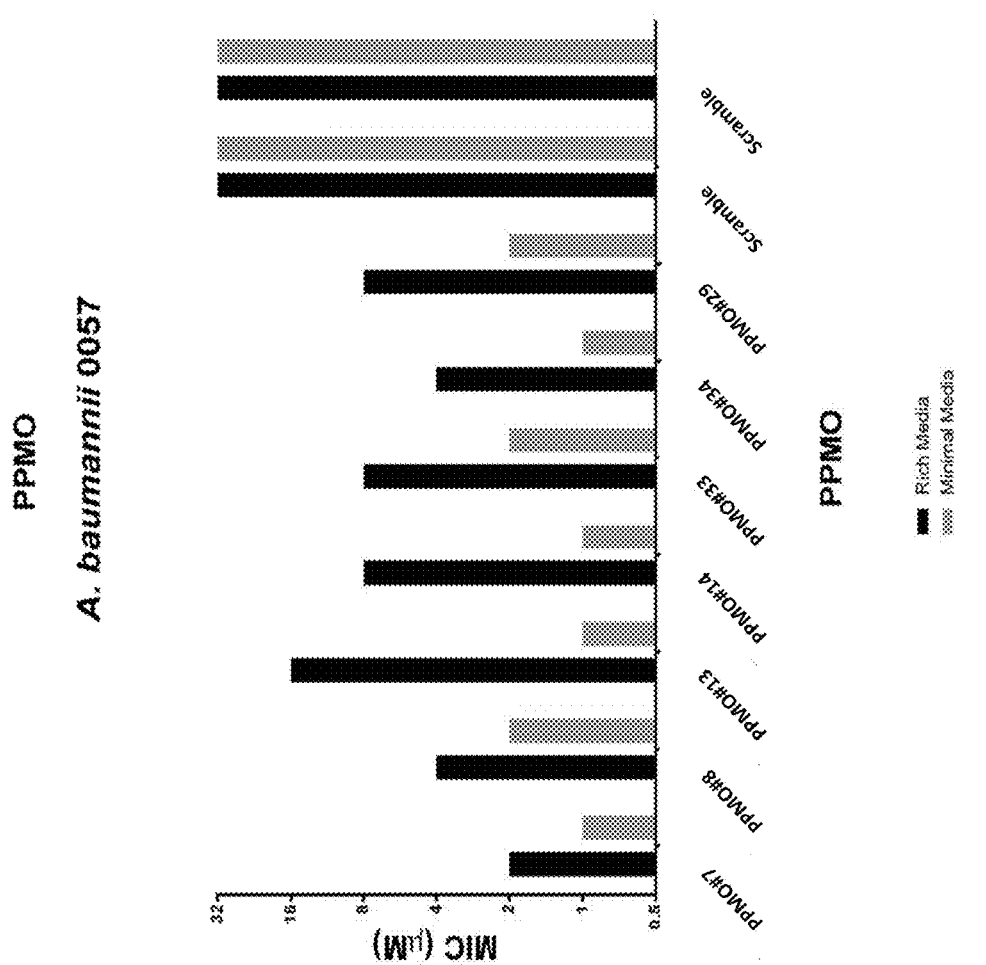
Figures 10A, 10B, 10C:
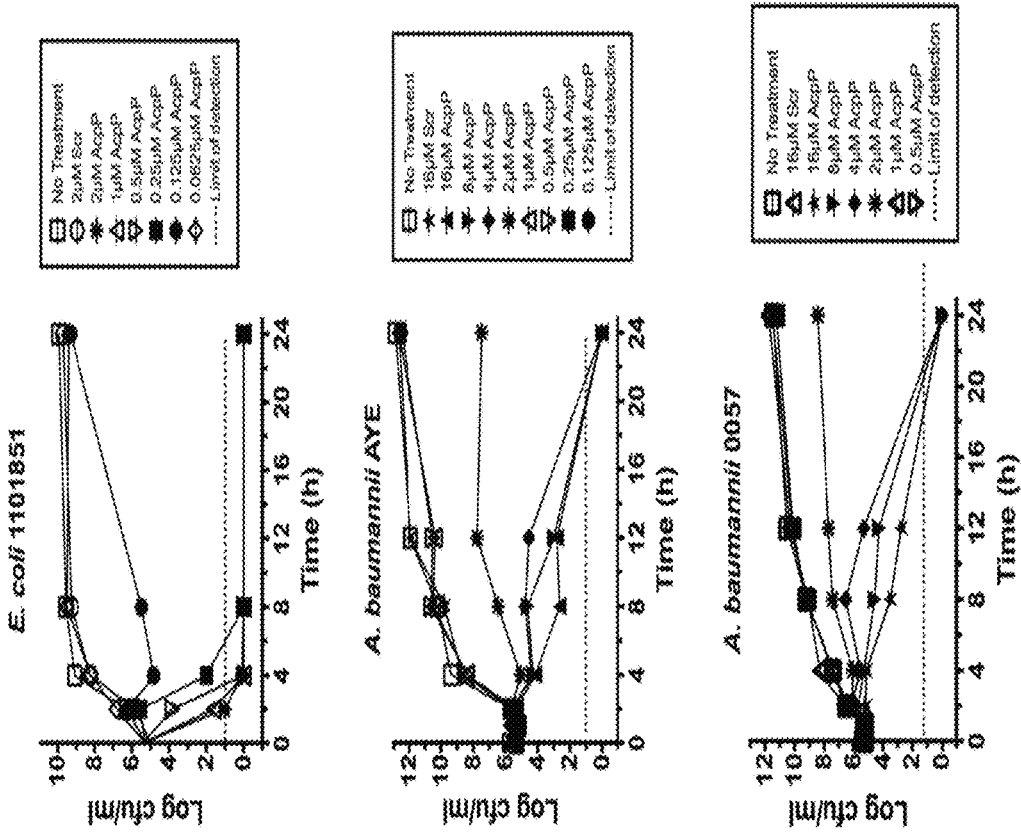
FIGS. 10A-10C show the kinetics of minimal bactericidal (MBC) viability assays on the growth of *E. coli* 1101851, *A. baumannii* AYE and 0057 upon challenge with PPMOs targeted against acpP. The cultures were grown aerobically at 37° C. with various concentrations of PPMO, as indicated. Samples were taken at the times noted, back-diluted 150 mM NaCl, and plated on blood agar. The plates were incubated for 18 hours and the resulting colony counts were used to determine the CFU/mL.

The enhanced activity of PPMOs in minimal media was maintained in MDR strains as well, with *E. coli* W3110 and *A. baumannii* AYE and 0057 having MIC values that were 1-2 fold lower when compared to rich media (see FIGS. 13A-D; FIGS. 9A-9C; FIGS. 10A-10C; and FIGS. 12A-12C).

FIG. 9A shows the results for *E. coli* W3110 challenged with acpP (PPMO#1), acpP (PPMO#2), acpP (PPMO#3), acpP (PPMO#4), acpP (PPMO#5), murA (PPMO#24), and Scramble (Scr) controls. FIGS. 9B-9C respectively shows the results for *A. baumannii* AYE (9B) and *A. baumannii* 0057 (9C) challenged with acpP (PPMO#7), acpP (PPMO#8), acpP (PPMO#13), acpP (PPMO#14), ftsZ (PPMO#33), ftsZ (PPMO#34), rpmB (PPMO#29), and Scramble (Scr) controls.

PPMOs were also bactericidal in multidrug-resistant (MDR) strains, as measured by kinetic MBC assays. The MDR strains *E. coli* 1101851, *A. baumannii* AYE, and *A. baumannii* 0057 were grown in the presence or absence of different concentrations of PPMOs and samples were plated at various time points to determine the amount of viable bacteria present (MBC assays, as described above). The results are shown in FIGS. 10A-10C. Despite being multidrug-resistant, PPMOs demonstrated both time and concentration dependent killing. By two hours, PPMOs at a concentration of 1 to 2 μM decreased viability by greater than 4 logs in *E. coli* 1101851 (FIG. 10A). By eight hours, all concentrations tested of 0.0625 μM or greater were bactericidal and below the limit of detection.

PPMOs also demonstrated both time and concentration dependent killing in *A. baumannii* strains AYE and AB0057, although with higher concentrations of PPMO and at a slower rate of kill than in *E. coli*. At 24 hours, the acpP-targeted PPMO (PPMO#7) was bactericidal and below the limit of detection at PPMO concentrations of >4 μM in both strains tested (FIGS. 10B-10C). A PPMO with a scrambled oligo sequence linked to the same peptide (Scr-(RXR)4) had no effect on any strain (FIG. 10A-10C).

There was also synergy between acpP-targeted PPMOs and three different antibiotics against the multidrug-resistant *E. coli* strain AIS070834 (see FIGS. 12A-12F). The MIC of colistin, meropenem, and tobramycin was measured with various concentrations of acpP-targeted PPMO (PPMO#1) or scrambled (Scr) control PPMO. Viable cells were counted in 24-hour cultures with antibiotic alone, PPMO alone, or in combination thereof. FIGS. 12A-12B show the results for colistin, FIGS. 12C-12D show the results for meropenem, and FIGS. 12E-12F show the results for tobramycin. In all instances, the acpP-targeted PPMO significantly reduced the MIC of the tested antibiotics. The free peptide (RXR)4XB was also tested and by itself had an unmeasurable MIC (data not shown).

Overall, these data show, inter alia, that PPMOs targeted against the acpP and other genes of *Acinetobacter* spp. and *E. coli*, including MDR strains, are bactericidal at clinically-relevant concentrations (e.g., IC$_{75}$ of 4 μM or less). These data also show PPMOs targeted against the acpP and other genes showed synergy with classic antibiotics tobramycin, meropenem and colistin, and restored the efficacy of those antibiotics in MDR strains of *Acinetobacter* and *Escherichia*. PPMOs could therefore be used either alone or synergistically with traditional antibiotics. When sub-inhibitory concentrations of the antibiotic were used in combination with a PPMO viability or growth of *A. baumannii* and *E. coli* was significantly reduced. For some antibiotics, such as colistin, the combination with PPMOs led to reduced viability by >3 logs.

Example 6

Effect of acpP-Targeted PPMO on *Acinetobacter* Cell Wall

Figures 11A, 11B, 11C, 11D, 11E, 11F, 11G, 11H, 11I, 11J, 11K, 11L:
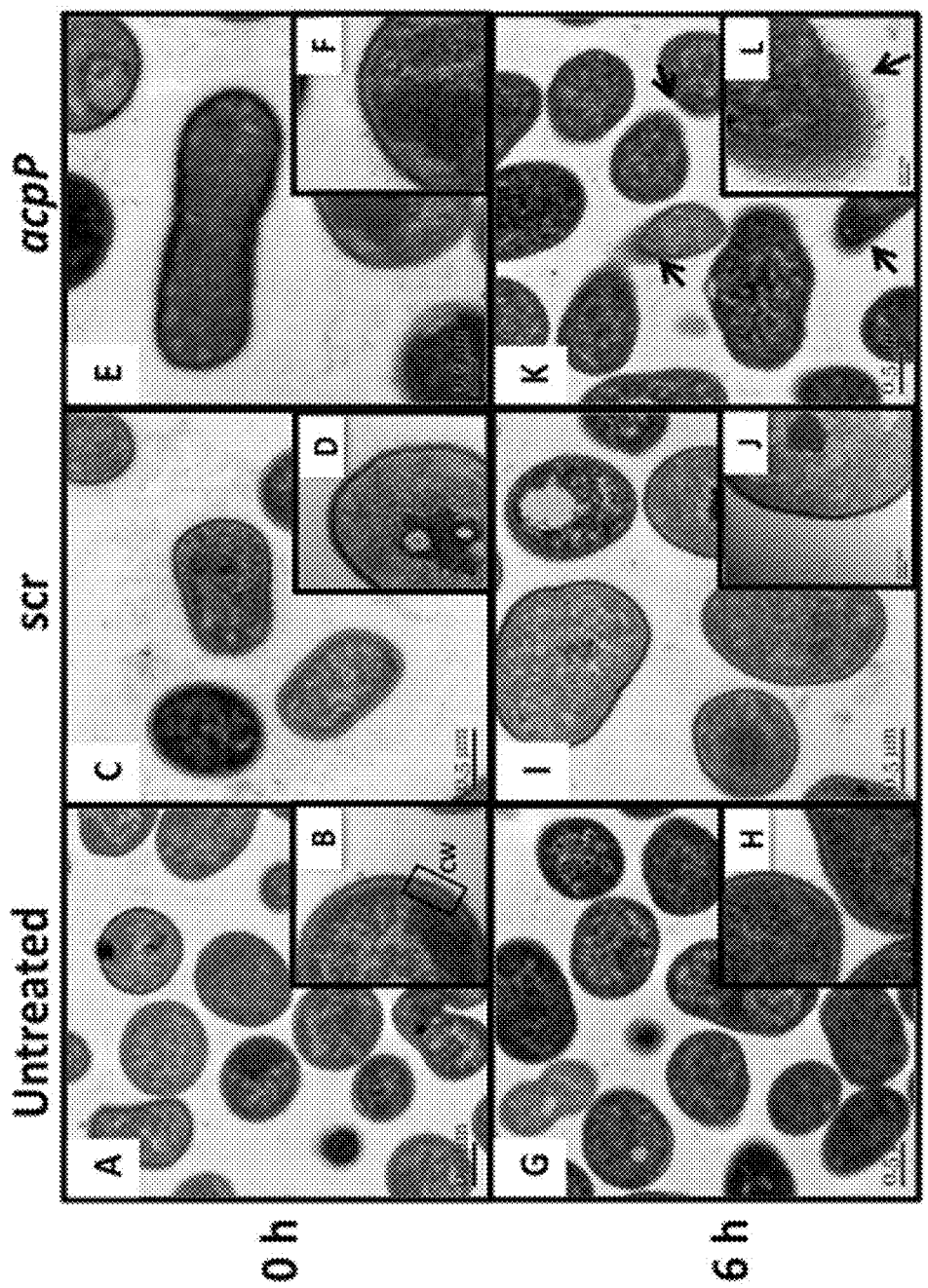
FIGS. 11A-11L show Transmission Electron Microscopy (TEM) of thin-sectioned *A. baumannii* AYE.

Transmission electron microscopy (TEM) was used to study the morphological alterations to *Acinetobacter* following challenge with acpP-targeted PPMOs. *A. baumannii* AYE was grown in nutrient rich MHII media (Mueller Hinton cation-adjusted broth; Becton-Dickinson Difco BBL, Franklin Lakes, N.J., USA) in the presence or absence of acpP PPMO (PPMO#7) or Scramble (Scr) PPMO control at a concentration of 40 μM. FIGS. 11A and 11B show *A. baumannii* AYE at 0 hour with an intact cell wall and cytoplasmic space in the absence of any PPMO. This was also true of AYE in the presence of Scr PPMO (FIGS. 11C-11D) and acpP PPMO (FIGS. 11E-11F) at 0 hour. After 6 hours of incubation, cells incubated with Scr PPMO (FIGS. 11I-11J) were indistinguishable from those of the untreated samples (FIGS. 11G-11H). In contrast, after 6 hours of incubation with the acpP-targeted PPMO, cell wall disruption was observed (FIGS. 11K-11L). This disruption was seen as early as 3 hours (data not shown). These results suggest that the reduction in *Acinetobacter* cell viability in the presence of Acp PPMO is due at least in part to the ability of the PPMO to cause cell wall damage.

Example 7

PPMOs are Synergistic in Combination with Traditional Antibiotics

To determine whether the combination of active PPMOs and traditional antibiotics were additive or synergistic in their effects, checkerboard MIC assays were performed. The multidrug resistant *E. coli* AIS070834 was incubated with increasing concentrations of ftsZ PPMO (PPMO#46) or scrambled (Scr) PPMO (Scr-1) and increasing concentrations of either colistin, meropenem or tobramycin.

In the presence of 2 μM of ftsZ PPMO, the MIC of colistin decreased from 0.5 μg/mL to 0.05 μg/mL (FIG. 14A). In addition, the MIC of meropenem decreased with increasing concentrations of ftsZ PPMO. In the absence of ftsZ PPMO the MIC of meropenem was 12 μg/mL, and this was reduced to 2 μg/mL when 4 μM ftsZ PPMO was present (FIG. 14C). This effect was not limited to antibiotics that affected bacterial membrane structure as synergy was also seen with the aminoglycoside tobramycin. In the absence of ftsZ PPMO, the MIC of tobramycin was 270 μg/mL. This was reduced to almost an undetectable level in the presence of 2 μM PPMO (FIG. 14E). For all antibiotics tested, there was a corresponding reduction in CFU/ml of at least 4 logs when ftsZ PPMO was combined with the antibiotic compared to either the PPMO or antibiotic alone (FIG. 14B, FIG. 14D, FIG. 14F). The scrambled PPMO at 32 µM or less, or free peptide (RXR)$_4$XB at 32 µM or less, showed no activity alone or synergy with the antibiotics tested.

Example 8

Figures 15A, 15B:
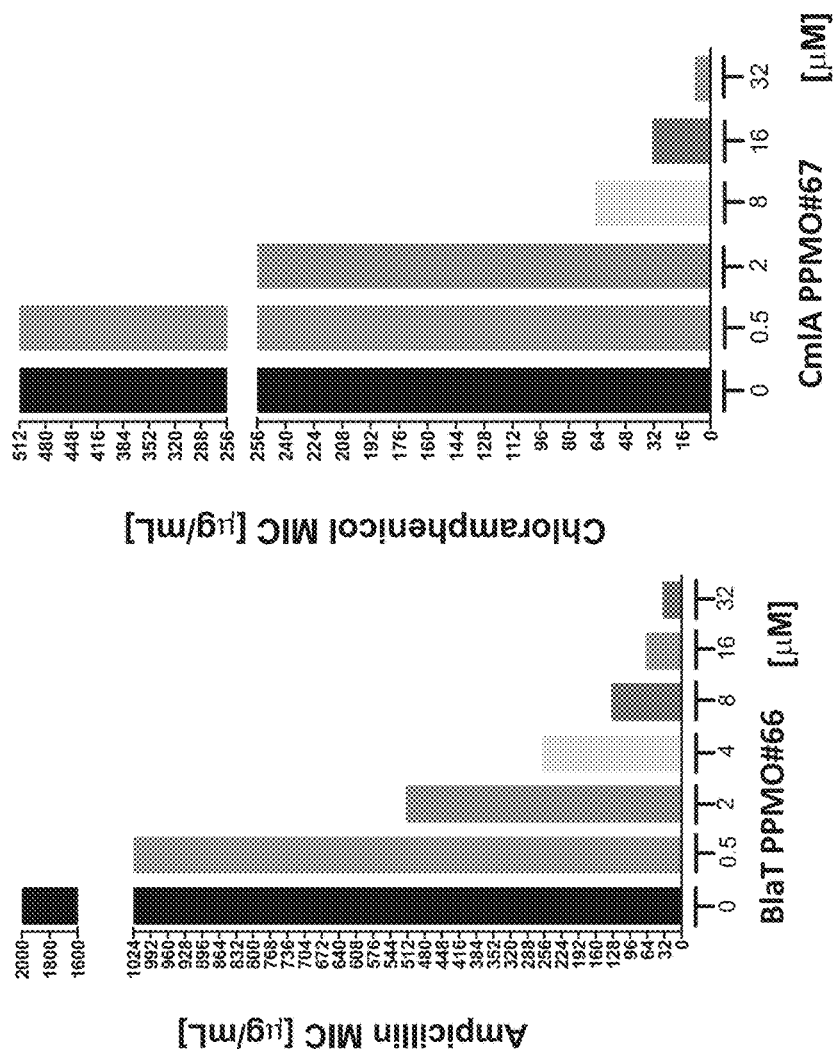
FIGS. 15A-15B show the minimum inhibitory concentration (MIC) of classical antibiotics with added PPMOs that target resistance genes in *E. coli* SMS-3-5.

PPMOs Targeted to Nonessential Antibiotic-resistance Genes Restore Susceptibility of MDR Strains to Traditional Antibiotics Modulating antibiotic resistance with PPMOs could be an alternative therapeutic strategy. As proof of concept, PPMOs were designed to target specific, non-essential antibiotic resistance genes. blaT is part of the TEM beta-lactamase family and is found in environmental strains of *E. coli*, like SMS-3-5. While SMS-3-5 is resistant to the beta-lactam ampicillin (MIC >1024 µg/mL), when incubated with increasing concentrations of a blaT PPMO (PPMO#66), the MIC progressively decreased (FIG. 15A). cmlA is an aminoglycoside resistance gene found in environmental *E. coli* strains. While SMS-3-5 is resistant to chloramphenicol (MIC >512 µg/mL), when incubated with increasing concentrations of a cmlA PPMO (PPMO#67), the MIC also progressively decreases in a dose-dependent fashion (FIG. 15B).

Figures 16A, 16B:
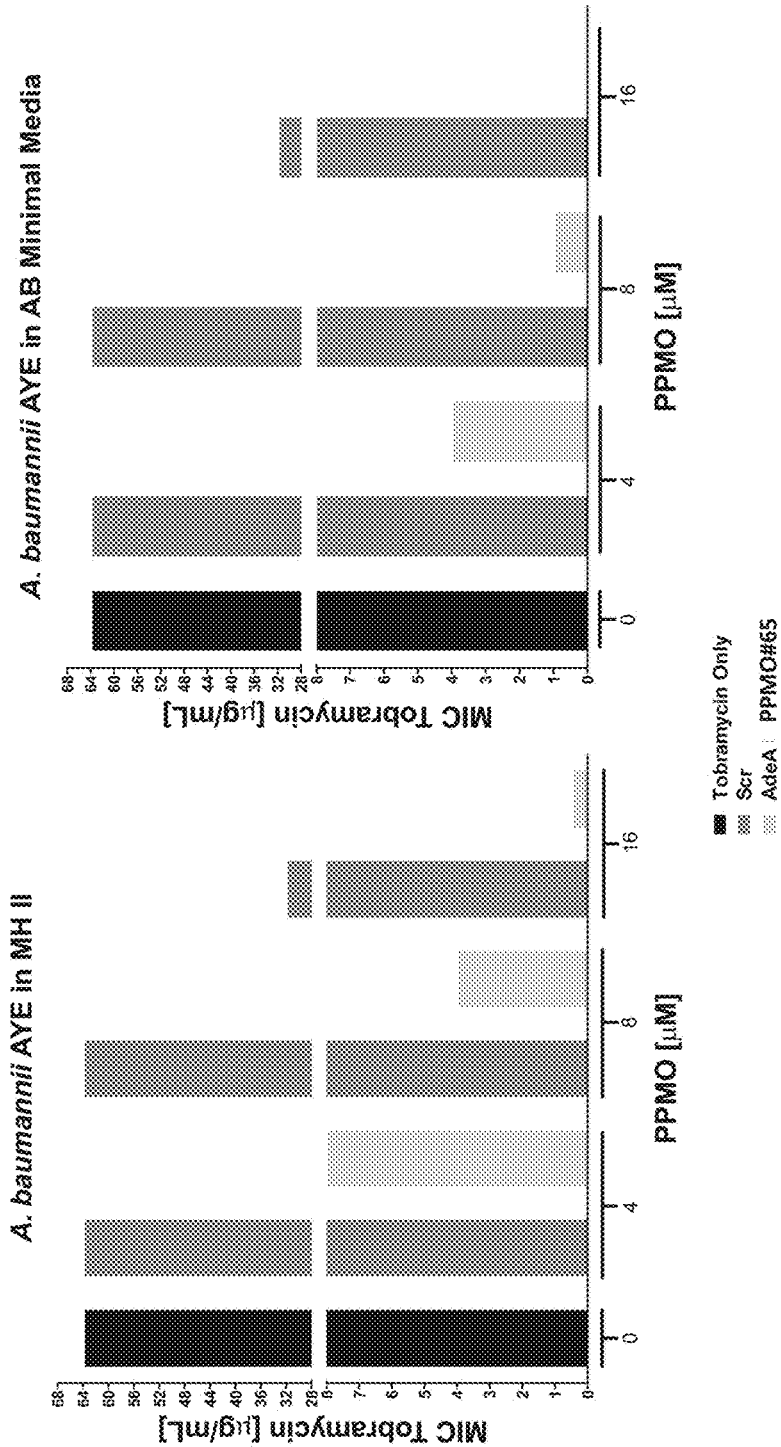
FIGS. 16A-16B show that PPMO mediated knockdown of nonessential resistance genes shows recovery of classical antibiotics efficacy. The graphs represent MICs performed by diluting PPMOs (adeA-(RXR)$_4$XB (PPMO#65); Scr-(RXR)$_4$ XB (Scr-2); and Peptide (RXR)$_4$XB, not shown) independently and with tobramycin in *A. baumannii* strain AYE in both (FIG. 16A) nutrient rich and (FIG. 16B) minimal medias. N=3.

To see whether blocking antibiotic resistance genes with PPMOs could be effective in other genera, *A. baumannii* AYE was incubated with a PPMO against adeA (PPMO#65), which encodes a component of the AdeABC RND-type multidrug efflux pump. AdeABC confers resistance to a variety of antibiotics including aminoglycosides. AYE was treated with varying concentrations of tobramycin and adeA PPMO in both MHII and AB Minimal Media. While tobramycin alone had an MIC of 64 µg/mL in both media, increasing concentrations of the adeA PPMO reduce the MIC of tobramycin significantly (FIG. 16A, FIG. 16B). With 8 µM adeA PPMO, the MIC of tobramycin was reduced to 4 µg/mL and 1 µg/mL in MHII and minimal media, respectively. A scrambled PPMO at 8 µM had no effect on the MIC of tobramycin.

SEQUENCE LISTING

```
<160> NUMBER OF SEQ ID NOS: 71

<210> SEQ ID NO 1
<211> LENGTH: 11
<212> TYPE: DNA
<213> ORGANISM: artificial
<220> FEATURE:
<223> OTHER INFORMATION: acpP targeting sequence

<400> SEQUENCE: 1
cttcgatagt g                                                          11

<210> SEQ ID NO 2
<211> LENGTH: 11
<212> TYPE: DNA
<213> ORGANISM: artificial
<220> FEATURE:
<223> OTHER INFORMATION: acpP targeting sequence

<400> SEQUENCE: 2
atatcgctca c                                                          11

<210> SEQ ID NO 3
<211> LENGTH: 11
<212> TYPE: DNA
<213> ORGANISM: artificial
<220> FEATURE:
<223> OTHER INFORMATION: acpP targeting sequence

<400> SEQUENCE: 3
attctcctca t                                                          11

<210> SEQ ID NO 4
<211> LENGTH: 11
<212> TYPE: DNA
<213> ORGANISM: artificial
<220> FEATURE:
<223> OTHER INFORMATION: acpP targeting sequence

<400> SEQUENCE: 4
cacaggaatt c                                                          11

<210> SEQ ID NO 5
```

```
<211> LENGTH: 11
<212> TYPE: DNA
<213> ORGANISM: artificial
<220> FEATURE:
<223> OTHER INFORMATION: acpS targeting sequence

<400> SEQUENCE: 5
ttgccattag c                                                            11

<210> SEQ ID NO 6
<211> LENGTH: 17
<212> TYPE: DNA
<213> ORGANISM: artificial
<220> FEATURE:
<223> OTHER INFORMATION: acp-E targeting sequence

<400> SEQUENCE: 6
ctgtagtgat ttcacca                                                      17

<210> SEQ ID NO 7
<211> LENGTH: 11
<212> TYPE: DNA
<213> ORGANISM: artificial
<220> FEATURE:
<223> OTHER INFORMATION: fabA targeting sequence

<400> SEQUENCE: 7
ttatctacca t                                                            11

<210> SEQ ID NO 8
<211> LENGTH: 11
<212> TYPE: DNA
<213> ORGANISM: artificial
<220> FEATURE:
<223> OTHER INFORMATION: fabB targeting sequence

<400> SEQUENCE: 8
gcacgtttca t                                                            11

<210> SEQ ID NO 9
<211> LENGTH: 11
<212> TYPE: DNA
<213> ORGANISM: artificial
<220> FEATURE:
<223> OTHER INFORMATION: fabI targeting sequence

<400> SEQUENCE: 9
agaaaaccca t                                                            11

<210> SEQ ID NO 10
<211> LENGTH: 11
<212> TYPE: DNA
<213> ORGANISM: artificial
<220> FEATURE:
<223> OTHER INFORMATION: gapA targeting sequence

<400> SEQUENCE: 10
ttgatagtca t                                                            11

<210> SEQ ID NO 11
<211> LENGTH: 11
<212> TYPE: DNA
<213> ORGANISM: artificial
<220> FEATURE:
<223> OTHER INFORMATION: accA targeting sequence

<400> SEQUENCE: 11
```
gcttttttca t          11

<210> SEQ ID NO 12
<211> LENGTH: 11
<212> TYPE: DNA
<213> ORGANISM: artificial
<220> FEATURE:
<223> OTHER INFORMATION: murA targeting sequence

<400> SEQUENCE: 12
atccatttag t          11

<210> SEQ ID NO 13
<211> LENGTH: 11
<212> TYPE: DNA
<213> ORGANISM: artificial
<220> FEATURE:
<223> OTHER INFORMATION: murA targeting sequence

<400> SEQUENCE: 13
catttagttt g          11

<210> SEQ ID NO 14
<211> LENGTH: 11
<212> TYPE: DNA
<213> ORGANISM: artificial
<220> FEATURE:
<223> OTHER INFORMATION: murA targeting sequence

<400> SEQUENCE: 14
aatttatcca t          11

<210> SEQ ID NO 15
<211> LENGTH: 11
<212> TYPE: DNA
<213> ORGANISM: artificial
<220> FEATURE:
<223> OTHER INFORMATION: murA targeting sequence

<400> SEQUENCE: 15
aaatttatcc a          11

<210> SEQ ID NO 16
<211> LENGTH: 11
<212> TYPE: DNA
<213> ORGANISM: artificial
<220> FEATURE:
<223> OTHER INFORMATION: rpmB targeting sequence

<400> SEQUENCE: 16
actcgggaca t          11

<210> SEQ ID NO 17
<211> LENGTH: 11
<212> TYPE: DNA
<213> ORGANISM: artificial
<220> FEATURE:
<223> OTHER INFORMATION: rpmB targeting sequence

<400> SEQUENCE: 17
ctattctcca a          11

<210> SEQ ID NO 18
<211> LENGTH: 11
<212> TYPE: DNA

```
<213> ORGANISM: artificial
<220> FEATURE:
<223> OTHER INFORMATION: rpmB targeting sequence

<400> SEQUENCE: 18
ggcagactcg g                                                          11

<210> SEQ ID NO 19
<211> LENGTH: 11
<212> TYPE: DNA
<213> ORGANISM: artificial
<220> FEATURE:
<223> OTHER INFORMATION: rpmB targeting sequence

<400> SEQUENCE: 19
cttagacatg g                                                          11

<210> SEQ ID NO 20
<211> LENGTH: 11
<212> TYPE: DNA
<213> ORGANISM: artificial
<220> FEATURE:
<223> OTHER INFORMATION: adk targeting sequence

<400> SEQUENCE: 20
atgatacgca t                                                          11

<210> SEQ ID NO 21
<211> LENGTH: 11
<212> TYPE: DNA
<213> ORGANISM: artificial
<220> FEATURE:
<223> OTHER INFORMATION: infA targeting sequence

<400> SEQUENCE: 21
tctttggcca t                                                          11

<210> SEQ ID NO 22
<211> LENGTH: 11
<212> TYPE: DNA
<213> ORGANISM: artificial
<220> FEATURE:
<223> OTHER INFORMATION: ftsZ targeting sequence

<400> SEQUENCE: 22
tcaaatgagg c                                                          11

<210> SEQ ID NO 23
<211> LENGTH: 11
<212> TYPE: DNA
<213> ORGANISM: artificial
<220> FEATURE:
<223> OTHER INFORMATION: ftsZ targeting sequence

<400> SEQUENCE: 23
aatgaggcca t                                                          11

<210> SEQ ID NO 24
<211> LENGTH: 13
<212> TYPE: DNA
<213> ORGANISM: artificial
<220> FEATURE:
<223> OTHER INFORMATION: ftsZ targeting sequence

<400> SEQUENCE: 24
atagtttctc tcc                                                        13
```

<210> SEQ ID NO 25
<211> LENGTH: 11
<212> TYPE: DNA
<213> ORGANISM: artificial
<220> FEATURE:
<223> OTHER INFORMATION: rpoD targeting sequence

<400> SEQUENCE: 25
tcatctttgc t                                                            11

<210> SEQ ID NO 26
<211> LENGTH: 11
<212> TYPE: DNA
<213> ORGANISM: artificial
<220> FEATURE:
<223> OTHER INFORMATION: rpoD targeting sequence

<400> SEQUENCE: 26
ttttgctcca t                                                            11

<210> SEQ ID NO 27
<211> LENGTH: 11
<212> TYPE: DNA
<213> ORGANISM: artificial
<220> FEATURE:
<223> OTHER INFORMATION: aroC targeting sequence

<400> SEQUENCE: 27
ttccctgcca t                                                            11

<210> SEQ ID NO 28
<211> LENGTH: 11
<212> TYPE: DNA
<213> ORGANISM: artificial
<220> FEATURE:
<223> OTHER INFORMATION: aroC targeting sequence

<400> SEQUENCE: 28
tttccagcca t                                                            11

<210> SEQ ID NO 29
<211> LENGTH: 11
<212> TYPE: DNA
<213> ORGANISM: artificial
<220> FEATURE:
<223> OTHER INFORMATION: murF targeting sequence

<400> SEQUENCE: 29
acgctaatca t                                                            11

<210> SEQ ID NO 30
<211> LENGTH: 11
<212> TYPE: DNA
<213> ORGANISM: artificial
<220> FEATURE:
<223> OTHER INFORMATION: lpxC targeting sequence

<400> SEQUENCE: 30
tgtttgatca t                                                            11

<210> SEQ ID NO 31
<211> LENGTH: 11
<212> TYPE: DNA
<213> ORGANISM: artificial
<220> FEATURE:

<223> OTHER INFORMATION: kdtA targeting sequence

<400> SEQUENCE: 31
aattcgagca t                                                                 11

<210> SEQ ID NO 32
<211> LENGTH: 11
<212> TYPE: DNA
<213> ORGANISM: artificial
<220> FEATURE:
<223> OTHER INFORMATION: boxA targeting sequence

<400> SEQUENCE: 32
tgttaaagag c                                                                 11

<210> SEQ ID NO 33
<211> LENGTH: 15
<212> TYPE: DNA
<213> ORGANISM: artificial
<220> FEATURE:
<223> OTHER INFORMATION: rpoD-E targeting sequence

<400> SEQUENCE: 33
cttgtaacca cacca                                                             15

<210> SEQ ID NO 34
<211> LENGTH: 11
<212> TYPE: DNA
<213> ORGANISM: artificial
<220> FEATURE:
<223> OTHER INFORMATION: pryC targeting sequence

<400> SEQUENCE: 34
ggtgcagtca t                                                                 11

<210> SEQ ID NO 35
<211> LENGTH: 11
<212> TYPE: DNA
<213> ORGANISM: artificial
<220> FEATURE:
<223> OTHER INFORMATION: pryA targeting sequence

<400> SEQUENCE: 35
gacttaatca a                                                                 11

<210> SEQ ID NO 36
<211> LENGTH: 11
<212> TYPE: DNA
<213> ORGANISM: artificial
<220> FEATURE:
<223> OTHER INFORMATION: lgt targeting sequence

<400> SEQUENCE: 36
ctactggtca t                                                                 11

<210> SEQ ID NO 37
<211> LENGTH: 11
<212> TYPE: DNA
<213> ORGANISM: artificial
<220> FEATURE:
<223> OTHER INFORMATION: folA targeting sequence

<400> SEQUENCE: 37
cattgagatt t                                                                 11

```
<210> SEQ ID NO 38
<211> LENGTH: 11
<212> TYPE: DNA
<213> ORGANISM: artificial
<220> FEATURE:
<223> OTHER INFORMATION: infB targeting sequence

<400> SEQUENCE: 38
acatctgtca t                                                        11

<210> SEQ ID NO 39
<211> LENGTH: 11
<212> TYPE: DNA
<213> ORGANISM: artificial
<220> FEATURE:
<223> OTHER INFORMATION: nrdA targeting sequence

<400> SEQUENCE: 39
ttctgattca t                                                        11

<210> SEQ ID NO 40
<211> LENGTH: 11
<212> TYPE: DNA
<213> ORGANISM: artificial
<220> FEATURE:
<223> OTHER INFORMATION: nrdB targeting sequence

<400> SEQUENCE: 40
gtatatgcca t                                                        11

<210> SEQ ID NO 41
<211> LENGTH: 11
<212> TYPE: DNA
<213> ORGANISM: artificial
<220> FEATURE:
<223> OTHER INFORMATION: zipA targeting sequence

<400> SEQUENCE: 41
tcctgcatca t                                                        11

<210> SEQ ID NO 42
<211> LENGTH: 11
<212> TYPE: DNA
<213> ORGANISM: artificial
<220> FEATURE:
<223> OTHER INFORMATION: coaA targeting sequence

<400> SEQUENCE: 42
atatacctca t                                                        11

<210> SEQ ID NO 43
<211> LENGTH: 17
<212> TYPE: DNA
<213> ORGANISM: artificial
<220> FEATURE:
<223> OTHER INFORMATION: gyrA-E targeting sequence

<400> SEQUENCE: 43
gttaccctga ccgacca                                                  17

<210> SEQ ID NO 44
<211> LENGTH: 16
<212> TYPE: DNA
<213> ORGANISM: artificial
<220> FEATURE:
<223> OTHER INFORMATION: gyrA-E targeting sequence
```

```
<400> SEQUENCE: 44
gttaccctga ccacca                                                    16

<210> SEQ ID NO 45
<211> LENGTH: 11
<212> TYPE: DNA
<213> ORGANISM: artificial
<220> FEATURE:
<223> OTHER INFORMATION: mrdA targeting sequence

<400> SEQUENCE: 45
tgtttcatac g                                                         11

<210> SEQ ID NO 46
<211> LENGTH: 11
<212> TYPE: DNA
<213> ORGANISM: artificial
<220> FEATURE:
<223> OTHER INFORMATION: lpxB targeting sequence

<400> SEQUENCE: 46
ggtttgccaa g                                                         11

<210> SEQ ID NO 47
<211> LENGTH: 11
<212> TYPE: DNA
<213> ORGANISM: artificial
<220> FEATURE:
<223> OTHER INFORMATION: lpxC targeting sequence

<400> SEQUENCE: 47
tgtttcacca t                                                         11

<210> SEQ ID NO 48
<211> LENGTH: 11
<212> TYPE: DNA
<213> ORGANISM: artificial
<220> FEATURE:
<223> OTHER INFORMATION: kdtA targeting sequence
<220> FEATURE:
<221> NAME/KEY: misc_feature
<222> LOCATION: (1)..(1)
<223> OTHER INFORMATION: I
<220> FEATURE:
<221> NAME/KEY: misc_feature
<222> LOCATION: (2)..(2)
<223> OTHER INFORMATION: I
<220> FEATURE:
<221> NAME/KEY: misc_feature
<222> LOCATION: (3)..(3)
<223> OTHER INFORMATION: I
<220> FEATURE:
<221> NAME/KEY: misc_feature
<222> LOCATION: (4)..(4)
<223> OTHER INFORMATION: I

<400> SEQUENCE: 48
nnnntcgcca a                                                         11

<210> SEQ ID NO 49
<211> LENGTH: 11
<212> TYPE: DNA
<213> ORGANISM: artificial
<220> FEATURE:
<223> OTHER INFORMATION: boxA targeting sequence

<400> SEQUENCE: 49
ctcttaatga t                                                         11
```

```
<210> SEQ ID NO 50
<211> LENGTH: 11
<212> TYPE: DNA
<213> ORGANISM: artificial
<220> FEATURE:
<223> OTHER INFORMATION: boxC targeting sequence

<400> SEQUENCE: 50
atccacacaa g                                                          11

<210> SEQ ID NO 51
<211> LENGTH: 15
<212> TYPE: DNA
<213> ORGANISM: artificial
<220> FEATURE:
<223> OTHER INFORMATION: rpoD-E targeting sequence

<400> SEQUENCE: 51
tccaccaagt cacca                                                      15

<210> SEQ ID NO 52
<211> LENGTH: 11
<212> TYPE: DNA
<213> ORGANISM: artificial
<220> FEATURE:
<223> OTHER INFORMATION: pryC targeting sequence

<400> SEQUENCE: 52
agagttcaag g                                                          11

<210> SEQ ID NO 53
<211> LENGTH: 11
<212> TYPE: DNA
<213> ORGANISM: artificial
<220> FEATURE:
<223> OTHER INFORMATION: carA targeting sequence

<400> SEQUENCE: 53
ggtgctcaaa c                                                          11

<210> SEQ ID NO 54
<211> LENGTH: 11
<212> TYPE: DNA
<213> ORGANISM: artificial
<220> FEATURE:
<223> OTHER INFORMATION: adeA targeting sequence

<400> SEQUENCE: 54
atactgtcca a                                                          11

<210> SEQ ID NO 55
<211> LENGTH: 11
<212> TYPE: DNA
<213> ORGANISM: artificial
<220> FEATURE:
<223> OTHER INFORMATION: blaT targeting sequence

<400> SEQUENCE: 55 ctcttcctttt t                                                         11

<210> SEQ ID NO 56
<211> LENGTH: 11
<212> TYPE: DNA
<213> ORGANISM: artificial
<220> FEATURE:
```

<223> OTHER INFORMATION: cml targeting sequence

<400> SEQUENCE: 56
tccttctgat t                                                                        11

<210> SEQ ID NO 57
<211> LENGTH: 12
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (2)..(2)
<223> OTHER INFORMATION: Acp
<220> FEATURE:
<221> NAME/KEY: MOD_RES
<222> LOCATION: (5)..(5)
<223> OTHER INFORMATION: Acp
<220> FEATURE:
<221> NAME/KEY: MOD_RES
<222> LOCATION: (8)..(8)
<223> OTHER INFORMATION: Acp
<220> FEATURE:
<221> NAME/KEY: MOD_RES
<222> LOCATION: (11)..(11)
<223> OTHER INFORMATION: Acp

<400> SEQUENCE: 57

Arg Xaa Arg Arg Xaa Arg Arg Xaa Arg Arg Xaa Arg
1               5                   10

<210> SEQ ID NO 58
<211> LENGTH: 10
<212> TYPE: PRT
<213> ORGANISM: artificial
<220> FEATURE:
<223> OTHER INFORMATION: CPP sequence

<400> SEQUENCE: 58

Arg Phe Phe Arg Phe Phe Arg Phe Phe Arg
1               5                   10

<210> SEQ ID NO 59
<211> LENGTH: 14
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (2)..(2)
<223> OTHER INFORMATION: Acp
<220> FEATURE:
<221> NAME/KEY: MOD_RES
<222> LOCATION: (5)..(5)
<223> OTHER INFORMATION: Acp
<220> FEATURE:
<221> NAME/KEY: MOD_RES
<222> LOCATION: (8)..(8)
<223> OTHER INFORMATION: Acp
<220> FEATURE:
<221> NAME/KEY: MOD_RES
<222> LOCATION: (11)..(11)
<223> OTHER INFORMATION: Acp
<220> FEATURE:
<221> NAME/KEY: MOD_RES
<222> LOCATION: (13)..(13)
<223> OTHER INFORMATION: Acp
<220> FEATURE:
<221> NAME/KEY: MOD_RES
<222> LOCATION: (14)..(14)
<223> OTHER INFORMATION: bAla

<400> SEQUENCE: 59

Arg Xaa Arg Arg Xaa Arg Arg Xaa Arg Xaa Xaa Xaa
1               5                   10

<210> SEQ ID NO 60
<211> LENGTH: 12
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (11)..(11)
<223> OTHER INFORMATION: Acp
<220> FEATURE:
<221> NAME/KEY: MOD_RES
<222> LOCATION: (12)..(12)
<223> OTHER INFORMATION: bAla

<400> SEQUENCE: 60

Arg Phe Phe Arg Phe Phe Arg Phe Phe Arg Xaa Xaa
1               5                   10

<210> SEQ ID NO 61
<211> LENGTH: 12
<212> TYPE: PRT
<213> ORGANISM: artificial
<220> FEATURE:
<223> OTHER INFORMATION: CPP sequence

<400> SEQUENCE: 61

Arg Phe Arg Arg Phe Arg Arg Phe Arg Arg Phe Arg
1               5                   10

<210> SEQ ID NO 62
<211> LENGTH: 12
<212> TYPE: PRT
<213> ORGANISM: artificial
<220> FEATURE:
<223> OTHER INFORMATION: CPP sequence

<400> SEQUENCE: 62

Arg Tyr Arg Arg Tyr Arg Arg Tyr Arg Arg Tyr Arg
1               5                   10

<210> SEQ ID NO 63
<211> LENGTH: 12
<212> TYPE: PRT
<213> ORGANISM: artificial
<220> FEATURE:
<223> OTHER INFORMATION: CPP sequence

<400> SEQUENCE: 63

Arg Gly Arg Arg Gly Arg Arg Gly Arg Arg Gly Arg
1               5                   10

<210> SEQ ID NO 64
<211> LENGTH: 14
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (13)..(13)
<223> OTHER INFORMATION: Acp
<220> FEATURE:
<221> NAME/KEY: MOD_RES

```
<222> LOCATION: (14)..(14)
<223> OTHER INFORMATION: bAla

<400> SEQUENCE: 64

Arg Phe Arg Arg Phe Arg Arg Phe Arg Arg Phe Arg Xaa Xaa
1               5                   10

<210> SEQ ID NO 65
<211> LENGTH: 14
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (13)..(13)
<223> OTHER INFORMATION: Acp
<220> FEATURE:
<221> NAME/KEY: MOD_RES
<222> LOCATION: (14)..(14)
<223> OTHER INFORMATION: bAla

<400> SEQUENCE: 65

Arg Tyr Arg Arg Tyr Arg Arg Tyr Arg Arg Tyr Arg Xaa Xaa
1               5                   10

<210> SEQ ID NO 66
<211> LENGTH: 14
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (13)..(13)
<223> OTHER INFORMATION: Acp
<220> FEATURE:
<221> NAME/KEY: MOD_RES
<222> LOCATION: (14)..(14)
<223> OTHER INFORMATION: bAla

<400> SEQUENCE: 66

Arg Gly Arg Arg Gly Arg Arg Gly Arg Arg Gly Arg Xaa Xaa
1               5                   10

<210> SEQ ID NO 67
<211> LENGTH: 12
<212> TYPE: PRT
<213> ORGANISM: artificial
<220> FEATURE:
<223> OTHER INFORMATION: CPP sequence
<220> FEATURE:
<221> NAME/KEY: MOD_RES
<222> LOCATION: (11)..(11)
<223> OTHER INFORMATION: Acp
<220> FEATURE:
<221> NAME/KEY: MOD_RES
<222> LOCATION: (12)..(12)
<223> OTHER INFORMATION: bAla

<400> SEQUENCE: 67

Arg Phe Phe Arg Phe Phe Arg Phe Phe Arg Xaa Xaa
1               5                   10

<210> SEQ ID NO 68
<211> LENGTH: 11
<212> TYPE: PRT
<213> ORGANISM: artificial
<220> FEATURE:
<223> OTHER INFORMATION: CPP sequence
```

```
<400> SEQUENCE: 68

Arg Phe Phe Arg Phe Phe Arg Phe Phe Arg Gly
1               5                   10

<210> SEQ ID NO 69
<211> LENGTH: 60
<212> TYPE: DNA
<213> ORGANISM: Escherichia coli

<400> SEQUENCE: 69
aaagcgagtt ttgataggaa atttaagagt atgagcacta tcgaagaacg cgttaagaaa    60

<210> SEQ ID NO 70
<211> LENGTH: 90
<212> TYPE: DNA
<213> ORGANISM: Acinetobacter baumannii

<400> SEQUENCE: 70
ttttaaaaat ttttatattc aattaaacta gtggcaaatc aaacgccaca agcaatgagg    60
agaattcctg tgagcgatat cgaacaacgc                                     90

<210> SEQ ID NO 71
<211> LENGTH: 11
<212> TYPE: DNA
<213> ORGANISM: artificial
<220> FEATURE:
<223> OTHER INFORMATION: scramble targeting sequence

<400> SEQUENCE: 71
tctcagatgg t                                                         11
```

The invention claimed is:

1. An antisense morpholino oligomer of formula (I):

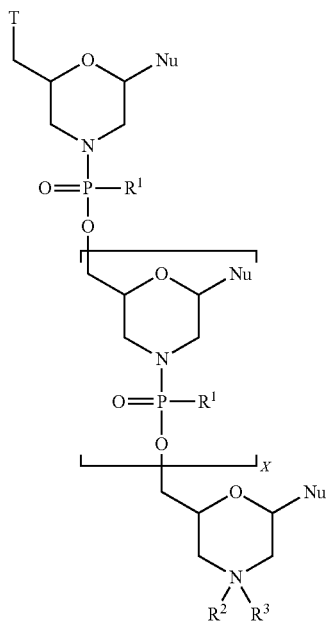

or a pharmaceutically acceptable salt thereof,
where each Nu is a nucleobase which taken together forms a targeting sequence, where the targeting sequence is set forth in SEQ ID NOS: 2-11, comprises a fragment of at least 10 contiguous nucleotides of SEQ ID NOS: 2-11, or comprises a variant having at least 80% sequence identity to SEQ ID NOS: 2-11, where thymine bases (T) are optionally uracil bases (U);

X is an integer from 9 to 38;

T is selected from OH and a moiety of the formula:

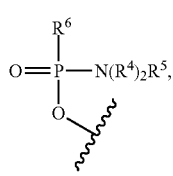

where each $R^4$ is independently $C_1$-$C_6$ alkyl, and $R^5$ is selected from an electron pair and H, and $R^6$ is selected from OH, —N($R^7$)CH$_2$C(O)NH$_2$, and a moiety of the formula:

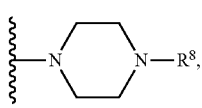

where
$R^7$ is selected from H and $C_1$-$C_6$ alkyl; and
$R^8$ is selected from G, —C(O)$R^9$OH, acyl, trityl, and 4-methoxytrityl, where:

R⁹ is of the formula —(O-alkyl)ᵧ- where y is an integer from 3 to 10 and each of the y alkyl groups is independently selected from $C_2$-$C_6$ alkyl;

each of $R^1$ is $=N(R^{10})_2R^{11}$ where each $R^{10}$ is independently $C_1$-$C_6$ alkyl, and $R^{11}$ is selected from an electron pair and H;

$R^2$ is selected from H, G, acyl, trityl, 4-methoxytrityl, benzoyl, stearoyl, and a moiety of the formula:

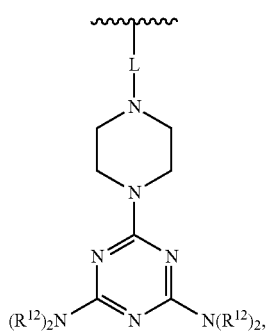

where L is selected from —C(O)(CH₂)₆C(O)— and —C(O)(CH₂)₂S₂(CH₂)₂C(O)—, and each $R^{12}$ is of the formula (CH₂)₂OC(O)N(R¹⁴)₂ where each $R^{14}$ is of the formula —(CH₂)₆NHC(=NH)NH₂; and $R^3$ is selected from an electron pair, H, and $C_1$-$C_6$ alkyl, where G is a cell penetrating peptide ("CPP") and linker moiety selected from —C(O)(CH₂)hd 5NH-CPP, —C(O)(CH₂)₂NH-CPP, —C(O)(CH₂)₂ NHC(O)(CH₂)₅NH-CPP, and —C(O)CH₂NH-CPP, or G is of the formula:

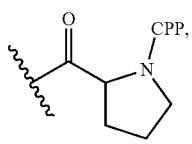

where the CPP is attached to the linker moiety by an amide bond at the CPP carboxy terminus, and wherein the CPP is selected from:

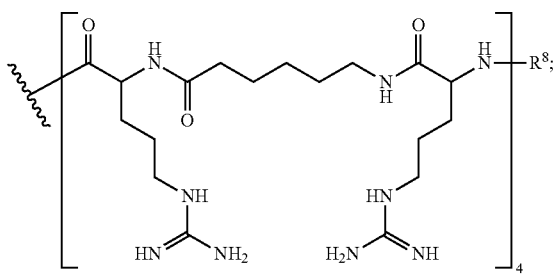

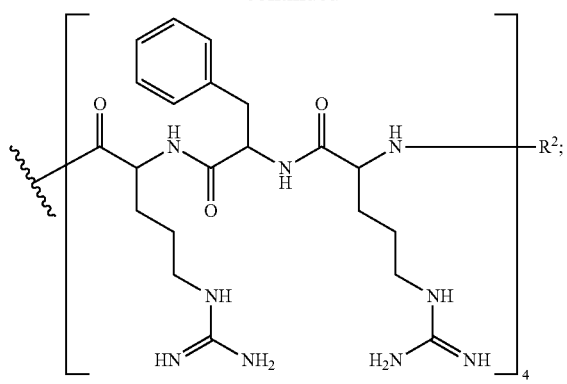

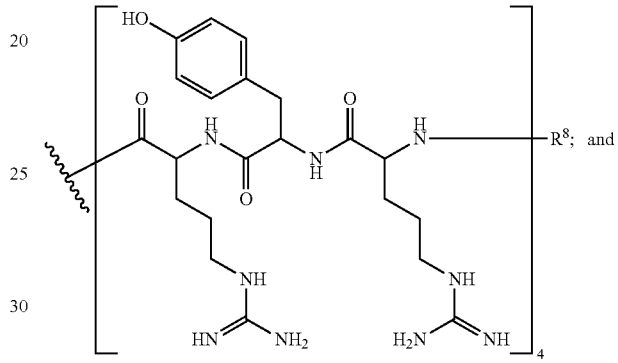

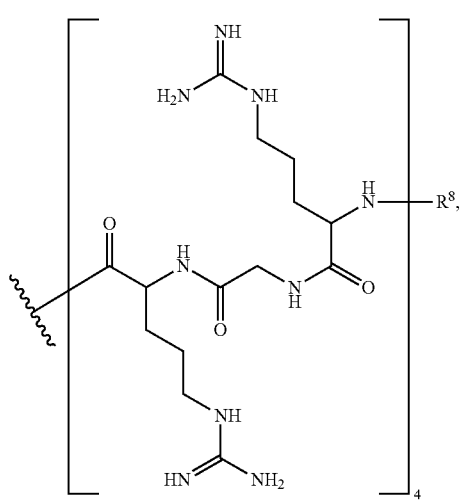

where Ra is selected from H, acetyl, benzoyl, and stearoyl, with the proviso that $R^2$ or $R^8$ is G, where the targeting sequence specifically hybridizes to a bacterial mRNA target sequence that encodes a protein selected from at least one of a protein associated with a biochemical pathway and/or cellular process and antibiotic resistance.

2. The antisense morpholino oligomer of claim 1, where T is selected from:

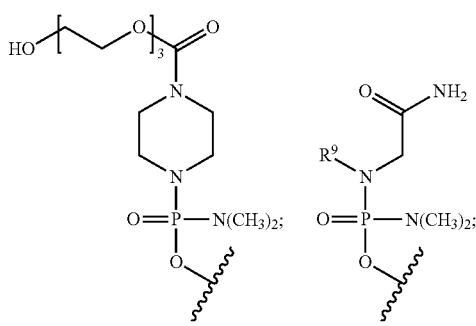

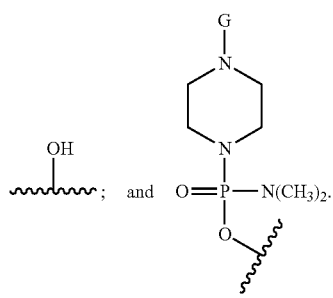

3. The antisense morpholino oligomer of claim 2, where $R^2$ is selected from H, G, acyl, trityl, 4-methoxytrityl, benzoyl, and stearoyl.

4. The antisense morpholino oligomer of claim 3, where T is selected from:

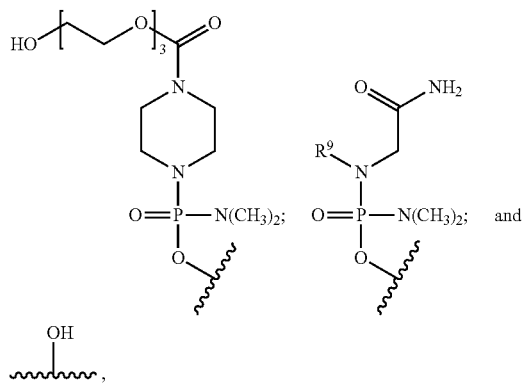

and

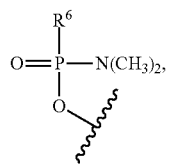

and $R^2$ is G.

5. The antisense morpholino oligomer of claim 1, where T is of the formula:

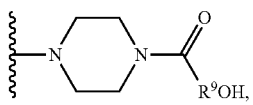

$R^6$ is of the formula:

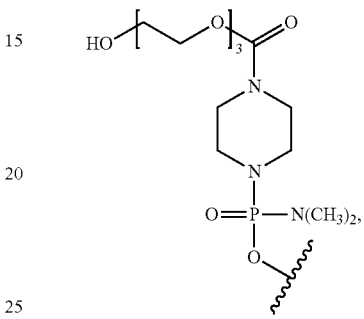

and $R^2$ is G.

6. The antisense morpholino oligomer of claim 1, where T is of the formula:

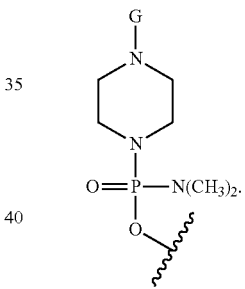

and $R^2$ is G.

7. The antisense morpholino oligomer of claim 1, where T is of the formula:

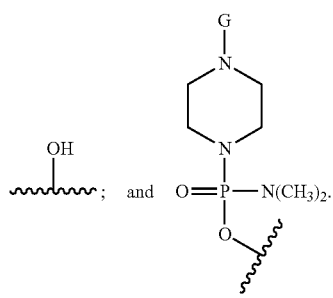

8. The antisense morpholino oligomer of claim 7, where $R^2$ is selected from H, acyl, trityl, 4-methoxytrityl, benzoyl, and stearoyl.

9. The antisense morpholino oligomer of claim 8, where at least one instance of $R^1$ is —$N(CH_3)_2$.

10. The antisense morpholino oligomer of claim 9, where each $R^1$ is —$N(CH_3)_2$.

11. The antisense morpholino oligomer of claim 1, where the CPP is selected from:

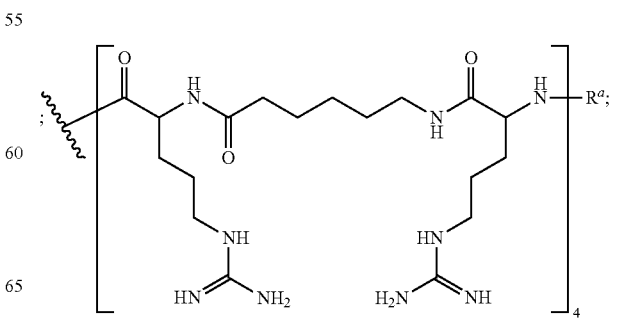

111
-continued
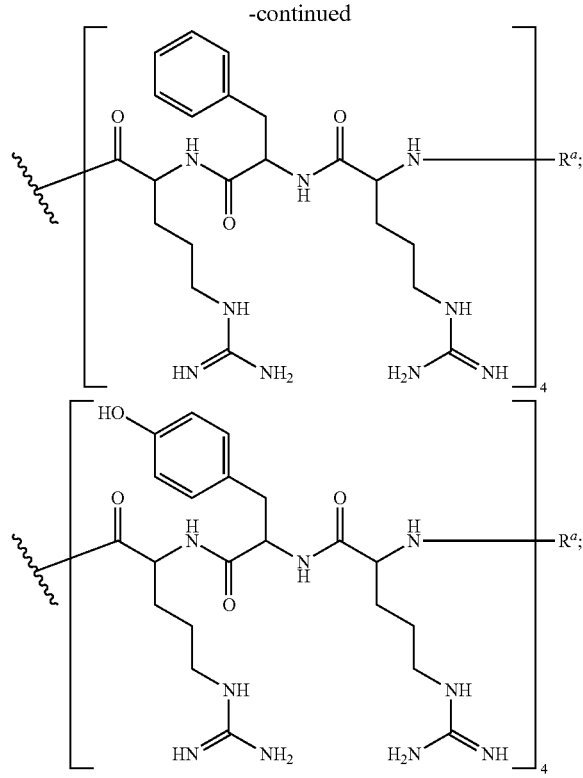
112
-continued
and
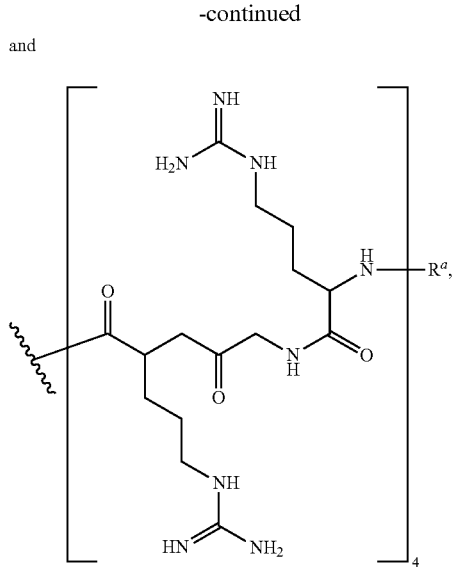
where Ra is selected from H, acetyl, benzoyl, and stearoyl.
12. The antisense morpholino oligomer of claim 1, where G is selected from:
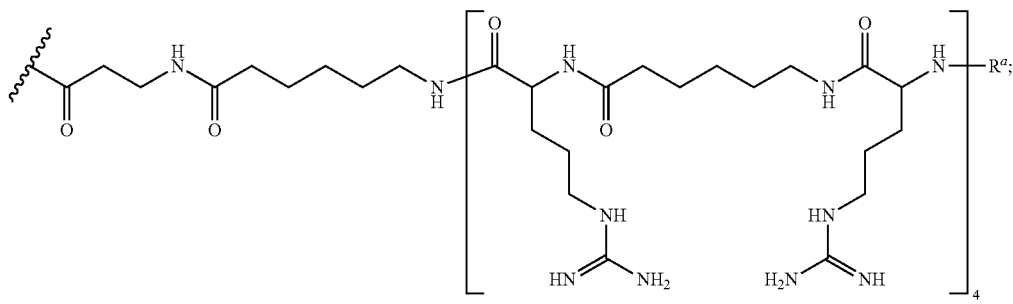
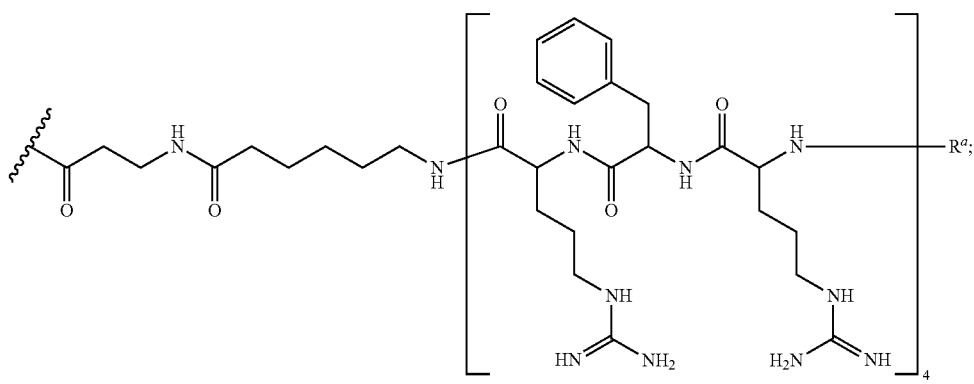

-continued
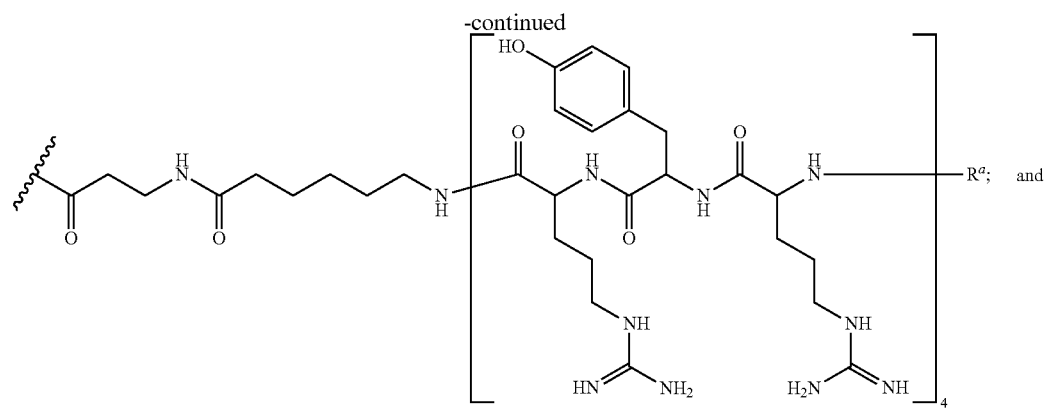
where $R^a$ is selected from H, acetyl, benzoyl, and stearoyl.
13. The antisense morpholino oligomer of claim 1, where the antisense oligomer is of the formula (VII) selected from:
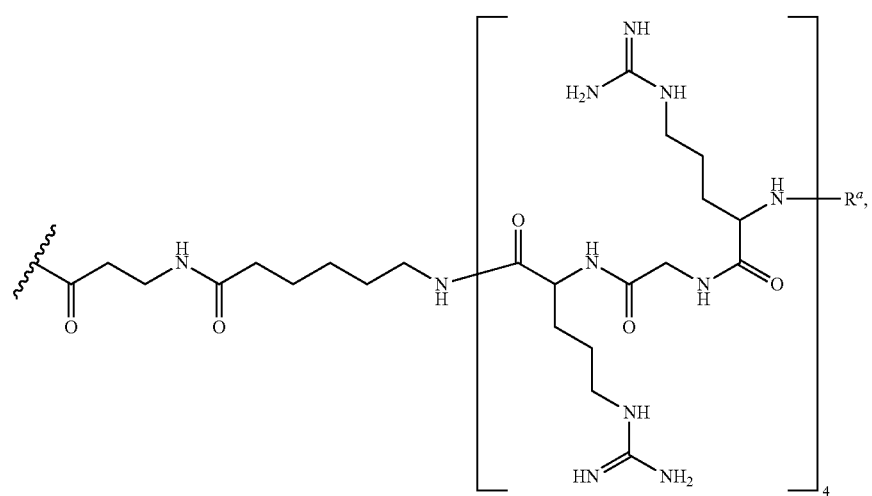

(VII A)
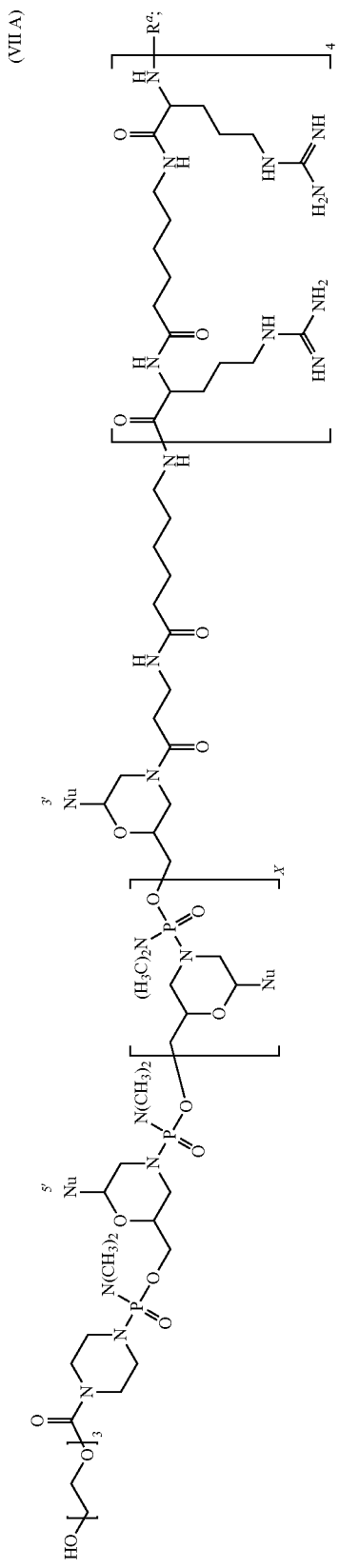
(VII B)
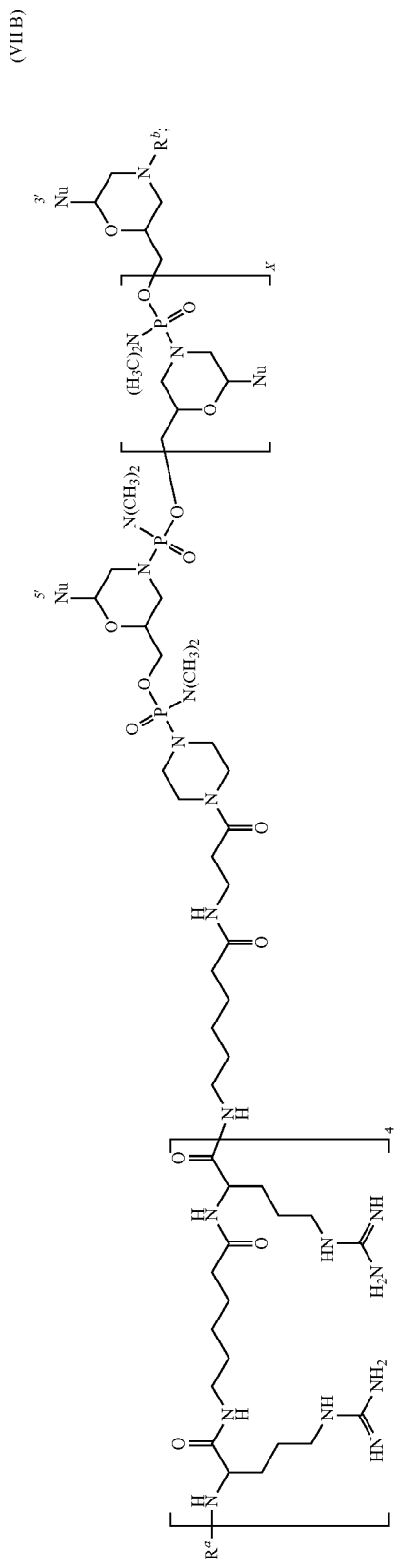

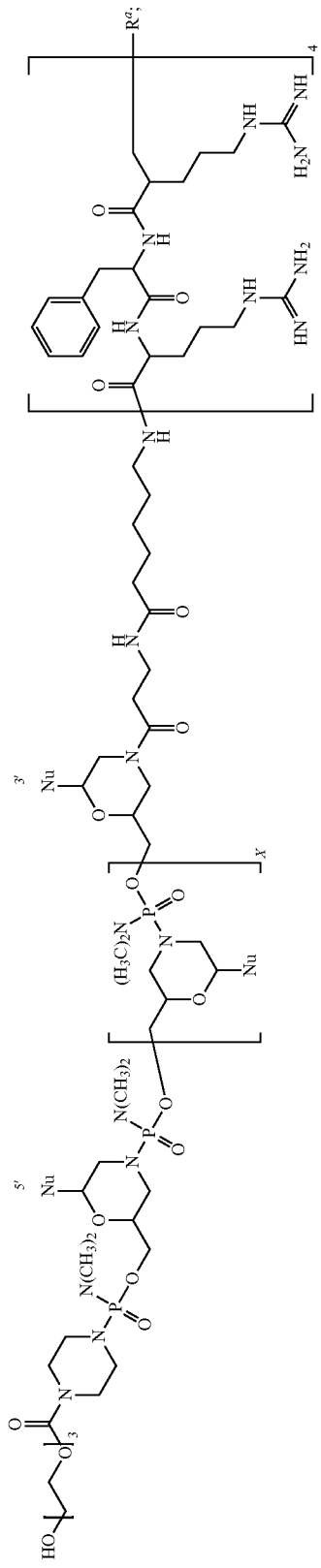
(VIIG)
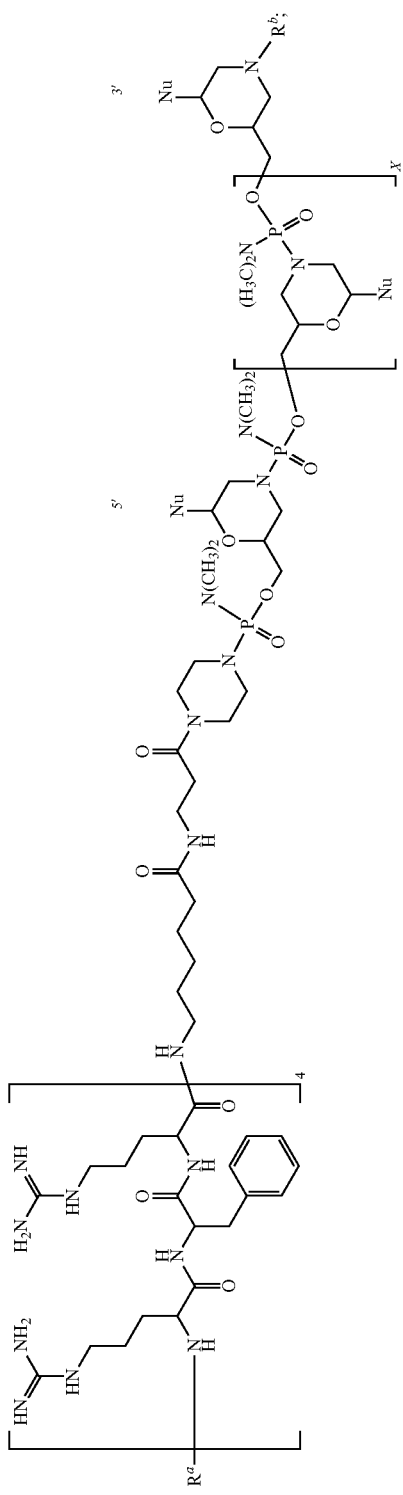
(VIIH)

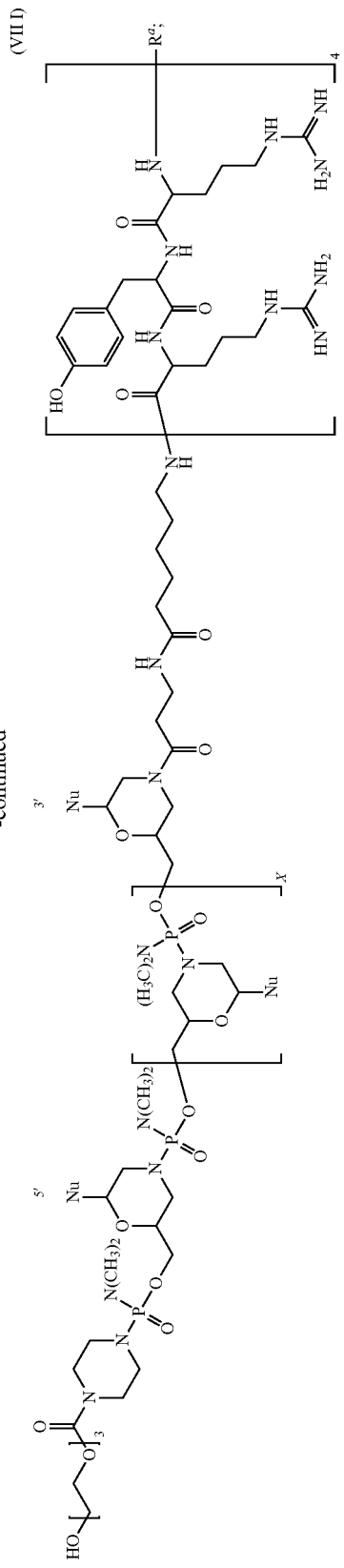
(VIII)
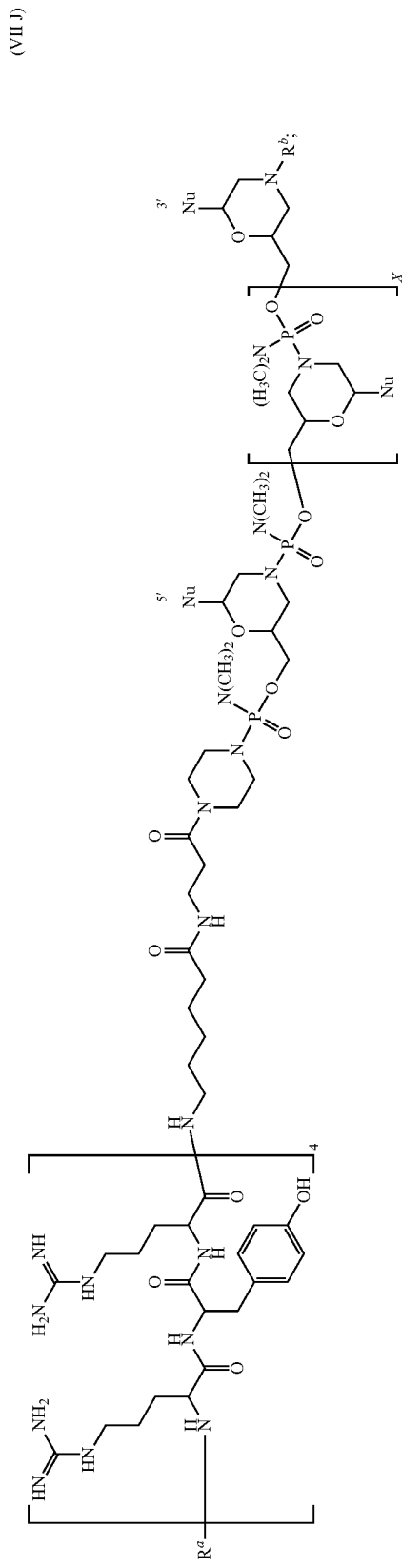
(VIIJ)

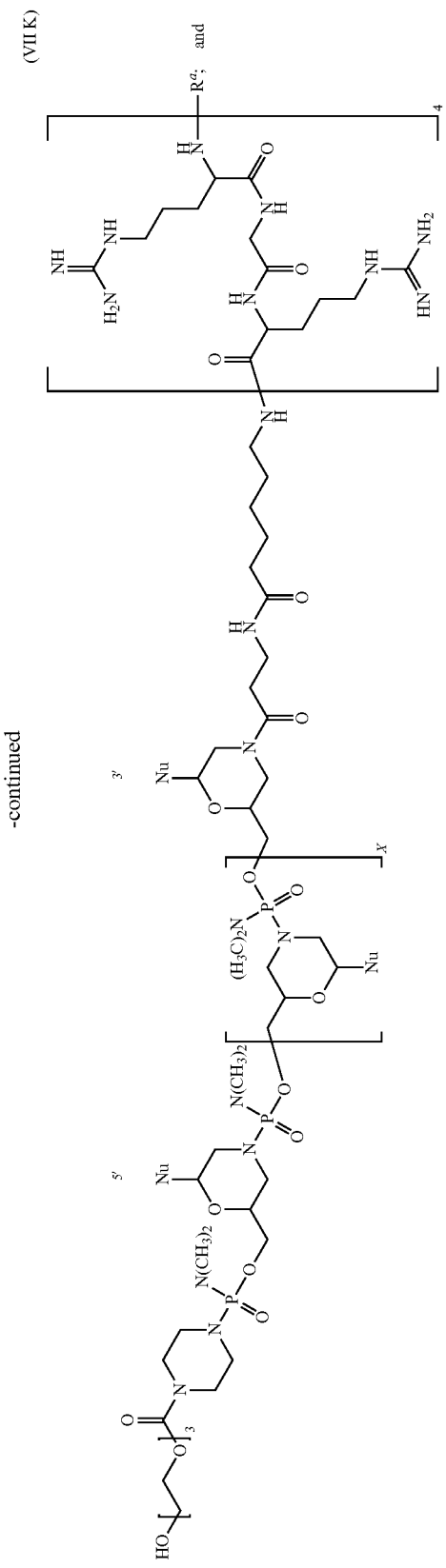
(VIIK)
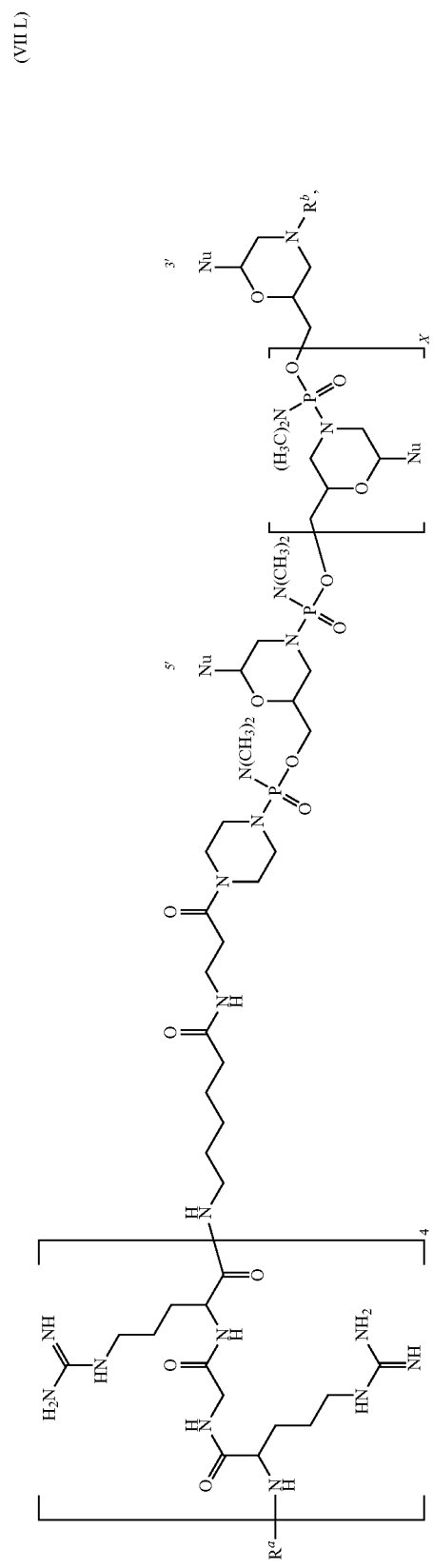
(VIIL)

or a pharmaceutically acceptable salt of any of the foregoing, where Ra is selected from H, acetyl, benzoyl, and stearoyl, $R^b$ is selected from H, acetyl, benzoyl, stearoyl, trityl, and 4-methoxytrityl, and X and Nu are as defined in claim 1.

14. The antisense morpholino oligomer of claim 13, where $R^a$ is acetyl and $R^b$ is H.

15. The antisense morpholino oligomer of claim 1, where the targeting sequence is selected from:
b) SEQ ID NO: 2 (ATATCGCTCAC) where X is 9;
c) SEQ ID NO: 3 (ATTCTCCTCAT) where X is 9;
d) SEQ ID NO: 4 (CACAGGAATTC) where X is 9;
e) SEQ ID NO: 5 (TTGCCATTAGC) where X is 9;
f) SEQ ID NO: 6 (CTGTAGTGATTTCACCA) where X is 15;
g) SEQ ID NO: 7 (TTATCTACCAT) where X is 9;
h) SEQ ID NO: 8 (GCACGTTTCAT) where X is 9;
i) SEQ ID NO: 9 (AGAAAACCCAT) where X is 9;
j) SEQ ID NO: 10 (TTGATAGTCAT) where X is 9; and
k) SEQ ID NO: 11 (GCTTTTTTCAT) where X is 9,
where thymine bases (T) may be uracil bases (U).

16. A pharmaceutical composition, wherein the antisense morpholino oligomer is of formula (I):

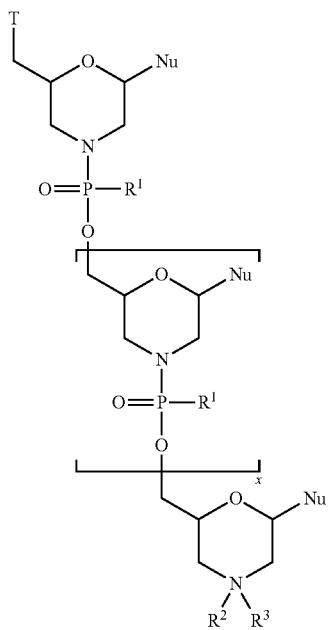

(I)

or a pharmaceutically acceptable salt thereof,
where each Nu is a nucleobase which taken together forms a targeting sequence,
where the targeting sequence is set forth in SEQ ID NOS: 2-11, comprises a fragment of at least 10 contiguous nucleotides of SEQ ID NOS: 2-11, or comprises a variant having at least 80% sequence identity to SEQ ID NOS: 2-11, where thymine bases (T) are optionally uracil bases (U);
X is an integer from 9 to 38;

T is selected from OH and a moiety of the formula:

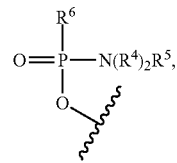

where each $R^4$ is independently $C_1$-$C_6$ alkyl, and $R^5$ is selected from an electron pair and H, and $R^6$ is selected from OH, —N($R^7$)$CH_2$C(O)$NH_2$, and a moiety of the formula:

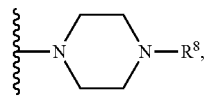

where
$R^7$ is selected from H and $C_1$-$C_6$ alkyl; and
$R^8$ is selected from G, —C(O)—$R^9$OH, acyl, trityl, and 4-methoxytrityl, where:
$R^9$ is of the formula —(O-alkyl)$_y$- where y is an integer from 3 to 20 and each of the y alkyl groups is independently selected from $C_2$-$C_6$ alkyl,
each of $R^1$ is —N($R^{10}$)$_2$$R^{11}$ where each $R^{10}$ is independently $C_1$-$C_6$ alkyl, and
$R^{11}$ is selected from an electron pair and H;
$R^2$ is selected from H, G, acyl, trityl, 4-methoxytrityl, benzoyl, stearoyl, and a moiety of the formula:

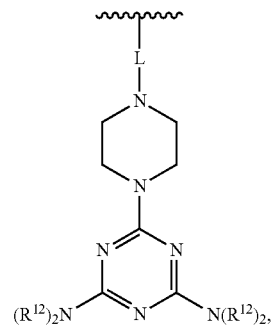

where L is selected from —C(O)($CH_2$)$_6$C(O)— and —C(O)($CH_2$)$_2$$S_2$($CH_2$)$_2$C(O)—, and each $R^{12}$ is of the formula —($CH_2$)$_2$OC(O)N($R^{14}$)$_2$ where each $R^{14}$ is of the formula —($CH_2$)$_6$NHC(=NH)$NH_2$; and
$R^3$ is selected from an electron pair, H, and $C_1$-$C_6$ alkyl,
where G is a cell penetrating peptide ("CPP") and linker moiety selected from —C(O)($CH_2$)$_5$NH-CPP, —C(O)($CH_2$)$_2$NH-CPP, —C(O)($CH_2$)$_2$NHC(O)($CH_2$)$_5$NH-CPP, and —C(O)$CH_2$NH-CPP, or G is of the formula:

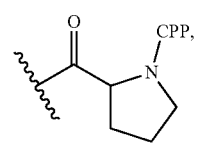

where the CPP is attached to the linker moiety by an amide bond at the CPP carboxy terminus, and wherein the CPP is selected from:

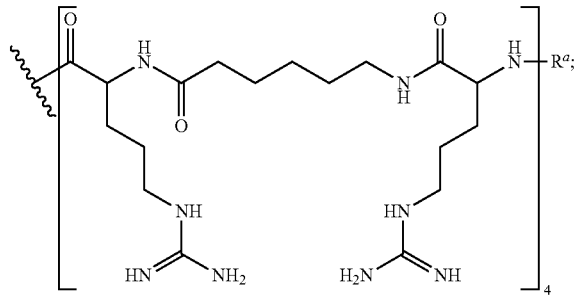

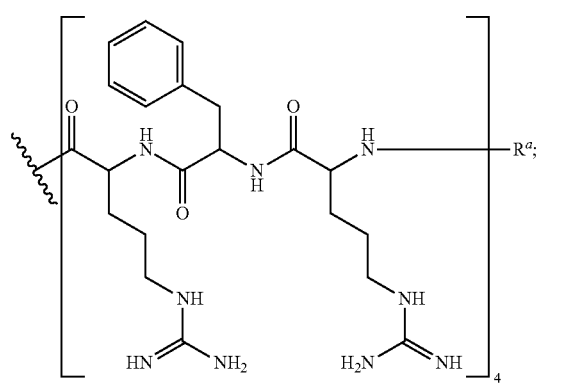

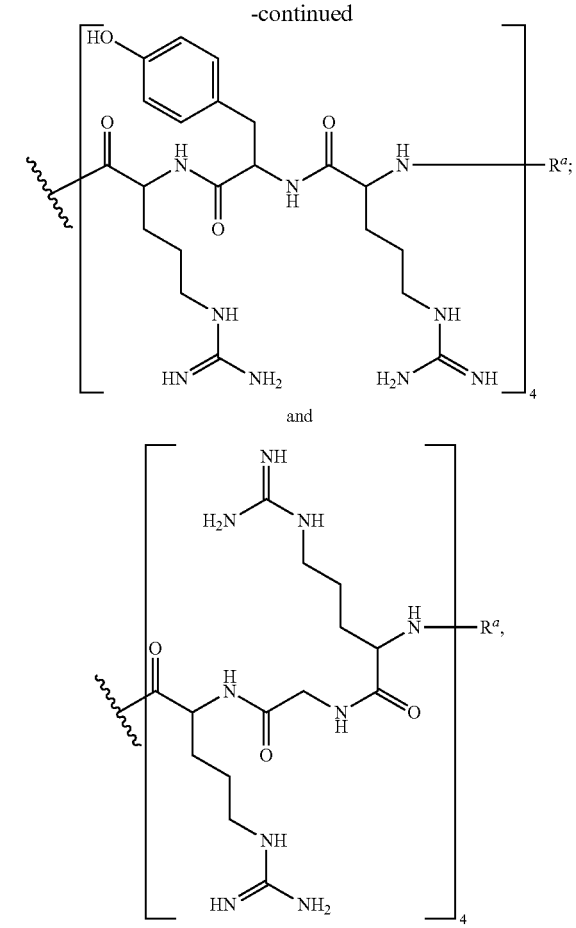

where Ra is selected from H, acetyl, benzoyl, and stearoyl, with the proviso that $R^2$ or $R^8$ is G, where the targeting sequence specifically hybridizes to a bacterial mRNA target sequence that encodes a protein selected from at least one of a protein associated with a biochemical pathway and/or cellular process and antibiotic resistance.

* * * * *

UNITED STATES PATENT AND TRADEMARK OFFICE
CERTIFICATE OF CORRECTION

PATENT NO. : 10,391,098 B2
APPLICATION NO. : 14/714104
DATED : August 27, 2019
INVENTOR(S) : Bruce L. Geller et al.

It is certified that error appears in the above-identified patent and that said Letters Patent is hereby corrected as shown below:

In the Claims

Claim 1, Column 107, Lines 38-39, delete "-C(O)(CH$_2$)hd5NH-CPP" and insert -- -C(O)(CH$_2$)$_5$NH-CPP-- therefor.

Claim 1, Column 107, Line 56 to Column 108, Line 56, delete the four chemical drawings and insert the following:

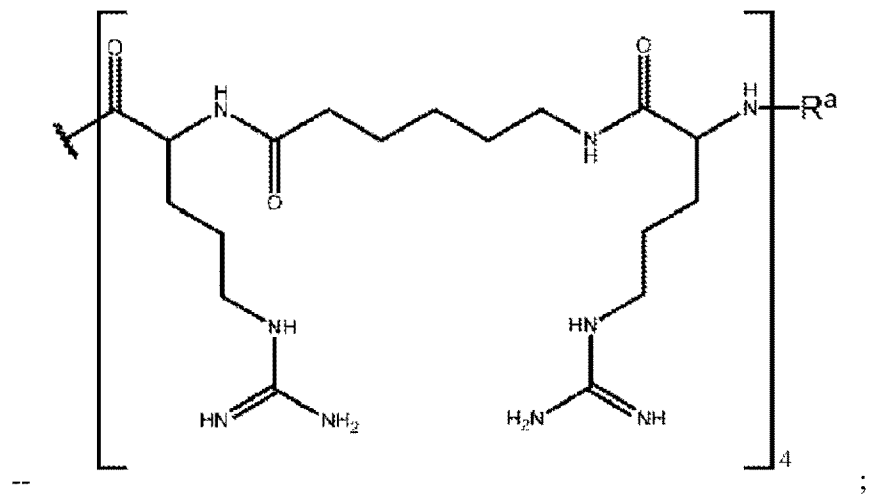

Signed and Sealed this
Twenty-eighth Day of April, 2020

Andrei Iancu
*Director of the United States Patent and Trademark Office*

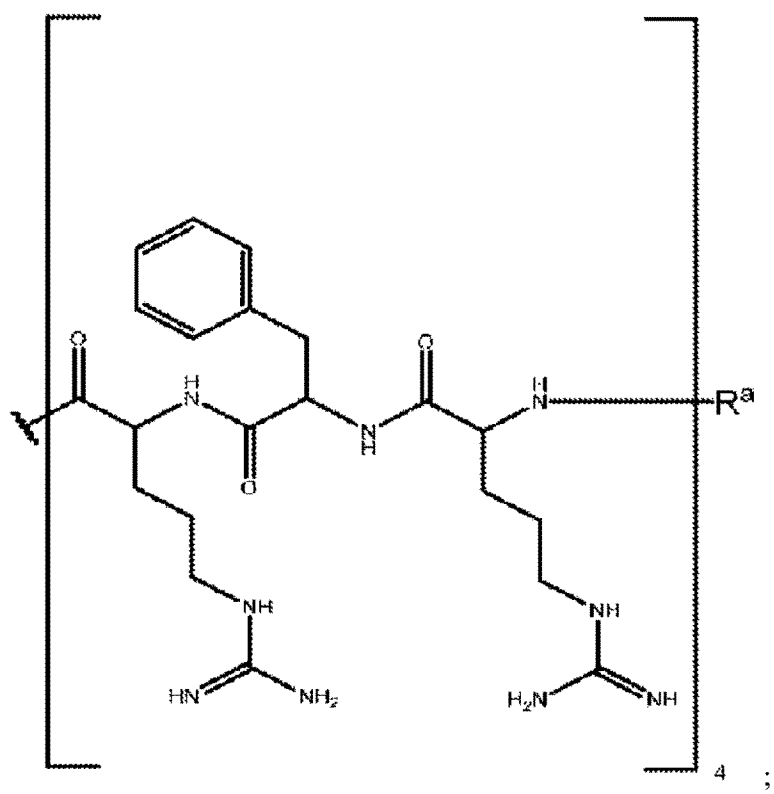
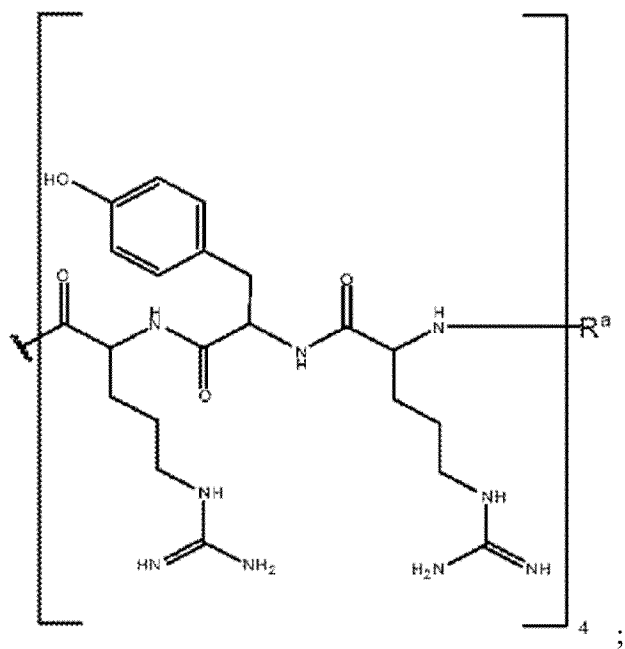
and

CERTIFICATE OF CORRECTION (continued)
U.S. Pat. No. 10,391,098 B2

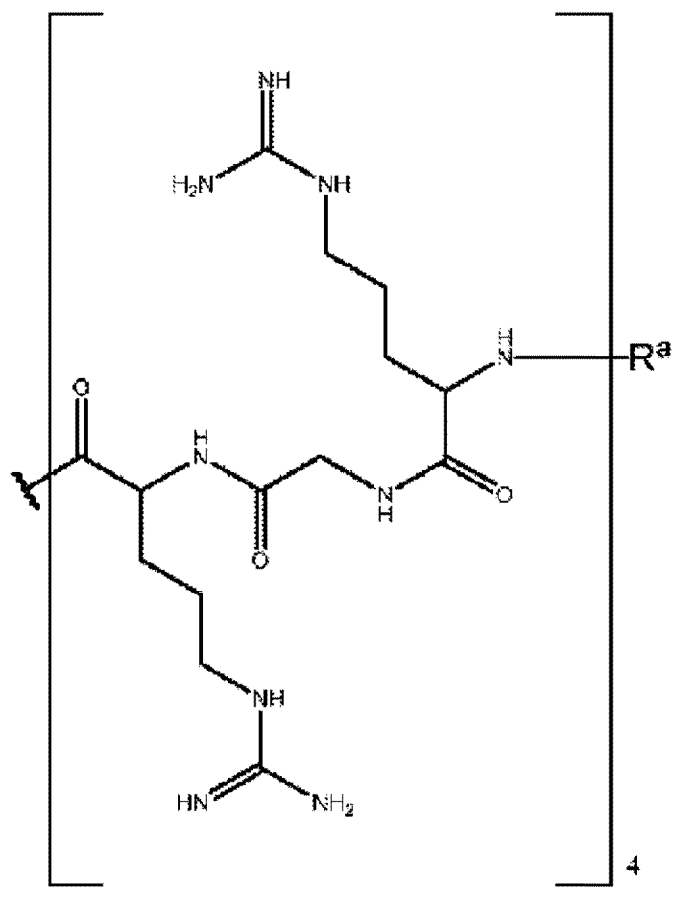

,-- therefor.

Claim 11, Column 112, Lines 3-23, delete chemical drawing and insert:

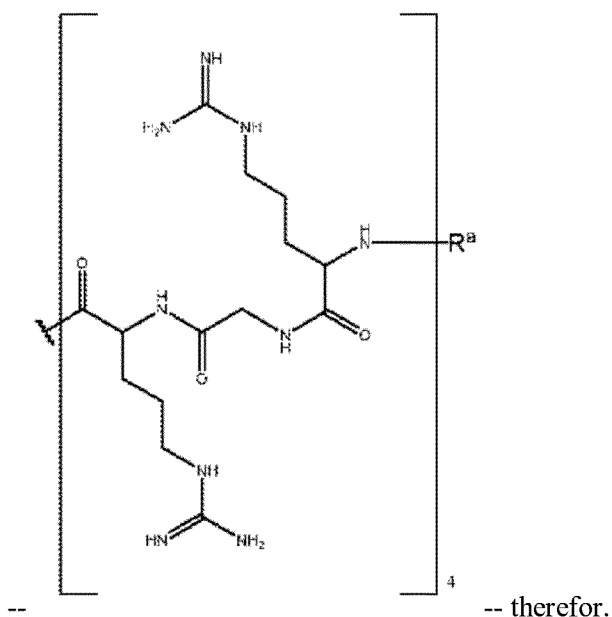

-- therefor.

Claim 16, Column 124, Line 29, delete "of".